United States Patent
Gu et al.

(10) Patent No.: US 12,428,482 B2
(45) Date of Patent: Sep. 30, 2025

(54) ANTI-PD-1 ANTIBODY, ANTIGEN-BINDING FRAGMENT THEREOF AND PHARMACEUTICAL USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Xiaoling Gu, Shanghai (CN); Xin Ye, Shanghai (CN); Hu Ge, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1094 days.

(21) Appl. No.: 17/427,625

(22) PCT Filed: Jan. 31, 2020

(86) PCT No.: PCT/CN2020/074098
§ 371 (c)(1),
(2) Date: Jul. 30, 2021

(87) PCT Pub. No.: WO2020/156509
PCT Pub. Date: Aug. 6, 2020

(65) Prior Publication Data
US 2022/0098304 A1    Mar. 31, 2022

(30) Foreign Application Priority Data

Feb. 3, 2019   (CN) .......................... 201910108743.3
Jan. 17, 2020  (CN) .......................... 202010052351.2

(51) Int. Cl.
| | |
|---|---|
| *C07K 16/28* | (2006.01) |
| *A61K 39/00* | (2006.01) |
| *A61P 35/00* | (2006.01) |
| *C12N 15/11* | (2006.01) |

(52) U.S. Cl.
CPC .......... *C07K 16/2818* (2013.01); *A61P 35/00* (2018.01); *A61K 2039/505* (2013.01); *C07K 2317/24* (2013.01); *C07K 2317/31* (2013.01); *C07K 2317/52* (2013.01); *C07K 2317/565* (2013.01); *C07K 2317/73* (2013.01); *C07K 2317/76* (2013.01); *C07K 2317/92* (2013.01); *C12N 15/11* (2013.01)

(58) Field of Classification Search
CPC .......... C07K 16/2818; C07K 2317/24; C07K 2317/31; C07K 2317/52; C07K 2317/565; C07K 2317/73; C07K 2317/76; C07K 2317/92; A61P 35/00; A61K 2039/505; C12N 15/11
See application file for complete search history.

(56) References Cited

U.S. PATENT DOCUMENTS

| | | | |
|---|---|---|---|
| 6,803,192 B1 | 10/2004 | Chen | |
| 8,617,546 B2 | 12/2013 | Kang | |
| 9,637,546 B2* | 5/2017 | Olive | ...................... A61P 31/10 |
| 2014/0335093 A1 | 11/2014 | Olive | |

FOREIGN PATENT DOCUMENTS

| | | |
|---|---|---|
| CN | 104250302 A | 12/2014 |
| CN | 106573052 A | 4/2017 |
| CN | 108976300 A | 12/2018 |
| EP | 2439273 A2 | 4/2012 |
| WO | 2001039722 A2 | 6/2001 |
| WO | 2006121168 A1 | 11/2006 |
| WO | 2010036959 A2 | 4/2010 |
| WO | 2010089411 A2 | 8/2010 |
| WO | 2011110604 A1 | 9/2011 |
| WO | 2013173223 A1 | 11/2013 |
| WO | 2013181634 A2 | 12/2013 |
| WO | 2015085847 A1 | 6/2015 |

OTHER PUBLICATIONS

Almagro JC, Daniels-Wells TR, Perez-Tapia SM, Penichet ML. Progress and Challenges in the Design and Clinical Development of Antibodies for Cancer Therapy. Front Immunol. Jan. 4, 2018;8:1751. doi: 10.3389/fimmu.2017.01751. PMID: 29379493; PMCID: PMC5770808. (Year: 2018).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. doi: 10.4049/jimmunol.165.8.4505. PMID: 11035090. (Year: 2000).*

Thomas K. Eigentler et al., Diagnosis, monitoring and management of immune-related adverse drug reactions of anti-PD-1 antibody therapy, Cancer Treatment Reviews, vol. 45, Dec. 31, 2016, pp. 7-18.

(Continued)

*Primary Examiner* — Hong Sang
*Assistant Examiner* — Carol Ann Chase
(74) *Attorney, Agent, or Firm* — Morgan, Lewis & Bockius LLP

(57) ABSTRACT

Provided are an anti-PD-1 antibody, an antigen-binding fragment thereof, and a pharmaceutical use thereof. Specifically, provided are a humanized anti-PD-1 antibody containing a specific CDR region and an antigen-binding fragment thereof, a pharmaceutical composition containing the anti-PD-1 antibody and the antigen-binding fragment thereof, and a used thereof as medicament. In particular, provided is a use of the humanized anti-PD-1 antibody in the preparation of the medicament for treating PD-1 associated diseases or disorders.

19 Claims, 3 Drawing Sheets
Specification includes a Sequence Listing.

(56) References Cited

OTHER PUBLICATIONS

Ma Baozhen et al., English Translation of: Anti-PD-1 and PD-L1 Therapy in Oncotherapy (Anti-PD-1 and PD-L1 Advances in Tumor Therapy), Chinese Journal of Immunology, vol. 33, No. 5, Dec. 31, 2017, pp. 796-800 (13 pages).

* cited by examiner

SEQUENCE LISTING

```
<160> NUMBER OF SEQ ID NOS: 82

<210> SEQ ID NO 1
<211> LENGTH: 401
<212> TYPE: PRT
<213> ORGANISM: Artificial sequence
<220> FEATURE:
<223> OTHER INFORMATION: Synthetic Sequence_Human PD-1-IgG1Fc sequence

<400> SEQUENCE: 1

Met Glu Phe Gly Leu Ser Trp Leu Phe Leu Val Ala Ile Leu Lys Gly
1               5                   10                  15

Val Gln Cys Pro Gly Trp Phe Leu Asp Ser Pro Asp Arg Pro Trp Asn
            20                  25                  30

Pro Pro Thr Phe Ser Pro Ala Leu Leu Val Val Thr Glu Gly Asp Asn
        35                  40                  45

Ala Thr Phe Thr Cys Ser Phe Ser Asn Thr Ser Glu Ser Phe Val Leu
    50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Glu Pro Lys Ser Ser Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
    210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270
```

```
Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
                340                 345                 350

Asp Ser Asp Gly Ser Phe Phe Leu Tyr Ser Lys Leu Thr Val Asp Lys
                355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro Gly
385                 390                 395                 400

Lys

<210> SEQ ID NO 2
<211> LENGTH: 186
<212> TYPE: PRT
<213> ORGANISM: Artificial sequence
<220> FEATURE:
<223> OTHER INFORMATION: Synthetic Sequence_Human PD-1-his sequence

<400> SEQUENCE: 2

Met Glu Phe Gly Leu Ser Trp Leu Phe Leu Val Ala Ile Leu Lys Gly
1               5                   10                  15

Val Gln Cys Pro Gly Trp Phe Leu Asp Ser Pro Asp Arg Pro Trp Asn
            20                  25                  30

Pro Pro Thr Phe Ser Pro Ala Leu Leu Val Val Thr Glu Gly Asp Asn
        35                  40                  45

Ala Thr Phe Thr Cys Ser Phe Ser Asn Thr Ser Glu Ser Phe Val Leu
    50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Gly Ser Ser Asp Tyr Lys Asp
                165                 170                 175

Asp Asp Asp Lys His His His His His
            180                 185

<210> SEQ ID NO 3
<211> LENGTH: 288
<212> TYPE: PRT
<213> ORGANISM: Artificial sequence
<220> FEATURE:
```

<223> OTHER INFORMATION: Synthetic Sequence_PD-1 antigen sequence for
       cell transfection

<400> SEQUENCE: 3

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 4
<211> LENGTH: 125
<212> TYPE: PRT
<213> ORGANISM: Mus musculus

<400> SEQUENCE: 4

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Ile His Gly Leu Glu Trp Ile
        35                  40                  45

Gly Leu Ile Asp Pro Glu Thr Gly Gly Thr Val Tyr Asn Gln Lys Phe
    50                  55                  60

```
Lys Asp Lys Thr Ile Leu Thr Ala Asp Lys Ser Ser Thr Ala Tyr
 65                  70                  75                  80

Met Glu Phe Arg Ser Leu Thr Ser Glu Asp Ser Ala Val Tyr His Cys
                 85                  90                  95

Thr Arg Glu Arg Phe Ser Tyr Tyr Gly Ser Thr Ser Asp Trp Tyr Phe
            100                 105                 110

Asp Val Trp Gly Thr Gly Thr Thr Val Thr Val Ser Ser
            115                 120                 125

<210> SEQ ID NO 5
<211> LENGTH: 112
<212> TYPE: PRT
<213> ORGANISM: Mus musculus

<400> SEQUENCE: 5

Asp Gly Leu Met Thr Gln Thr Pro Leu Ser Leu Pro Val Ser Leu Gly
  1               5                  10                  15

Asp His Ala Ser Ile Ser Cys Arg Ser Ser Gln Ser Leu Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Tyr Cys Phe Gln Gly
                 85                  90                  95

Ser His Val Pro Tyr Thr Phe Gly Gly Gly Thr Lys Leu Glu Ile Lys
            100                 105                 110

<210> SEQ ID NO 6
<211> LENGTH: 120
<212> TYPE: PRT
<213> ORGANISM: Mus musculus

<400> SEQUENCE: 6

Gln Val Gln Leu Gln Gln Ser Gly Ala Glu Leu Val Arg Pro Gly Ala
  1               5                  10                  15

Ser Val Thr Leu Ser Cys Lys Ala Ser Asp Phe Thr Phe Thr Asp Tyr
                 20                  25                  30

Glu Ile His Trp Val Lys Gln Thr Pro Val His Gly Leu Glu Trp Ile
             35                  40                  45

Gly Leu Phe Asp Pro Glu Thr Gly Gly Ile Val Tyr Asn Gln Lys Phe
 50                  55                  60

Lys Gly Lys Ala Ile Leu Thr Ala Asp Lys Ser Ser Asn Thr Ala Tyr
 65                  70                  75                  80

Met Glu Phe Arg Ser Leu Thr Ser Glu Asp Ser Ala Val Tyr Tyr Cys
                 85                  90                  95

Thr Arg Glu Gly Gly Tyr Asn Arg Asp Trp Tyr Phe Asp Val Trp Gly Thr
            100                 105                 110

Gly Thr Thr Val Thr Val Ser Ser
            115                 120

<210> SEQ ID NO 7
<211> LENGTH: 112
<212> TYPE: PRT
<213> ORGANISM: Mus musculus
```

<400> SEQUENCE: 7

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Ile Tyr Tyr Cys Phe Gln Gly
                85                  90                  95

Ser His Val Pro Tyr Ala Phe Gly Gly Gly Thr Lys Leu Glu Ile Lys
                100                 105                 110

<210> SEQ ID NO 8
<211> LENGTH: 5
<212> TYPE: PRT
<213> ORGANISM: Mus musculus

<400> SEQUENCE: 8

Asp Tyr Glu Met His
1               5

<210> SEQ ID NO 9
<211> LENGTH: 17
<212> TYPE: PRT
<213> ORGANISM: Mus musculus

<400> SEQUENCE: 9

Leu Ile Asp Pro Glu Thr Gly Gly Thr Val Tyr Asn Gln Lys Phe Lys
1               5                   10                  15

Asp

<210> SEQ ID NO 10
<211> LENGTH: 16
<212> TYPE: PRT
<213> ORGANISM: Mus musculus

<400> SEQUENCE: 10

Glu Arg Phe Ser Tyr Tyr Gly Ser Thr Ser Asp Trp Tyr Phe Asp Val
1               5                   10                  15

<210> SEQ ID NO 11
<211> LENGTH: 16
<212> TYPE: PRT
<213> ORGANISM: Mus musculus

<400> SEQUENCE: 11

Arg Ser Ser Gln Ser Leu Val His Ser Asn Gly Lys Thr Tyr Leu Glu
1               5                   10                  15

<210> SEQ ID NO 12
<211> LENGTH: 7
<212> TYPE: PRT
<213> ORGANISM: Mus musculus

<400> SEQUENCE: 12

Lys Val Ser Asn Arg Phe Ser
1               5

```
<210> SEQ ID NO 13
<211> LENGTH: 9
<212> TYPE: PRT
<213> ORGANISM: Mus musculus

<400> SEQUENCE: 13

Phe Gln Gly Ser His Val Pro Tyr Thr
1               5

<210> SEQ ID NO 14
<211> LENGTH: 5
<212> TYPE: PRT
<213> ORGANISM: Mus musculus

<400> SEQUENCE: 14

Asp Tyr Glu Ile His
1               5

<210> SEQ ID NO 15
<211> LENGTH: 17
<212> TYPE: PRT
<213> ORGANISM: Mus musculus

<400> SEQUENCE: 15

Leu Phe Asp Pro Glu Thr Gly Gly Ile Val Tyr Asn Gln Lys Phe Lys
1               5                   10                  15

Gly

<210> SEQ ID NO 16
<211> LENGTH: 11
<212> TYPE: PRT
<213> ORGANISM: Mus musculus

<400> SEQUENCE: 16

Glu Gly Tyr Asn Arg Asp Trp Tyr Phe Asp Val
1               5                   10

<210> SEQ ID NO 17
<211> LENGTH: 16
<212> TYPE: PRT
<213> ORGANISM: Mus musculus

<400> SEQUENCE: 17

Arg Ser Ser Gln Ser Ile Val His Ser Asn Gly Asn Thr Tyr Leu Glu
1               5                   10                  15

<210> SEQ ID NO 18
<211> LENGTH: 9
<212> TYPE: PRT
<213> ORGANISM: Mus musculus

<400> SEQUENCE: 18

Phe Gln Gly Ser His Val Pro Tyr Ala
1               5

<210> SEQ ID NO 19
<211> LENGTH: 118
<212> TYPE: PRT
<213> ORGANISM: Mus musculus

<400> SEQUENCE: 19

Lys Val Met Leu Val Glu Ser Gly Gly Gly Leu Val Lys Pro Gly Gly
1               5                   10                  15
```

```
Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
            35                  40                  45

Ala Thr Ile Ser Gly Gly Gly Val Asp Thr Tyr Tyr Gln Asp Asn Val
        50                  55                  60

Gln Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Ser Pro Tyr Gly His Gly Tyr Phe Asp Val Trp Gly Thr Gly Thr
            100                 105                 110

Thr Val Thr Val Ser Ser
            115
```

<210> SEQ ID NO 20
<211> LENGTH: 107
<212> TYPE: PRT
<213> ORGANISM: Mus musculus

<400> SEQUENCE: 20

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Phe
            20                  25                  30

Leu Asn Trp Tyr Gln Gln Lys Pro Asp Gly Thr Val Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 21
<211> LENGTH: 5
<212> TYPE: PRT
<213> ORGANISM: Mus musculus

<400> SEQUENCE: 21

```
Ser Tyr Ala Met Ser
1               5
```

<210> SEQ ID NO 22
<211> LENGTH: 17
<212> TYPE: PRT
<213> ORGANISM: Mus musculus

<400> SEQUENCE: 22

```
Thr Ile Ser Gly Gly Gly Val Asp Thr Tyr Tyr Gln Asp Asn Val Gln
1               5                   10                  15

Gly
```

<210> SEQ ID NO 23
<211> LENGTH: 9
<212> TYPE: PRT

```
<213> ORGANISM: Mus musculus

<400> SEQUENCE: 23

Pro Tyr Gly His Gly Tyr Phe Asp Val
1               5

<210> SEQ ID NO 24
<211> LENGTH: 11
<212> TYPE: PRT
<213> ORGANISM: Mus musculus

<400> SEQUENCE: 24

Arg Ala Ser Gln Asp Ile Asn Asn Phe Leu Asn
1               5                   10

<210> SEQ ID NO 25
<211> LENGTH: 7
<212> TYPE: PRT
<213> ORGANISM: Mus musculus

<400> SEQUENCE: 25

Tyr Thr Ser Ser Leu His Ser
1               5

<210> SEQ ID NO 26
<211> LENGTH: 9
<212> TYPE: PRT
<213> ORGANISM: Mus musculus

<400> SEQUENCE: 26

Gln Gln Gly Asn Thr Leu Pro Trp Thr
1               5

<210> SEQ ID NO 27
<211> LENGTH: 125
<212> TYPE: PRT
<213> ORGANISM: Artificial sequence
<220> FEATURE:
<223> OTHER INFORMATION: Synthetic Sequence_Hu23VH1 /Hu23VH-CDR grafted
      sequence

<400> SEQUENCE: 27

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Glu Met His Trp Val Arg Gln Ala Pro Gly Gln Gly Leu Glu Trp Met
        35                  40                  45

Gly Leu Ile Asp Pro Glu Thr Gly Gly Thr Val Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Phe Ser Tyr Tyr Gly Ser Thr Ser Asp Trp Tyr Phe
            100                 105                 110

Asp Val Trp Gly Gln Gly Thr Thr Val Thr Val Ser Ser
        115                 120                 125

<210> SEQ ID NO 28
<211> LENGTH: 112
<212> TYPE: PRT
```

<213> ORGANISM: Artificial sequence
<220> FEATURE:
<223> OTHER INFORMATION: Synthetic Sequence_Hu23VL1 /Hu23VL-CDR grafted
      sequence

<400> SEQUENCE: 28

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 29
<211> LENGTH: 112
<212> TYPE: PRT
<213> ORGANISM: Artificial sequence
<220> FEATURE:
<223> OTHER INFORMATION: Synthetic Sequence_Hu23VL2 sequence

<400> SEQUENCE: 29

Asp Gly Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 30
<211> LENGTH: 125
<212> TYPE: PRT
<213> ORGANISM: Artificial sequence
<220> FEATURE:
<223> OTHER INFORMATION: Synthetic Sequence_Hu23VH2 sequence

<400> SEQUENCE: 30

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Glu Met His Trp Val Arg Gln Ala Pro Gly Gln Gly Leu Glu Trp Met
        35                  40                  45

Gly Leu Ile Asp Pro Glu Thr Gly Gly Thr Val Tyr Asn Gln Lys Phe

```
                50                  55                  60
Lys Asp Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                    85                  90                  95

Ala Arg Glu Arg Phe Ser Tyr Tyr Gly Ser Thr Ser Asp Trp Tyr Phe
                100                 105                 110

Asp Val Trp Gly Gln Gly Thr Thr Val Thr Val Ser Ser
            115                 120                 125

<210> SEQ ID NO 31
<211> LENGTH: 125
<212> TYPE: PRT
<213> ORGANISM: Artificial sequence
<220> FEATURE:
<223> OTHER INFORMATION: Synthetic Sequence_Hu23VH3 sequence

<400> SEQUENCE: 31

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asp Tyr
                20                  25                  30

Glu Met His Trp Val Arg Gln Ala Pro Gly Gln Gly Leu Glu Trp Ile
            35                  40                  45

Gly Leu Ile Asp Pro Glu Thr Gly Gly Thr Val Tyr Asn Gln Lys Phe
        50                  55                  60

Lys Asp Arg Thr Thr Leu Thr Ala Asp Lys Ser Thr Ser Thr Ala Tyr
 65                  70                  75                  80

Met Glu Phe Ser Ser Leu Arg Ser Glu Asp Thr Ala Val Tyr Tyr Cys
                85                  90                  95

Ala Arg Glu Arg Phe Ser Tyr Tyr Gly Ser Thr Ser Asp Trp Tyr Phe
                100                 105                 110

Asp Val Trp Gly Gln Gly Thr Thr Val Thr Val Ser Ser
            115                 120                 125

<210> SEQ ID NO 32
<211> LENGTH: 125
<212> TYPE: PRT
<213> ORGANISM: Artificial sequence
<220> FEATURE:
<223> OTHER INFORMATION: Synthetic Sequence_Hu23VH4 sequence

<400> SEQUENCE: 32

Glu Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Ser Asp Tyr
                20                  25                  30

Glu Met His Trp Val Arg Gln Ala Pro Gly Gln Gly Leu Glu Trp Ile
            35                  40                  45

Gly Leu Ile Asp Pro Glu Thr Gly Gly Thr Val Tyr Asn Gln Lys Phe
        50                  55                  60

Lys Asp Arg Thr Thr Leu Thr Ala Asp Lys Ser Thr Ser Thr Ala Tyr
 65                  70                  75                  80

Met Glu Phe Ser Ser Leu Arg Ser Glu Asp Thr Ala Val Tyr Tyr Cys
                85                  90                  95

Thr Arg Glu Arg Phe Ser Tyr Tyr Gly Ser Thr Ser Asp Trp Tyr Phe
                100                 105                 110
```

-continued

Asp Val Trp Gly Gln Gly Thr Thr Val Thr Val Ser Ser
           115                 120                 125

<210> SEQ ID NO 33
<211> LENGTH: 120
<212> TYPE: PRT
<213> ORGANISM: Artificial sequence
<220> FEATURE:
<223> OTHER INFORMATION: Synthetic Sequence_Hu32VH1 /Hu32VH-CDR grafted
      sequence

<400> SEQUENCE: 33

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Glu Ile His Trp Val Arg Gln Ala Pro Gly Gln Gly Leu Glu Trp Met
        35                  40                  45

Gly Leu Phe Asp Pro Glu Thr Gly Gly Ile Val Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Asn Arg Asp Trp Tyr Phe Asp Val Trp Gly Gln
            100                 105                 110

Gly Thr Thr Val Thr Val Ser Ser
        115                 120

<210> SEQ ID NO 34
<211> LENGTH: 112
<212> TYPE: PRT
<213> ORGANISM: Artificial sequence
<220> FEATURE:
<223> OTHER INFORMATION: Synthetic Sequence_Hu32VL1 /Hu32VL-CDR grafted
      sequence

<400> SEQUENCE: 34

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Ala Phe Gly Gly Gly Thr Lys Val Glu Ile Lys
            100                 105                 110

<210> SEQ ID NO 35
<211> LENGTH: 112
<212> TYPE: PRT
<213> ORGANISM: Artificial sequence
<220> FEATURE:
<223> OTHER INFORMATION: Synthetic Sequence_Hu32VL2 sequence

<400> SEQUENCE: 35

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Ala Phe Gly Gly Gly Thr Lys Val Glu Ile Lys
            100                 105                 110

<210> SEQ ID NO 36
<211> LENGTH: 120
<212> TYPE: PRT
<213> ORGANISM: Artificial sequence
<220> FEATURE:
<223> OTHER INFORMATION: Synthetic Sequence_Hu32VH2 sequence

<400> SEQUENCE: 36

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Asp Tyr
            20                  25                  30

Glu Ile His Trp Val Arg Gln Ala Pro Gly Gln Gly Leu Glu Trp Met
        35                  40                  45

Gly Leu Phe Asp Pro Glu Thr Gly Gly Ile Val Tyr Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Tyr Asn Arg Asp Trp Tyr Phe Asp Val Trp Gly Gln
            100                 105                 110

Gly Thr Thr Val Thr Val Ser Ser
            115                 120

<210> SEQ ID NO 37
<211> LENGTH: 120
<212> TYPE: PRT
<213> ORGANISM: Artificial sequence
<220> FEATURE:
<223> OTHER INFORMATION: Synthetic Sequence_Hu32VH3 sequence

<400> SEQUENCE: 37

Glu Val Gln Leu Val Gln Ser Gly Ala Glu Val Lys Lys Pro Gly Ser
1               5                   10                  15

Ser Val Lys Val Ser Cys Lys Ala Ser Asp Phe Thr Phe Ser Asp Tyr
            20                  25                  30

Glu Ile His Trp Val Arg Gln Ala Pro Gly Gln Gly Leu Glu Trp Met
        35                  40                  45

Gly Leu Phe Asp Pro Glu Thr Gly Gly Ile Val Tyr Asn Gln Lys Phe
    50                  55                  60

Lys Gly Arg Val Thr Leu Thr Ala Asp Lys Ser Thr Ser Thr Ala Tyr

```
                65                  70                  75                  80
Met Glu Leu Ser Ser Leu Arg Ser Glu Asp Thr Ala Val Tyr Tyr Cys
                    85                  90                  95

Thr Arg Glu Gly Tyr Asn Arg Asp Trp Tyr Phe Asp Val Trp Gly Gln
                100                 105                 110

Gly Thr Thr Val Thr Val Ser Ser
        115                 120

<210> SEQ ID NO 38
<211> LENGTH: 120
<212> TYPE: PRT
<213> ORGANISM: Artificial sequence
<220> FEATURE:
<223> OTHER INFORMATION: Synthetic Sequence_Hu32VH4 sequence

<400> SEQUENCE: 38

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Asp Tyr
                20                  25                  30

Glu Ile His Trp Val Arg Gln Ala Pro Gly Gln Gly Leu Glu Trp Ile
            35                  40                  45

Gly Leu Phe Asp Pro Glu Thr Gly Gly Ile Val Tyr Asn Gln Lys Phe
        50                  55                  60

Lys Gly Arg Ala Thr Leu Thr Ala Asp Lys Ser Thr Ser Thr Ala Tyr
65                  70                  75                  80

Met Glu Phe Ser Ser Leu Arg Ser Glu Asp Thr Ala Val Tyr Tyr Cys
                    85                  90                  95

Thr Arg Glu Gly Tyr Asn Arg Asp Trp Tyr Phe Asp Val Trp Gly Gln
                100                 105                 110

Gly Thr Thr Val Thr Val Ser Ser
        115                 120

<210> SEQ ID NO 39
<211> LENGTH: 120
<212> TYPE: PRT
<213> ORGANISM: Artificial sequence
<220> FEATURE:
<223> OTHER INFORMATION: Synthetic Sequence_Hu32VH5 sequence

<400> SEQUENCE: 39

Glu Val Gln Leu Val Gln Ser Gly Ala Glu Val Lys Lys Pro Gly Ser
1               5                   10                  15

Ser Val Lys Val Ser Cys Lys Ala Ser Asp Phe Thr Phe Thr Asp Tyr
                20                  25                  30

Glu Ile His Trp Val Arg Gln Ala Pro Gly Gln Gly Leu Glu Trp Ile
            35                  40                  45

Gly Leu Phe Asp Pro Glu Thr Gly Gly Ile Val Tyr Asn Gln Lys Phe
        50                  55                  60

Lys Gly Arg Ala Thr Leu Thr Ala Asp Lys Ser Thr Ser Thr Ala Tyr
65                  70                  75                  80

Met Glu Phe Ser Ser Leu Arg Ser Glu Asp Thr Ala Val Tyr Tyr Cys
                    85                  90                  95

Thr Arg Glu Gly Tyr Asn Arg Asp Trp Tyr Phe Asp Val Trp Gly Gln
                100                 105                 110

Gly Thr Thr Val Thr Val Ser Ser
        115                 120
```

```
<210> SEQ ID NO 40
<211> LENGTH: 120
<212> TYPE: PRT
<213> ORGANISM: Artificial sequence
<220> FEATURE:
<223> OTHER INFORMATION: Synthetic Sequence_Hu32VH6 sequence

<400> SEQUENCE: 40

Glu Val Gln Leu Val Gln Ser Gly Ala Glu Val Lys Lys Pro Gly Ser
1               5                   10                  15

Ser Val Lys Val Ser Cys Lys Ala Ser Asp Phe Thr Phe Thr Asp Tyr
            20                  25                  30

Glu Ile His Trp Val Lys Gln Ala Pro Gly His Gly Leu Glu Trp Ile
        35                  40                  45

Gly Leu Phe Asp Pro Glu Thr Gly Gly Ile Val Tyr Asn Gln Lys Phe
    50                  55                  60

Lys Gly Lys Ala Thr Leu Thr Ala Asp Lys Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Thr Arg Glu Gly Tyr Asn Arg Asp Trp Tyr Phe Asp Val Trp Gly Gln
            100                 105                 110

Gly Thr Thr Val Thr Val Ser Ser
        115                 120

<210> SEQ ID NO 41
<211> LENGTH: 118
<212> TYPE: PRT
<213> ORGANISM: Artificial sequence
<220> FEATURE:
<223> OTHER INFORMATION: Synthetic Sequence_Hu33VH1/Hu33VH-CDR grafted
      sequence

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Gly Gly Gly Val Asp Thr Tyr Tyr Gln Asp Asn Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Gly His Gly Tyr Phe Asp Val Trp Gly Gln Gly Thr
            100                 105                 110

Thr Val Thr Val Ser Ser
        115

<210> SEQ ID NO 42
<211> LENGTH: 107
<212> TYPE: PRT
<213> ORGANISM: Artificial sequence
<220> FEATURE:
<223> OTHER INFORMATION: Synthetic Sequence_Hu33VL1/Hu33VL-CDR grafted
      sequence

<400> SEQUENCE: 42
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105
```

<210> SEQ ID NO 43
<211> LENGTH: 107
<212> TYPE: PRT
<213> ORGANISM: Artificial sequence
<220> FEATURE:
<223> OTHER INFORMATION: Synthetic Sequence_Hu33VL2 sequence

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Lys Val Glu Ile Lys
            100                 105
```

<210> SEQ ID NO 44
<211> LENGTH: 107
<212> TYPE: PRT
<213> ORGANISM: Artificial sequence
<220> FEATURE:
<223> OTHER INFORMATION: Synthetic Sequence_Hu33VL3 sequence

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Phe
            20                  25                  30

Leu Asn Trp Tyr Gln Gln Lys Pro Gly Gly Ala Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
```

```
                    85                  90                  95

Thr Phe Gly Gly Gly Thr Lys Val Glu Ile Lys
            100                 105

<210> SEQ ID NO 45
<211> LENGTH: 118
<212> TYPE: PRT
<213> ORGANISM: Artificial sequence
<220> FEATURE:
<223> OTHER INFORMATION: Synthetic Sequence_Hu33VH2 sequence

<400> SEQUENCE: 45

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Gly Gly Gly Val Asp Thr Tyr Tyr Gln Asp Asn Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Gly His Gly Tyr Phe Asp Val Trp Gly Gln Gly Thr
            100                 105                 110

Thr Val Thr Val Ser Ser
        115

<210> SEQ ID NO 46
<211> LENGTH: 118
<212> TYPE: PRT
<213> ORGANISM: Artificial sequence
<220> FEATURE:
<223> OTHER INFORMATION: Synthetic Sequence_Hu33VH3 sequence

<400> SEQUENCE: 46

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Gly Gly Gly Val Asp Thr Tyr Tyr Gln Asp Asn Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Gly His Gly Tyr Phe Asp Val Trp Gly Gln Gly Thr
            100                 105                 110

Thr Val Thr Val Ser Ser
        115

<210> SEQ ID NO 47
<211> LENGTH: 16
<212> TYPE: PRT
<213> ORGANISM: Artificial sequence
<220> FEATURE:
```

```
<223> OTHER INFORMATION: Synthetic Sequence_Hu23LCDR1(N33Q) sequence

<400> SEQUENCE: 47

Arg Ser Ser Gln Ser Leu Val His Ser Gln Gly Asn Thr Tyr Leu Glu
1               5                   10                  15

<210> SEQ ID NO 48
<211> LENGTH: 16
<212> TYPE: PRT
<213> ORGANISM: Artificial sequence
<220> FEATURE:
<223> OTHER INFORMATION: Synthetic Sequence_Hu23LCDR1(N33L) sequence

<400> SEQUENCE: 48

Arg Ser Ser Gln Ser Leu Val His Ser Leu Gly Asn Thr Tyr Leu Glu
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: Synthetic Sequence_Hu23LCDR1(N33T) sequence

<400> SEQUENCE: 49

Arg Ser Ser Gln Ser Leu Val His Ser Thr Gly Asn Thr Tyr Leu Glu
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: Synthetic Sequence_Hu23LCDR1(N33D) sequence

<400> SEQUENCE: 50

Arg Ser Ser Gln Ser Leu Val His Ser Asp Gly Asn Thr Tyr Leu Glu
1               5                   10                  15

<210> SEQ ID NO 51
<211> LENGTH: 16
<212> TYPE: PRT
<213> ORGANISM: Artificial sequence
<220> FEATURE:
<223> OTHER INFORMATION: Synthetic Sequence_Hu23LCDR1(G34A) sequence

<400> SEQUENCE: 51

Arg Ser Ser Gln Ser Leu Val His Ser Asn Ala Asn Thr Tyr Leu Glu
1               5                   10                  15

<210> SEQ ID NO 52
<211> LENGTH: 16
<212> TYPE: PRT
<213> ORGANISM: Artificial sequence
<220> FEATURE:
<223> OTHER INFORMATION: Synthetic Sequence_Hu23LCDR1(G34V) sequence

<400> SEQUENCE: 52

Arg Ser Ser Gln Ser Leu Val His Ser Asn Val Asn Thr Tyr Leu Glu
1               5                   10                  15

<210> SEQ ID NO 53
<211> LENGTH: 112
<212> TYPE: PRT
<213> ORGANISM: Artificial sequence
<220> FEATURE:
<223> OTHER INFORMATION: Synthetic Sequence_Hu23VL1(N33Q) sequence
```

<400> SEQUENCE: 53

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 54
<211> LENGTH: 112
<212> TYPE: PRT
<213> ORGANISM: Artificial sequence
<220> FEATURE:
<223> OTHER INFORMATION: Synthetic Sequence_Hu23VL1(N33L) sequence

<400> SEQUENCE: 54

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Leu Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 55
<211> LENGTH: 112
<212> TYPE: PRT
<213> ORGANISM: Artificial sequence
<220> FEATURE:
<223> OTHER INFORMATION: Synthetic Sequence_Hu23VL1(N33T) sequence

<400> SEQUENCE: 55

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Val Pro Tyr Thr Phe Gly Gly Gly Thr Lys Val Glu Ile Lys
            100                 105                 110

<210> SEQ ID NO 56
<211> LENGTH: 112
<212> TYPE: PRT
<213> ORGANISM: Artificial sequence
<220> FEATURE:
<223> OTHER INFORMATION: Synthetic Sequence_Hu23VL1(N33D) sequence

<400> SEQUENCE: 56

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Val Pro Tyr Thr Phe Gly Gly Gly Thr Lys Val Glu Ile Lys
            100                 105                 110

<210> SEQ ID NO 57
<211> LENGTH: 112
<212> TYPE: PRT
<213> ORGANISM: Artificial sequence
<220> FEATURE:
<223> OTHER INFORMATION: Synthetic Sequence_Hu23VL1(G34A) sequence

<400> SEQUENCE: 57

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Ala Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
            85                  90                  95

Ser His Val Pro Tyr Thr Phe Gly Gly Gly Thr Lys Val Glu Ile Lys
            100                 105                 110

<210> SEQ ID NO 58
<211> LENGTH: 112
<212> TYPE: PRT
<213> ORGANISM: Artificial sequence
<220> FEATURE:
<223> OTHER INFORMATION: Synthetic Sequence_Hu23VL1(G34V) sequence

<400> SEQUENCE: 58

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Val Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 59
<211> LENGTH: 112
<212> TYPE: PRT
<213> ORGANISM: Artificial sequence
<220> FEATURE:
<223> OTHER INFORMATION: Synthetic Sequence_Hu23VL2(N33Q) sequence

<400> SEQUENCE: 59

Asp Gly Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 60
<211> LENGTH: 112
<212> TYPE: PRT
<213> ORGANISM: Artificial sequence
<220> FEATURE:
<223> OTHER INFORMATION: Synthetic Sequence_Hu23VL2(N33L) sequence

<400> SEQUENCE: 60

Asp Gly Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Leu Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 61
<211> LENGTH: 112
<212> TYPE: PRT
<213> ORGANISM: Artificial sequence
<220> FEATURE:
<223> OTHER INFORMATION: Synthetic Sequence_Hu23VL2(N33T) sequence

<400> SEQUENCE: 61

Asp Gly Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Thr Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 62
<211> LENGTH: 112
<212> TYPE: PRT
<213> ORGANISM: Artificial sequence
<220> FEATURE:
<223> OTHER INFORMATION: Synthetic Sequence_Hu23VL2(N33D) sequence

<400> SEQUENCE: 62

Asp Gly Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 63
<211> LENGTH: 112
<212> TYPE: PRT
<213> ORGANISM: Artificial sequence
<220> FEATURE:
<223> OTHER INFORMATION: Synthetic Sequence_Hu23VL2(G34A) sequence

<400> SEQUENCE: 63

Asp Gly Val Met Thr Gln Thr Pro Leu Ser Leu Pro Val Thr Pro Gly
1               5                   10                  15

```
Glu Pro Ala Ser Ile Ser Cys Arg Ser Ser Gln Ser Leu Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110
```

<210> SEQ ID NO 64
<211> LENGTH: 112
<212> TYPE: PRT
<213> ORGANISM: Artificial sequence
<220> FEATURE:
<223> OTHER INFORMATION: Synthetic Sequence_Hu23VL2(G34V) sequence

<400> SEQUENCE: 64

```
Asp Gly Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Val Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110
```

<210> SEQ ID NO 65
<211> LENGTH: 5
<212> TYPE: PRT
<213> ORGANISM: Artificial sequence
<220> FEATURE:
<223> OTHER INFORMATION: Synthetic Sequence_Hu32 and Hu23 antibody HCDR1
      general formula sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 65

```
Asp Tyr Glu Xaa His
1               5
```

<210> SEQ ID NO 66
<211> LENGTH: 17
<212> TYPE: PRT
<213> ORGANISM: Artificial sequence
<220> FEATURE:
<223> OTHER INFORMATION: Synthetic Sequence_Hu32 and Hu23 antibody HCDR2
      general formula sequence
<220> FEATURE:
<221> NAME/KEY: misc_feature
<222> LOCATION: (2)..(2)
<223> OTHER INFORMATION: Xaa can be any naturally occurring amino acid

```
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 66

Leu Xaa Asp Pro Glu Thr Gly Gly Xaa Val Tyr Asn Gln Lys Phe Lys
1               5                   10                  15

Xaa

<210> SEQ ID NO 67
<211> LENGTH: 16
<212> TYPE: PRT
<213> ORGANISM: Artificial sequence
<220> FEATURE:
<223> OTHER INFORMATION: Synthetic Sequence_Hu32 and Hu23 antibody HCDR3
      general formula sequence
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid

<400> SEQUENCE: 67

Glu Xaa Xaa Xaa Xaa Tyr Xaa Xaa Xaa Xaa Asp Trp Tyr Phe Asp Val
1               5                   10                  15

<210> SEQ ID NO 68
<211> LENGTH: 16
<212> TYPE: PRT
<213> ORGANISM: Artificial sequence
<220> FEATURE:
<223> OTHER INFORMATION: Synthetic Sequence_Hu32 and Hu23 antibody LCDR1
      general formula sequence
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 68

Arg Ser Ser Gln Ser Xaa Val His Ser Xaa Xaa Xaa Thr Tyr Leu Glu
1               5                   10                  15

<210> SEQ ID NO 69
<211> LENGTH: 9
<212> TYPE: PRT
<213> ORGANISM: Artificial sequence
<220> FEATURE:
<223> OTHER INFORMATION: Synthetic Sequence_Hu32 and Hu23 antibody LCDR3
      general formula sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 69

Phe Gln Gly Ser His Val Pro Tyr Xaa
1               5
```

-continued

```
<210> SEQ ID NO 70
<211> LENGTH: 125
<212> TYPE: PRT
<213> ORGANISM: Artificial sequence
<220> FEATURE:
<223> OTHER INFORMATION: Synthetic Sequence_Hu32 and Hu23 antibody heavy
      chain variable region general formula sequence
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (66)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(103)
<223> OTHER INFORMATION: Xaa can be any naturally occurring amino acid
<220> FEATURE:
<221> NAME/KEY: misc_feature
<222> LOCATION: (105)..(108)
<223> OTHER INFORMATION: Xaa can be any naturally occurring amino acid

<400> SEQUENCE: 70

Glu Val Gln Leu Val Gln Ser Gly Ala Glu Val Lys Lys Pro Gly Ser
1               5                   10                  15

Ser Val Lys Val Ser Cys Lys Ala Ser Xaa Xaa Thr Phe Xaa Asp Tyr
            20                  25                  30

Glu Xaa His Trp Val Xaa Gln Ala Pro Gly Xaa Gly Leu Glu Trp Xaa
        35                  40                  45

Gly Leu Xaa Asp Pro Glu Thr Gly Gly Xaa Val Tyr Asn Gln Lys Phe
    50                  55                  60

Lys Xaa Xaa Xaa Thr Xaa Thr Ala Asp Lys Ser Thr Ser Thr Ala Tyr
```

```
                65                  70                  75                  80
Met Glu Xaa Ser Ser Leu Arg Ser Glu Asp Thr Ala Val Tyr Tyr Cys
                    85                  90                  95

Xaa Arg Glu Xaa Xaa Xaa Xaa Tyr Xaa Xaa Xaa Xaa Asp Trp Tyr Phe
                    100                 105                 110

Asp Val Trp Gly Gln Gly Thr Thr Val Thr Val Ser Ser
                115                 120                 125

<210> SEQ ID NO 71
<211> LENGTH: 112
<212> TYPE: PRT
<213> ORGANISM: Artificial sequence
<220> FEATURE:
<223> OTHER INFORMATION: Synthetic Sequence_Hu32 and Hu23 antibody light
      chain variable region general formula sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 71

Asp Xaa Val Met Thr Gln Thr Pro Leu Ser Leu Pro Val Thr Pro Gly
1               5                   10                  15

Glu Pro Ala Ser Ile Ser Cys Arg Ser Ser Gln Ser Xaa Val His Ser
                20                  25                  30

Xaa Xaa Xaa Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Xaa Phe Gly Gly Gly Thr Lys Val Glu Ile Lys
                100                 105                 110

<210> SEQ ID NO 72
<211> LENGTH: 327
<212> TYPE: PRT
<213> ORGANISM: Artificial sequence
<220> FEATURE:
<223> OTHER INFORMATION: Synthetic Sequence_IgG4-AA heavy chain constant
      region sequence

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45
```

```
Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 73
<211> LENGTH: 107
<212> TYPE: PRT
<213> ORGANISM: Artificial sequence
<220> FEATURE:
<223> OTHER INFORMATION: Synthetic Sequence_Antibody Kappa light chain
      constant region sequence

<400> SEQUENCE: 73

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 74
<211> LENGTH: 452
<212> TYPE: PRT
<213> ORGANISM: Artificial sequence
<220> FEATURE:
<223> OTHER INFORMATION: Synthetic Sequence_Hu23-11.IgG4AA antibody
      heavy chain sequence

<400> SEQUENCE: 74

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Glu Met His Trp Val Arg Gln Ala Pro Gly Gln Gly Leu Glu Trp Met
        35                  40                  45

Gly Leu Ile Asp Pro Glu Thr Gly Gly Thr Val Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Phe Ser Tyr Tyr Gly Ser Thr Ser Asp Trp Tyr Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser

```
                        325                 330                 335
Ile Glu Lys Thr Ile Ser Lys Ala Lys Gly Gln Pro Arg Glu Pro Gln
                340                 345                 350

Val Tyr Thr Leu Pro Pro Ser Gln Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys
        450

<210> SEQ ID NO 75
<211> LENGTH: 219
<212> TYPE: PRT
<213> ORGANISM: Artificial sequence
<220> FEATURE:
<223> OTHER INFORMATION: Synthetic
      Sequence_Hu23-11.IgG4AA/Hu32a-85.IgG4AA/Hu23-11.IgG4P/Hu32a-85.Ig
      G4P light chain sequence

<400> SEQUENCE: 75

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Thr Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 76
<211> LENGTH: 447
<212> TYPE: PRT
<213> ORGANISM: Artificial sequence
<220> FEATURE:
<223> OTHER INFORMATION: Synthetic Sequence_Hu32a-85.IgG4AA heavy chain
    sequence

<400> SEQUENCE: 76

Glu Val Gln Leu Val Gln Ser Gly Ala Glu Val Lys Lys Pro Gly Ser
1               5                   10                  15

Ser Val Lys Val Ser Cys Lys Ala Ser Asp Phe Thr Phe Thr Asp Tyr
            20                  25                  30

Glu Ile His Trp Val Lys Gln Ala Pro Gly His Gly Leu Glu Trp Ile
        35                  40                  45

Gly Leu Phe Asp Pro Glu Thr Gly Gly Ile Val Tyr Asn Gln Lys Phe
    50                  55                  60

Lys Gly Lys Ala Thr Leu Thr Ala Asp Lys Ser Thr Thr Ala Tyr
65                  70                  75                  80

Met Glu Phe Ser Ser Leu Arg Ser Glu Asp Thr Ala Val Tyr Tyr Cys
                85                  90                  95

Thr Arg Glu Gly Tyr Asn Arg Asp Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu

```
                355                 360                 365
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 77
<211> LENGTH: 445
<212> TYPE: PRT
<213> ORGANISM: Artificial sequence
<220> FEATURE:
<223> OTHER INFORMATION: Synthetic Sequence_Hu33-6.IgG4AA heavy chain
      sequence

<400> SEQUENCE: 77

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Gly Gly Gly Val Asp Thr Tyr Tyr Gln Asp Asn Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Gly His Gly Tyr Phe Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
            275                 280                 285
Pro Arg Glu Glu Gln Phe Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
            435                 440                 445
```

```
<210> SEQ ID NO 78
<211> LENGTH: 214
<212> TYPE: PRT
<213> ORGANISM: Artificial sequence
<220> FEATURE:
<223> OTHER INFORMATION: Synthetic Sequence_Hu33-6.IgG4AA/Hu33-6.IgG4P
      light chain sequence

<400> SEQUENCE: 78

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Asn Asn Phe
            20                  25                  30
Leu Asn Trp Tyr Gln Gln Lys Pro Gly Lys Ala Pro Lys Leu Leu Ile
        35                  40                  45
Tyr Tyr Thr Ser Ser Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Tyr Cys Gln Gln Gly Asn Thr Leu Pro Trp
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
    195                 200                 205

Phe Asn Arg Gly Glu Cys
    210

<210> SEQ ID NO 79
<211> LENGTH: 327
<212> TYPE: PRT
<213> ORGANISM: Artificial sequence
<220> FEATURE:
<223> OTHER INFORMATION: Synthetic Sequence_IgG4-P heavy chain constant
      region sequence

<400> SEQUENCE: 79

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys

<210> SEQ ID NO 80
<211> LENGTH: 452
<212> TYPE: PRT
<213> ORGANISM: Artificial sequence
<220> FEATURE:
<223> OTHER INFORMATION: Synthetic Sequence_Hu23-11. IgG4P antibody heavy chain sequence

<400> SEQUENCE: 80

```
Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asp Tyr
            20                  25                  30
Glu Met His Trp Val Arg Gln Ala Pro Gly Gln Gly Leu Glu Trp Met
        35                  40                  45
Gly Leu Ile Asp Pro Glu Thr Gly Gly Thr Val Tyr Asn Gln Lys Phe
    50                  55                  60
Lys Asp Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Arg Phe Ser Tyr Tyr Gly Ser Thr Ser Asp Trp Tyr Phe
            100                 105                 110
Asp Val Trp Gly Gln Gly Thr Thr Val Thr Val Ser Ser Ala Ser Thr
        115                 120                 125
Lys Gly Pro Ser Val Phe Pro Leu Ala Pro Cys Ser Arg Ser Thr Ser
    130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Leu Gly Thr Lys Thr Tyr Thr Cys
        195                 200                 205
Asn Val Asp His Lys Pro Ser Asn Thr Lys Val Asp Lys Arg Val Glu
    210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
```

```
Val Tyr Thr Leu Pro Pro Ser Gln Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 81
<211> LENGTH: 447
<212> TYPE: PRT
<213> ORGANISM: Artificial sequence
<220> FEATURE:
<223> OTHER INFORMATION: Synthetic Sequence_Hu32a-85.IgG4P heavy chain
      sequence

<400> SEQUENCE: 81

Glu Val Gln Leu Val Gln Ser Gly Ala Glu Val Lys Lys Pro Gly Ser
1               5                   10                  15

Ser Val Lys Val Ser Cys Lys Ala Ser Asp Phe Thr Phe Thr Asp Tyr
            20                  25                  30

Glu Ile His Trp Val Lys Gln Ala Pro Gly His Gly Leu Glu Trp Ile
        35                  40                  45

Gly Leu Phe Asp Pro Glu Thr Gly Gly Ile Val Tyr Asn Gln Lys Phe
    50                  55                  60

Lys Gly Lys Ala Thr Leu Thr Ala Asp Lys Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Thr Arg Glu Gly Tyr Asn Arg Asp Trp Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

Pro Glu Val Thr Cys Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 82
<211> LENGTH: 445
<212> TYPE: PRT
<213> ORGANISM: Artificial sequence
<220> FEATURE:
<223> OTHER INFORMATION: Synthetic Sequence_Hu33-6. IgG4P heavy chain
      sequence

<400> SEQUENCE: 82

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Thr Ile Ser Gly Gly Gly Val Asp Thr Tyr Tyr Gln Asp Asn Val
50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Tyr Gly His Gly Tyr Phe Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln

```
                    165                 170                 175
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445
```

ANTI-PD-1 ANTIBODY, ANTIGEN-BINDING FRAGMENT THEREOF AND PHARMACEUTICAL USE THEREOF

CROSS-REFERENCE TO RELATED APPLICATIONS

The present application is the national stage of International Patent Application No. PCT/CN2020/074098, filed on Jan. 31, 2020, which claims the benefit of and priority to Chinese Application No. CN201910108743.3, filed on Feb. 3, 2019, and Chinese Patent Application No. CN202010052351.2, filed Jan. 17, 2020, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 3, 2019, is named "719087CPUS 126268-5021 Sequence Listing.TXT" and is 95 kilobytes in size.

FIELD OF THE INVENTION

The present disclosure belongs to the field of biotechnology. More specifically, the present disclosure relates to anti-PD-1 antibodies and applications thereof.

BACKGROUND OF THE INVENTION

The statements herein only provide background information related to the present invention, and do not necessarily constitute prior art.

Tumor immunotherapy is a treatment method that fully utilizes and mobilizes the killer T cells in tumor patients to kill the tumor. At the same time, tumor cell evasion is a huge obstacle to tumor immunotherapy. Tumor cells use their own inhibitory effects on the immune system to promote the rapid growth of tumors. There is a very complicated relationship between the immune evasion mechanism of tumors and the immune response of the body to the tumors. In the early stage of tumor immunotherapy, tumor-specific killer T cells have their biological activity, but as the tumor grows, they lose their killing function in the later stage.

The activation of T cells in the human body adopts two signaling pathway systems. In addition to the first signal provided to T cells by the presentation of MHC-antigen peptides by antigen-presenting cells, a second signal provided by a series of co-stimulatory molecules is also required to allow T cells to produce normal immune responses. This dual-signaling pathway system plays a vital role in the balance of the immune system in the body. It strictly regulates different immune responses of the body to self and non-self antigens. If the second signal provided by the co-stimulatory molecule is absent, it will lead to a non-response or a sustained specific immune response of T cells, thus leading to tolerance. Therefore, the second signaling pathway plays a very critical regulatory role in the entire process of the immune response of the body.

Programmed death-1 (PD-1) is a protein receptor expressed on the surface of T cells discovered in 1992 and is involved in the process of cell apoptosis. PD-1 belongs to the CD28 family. It has 23% amino acid homology with cytotoxic T lymphocyte antigen 4 (CTLA-4), but its expression is different from that of CTLA, and it is mainly expressed on the activated T cells, B cells and myeloid cells. PD-1 has two ligands, PD-L1 and PD-L2, respectively. PD-L1 is mainly expressed on T cells, B cells, macrophages and dendritic cells (DCs), and the expression on cells can be up-regulated after being activated. The expression of PD-L2 is relatively constrained and is mainly expressed on antigen-presenting cells, such as the activated macrophages and dendritic cells.

PD-L1 inhibits the immune system by binding to PD-1 and B7-1. Many tumor cells and immune cells in the tumor tissue microenvironment express PD-L1. New research has found that high expression of PD-L1 protein was detected in breast cancer, lung cancer (for example, non-small cell lung cancer), gastric cancer, bowel cancer, kidney cancer, melanoma, colon cancer, bladder cancer, ovarian cancer, pancreatic cancer and liver cancer and other human tumor tissues, and the expression level of PD-L1 was closely related to the clinical manifestation and prognosis of patients.

Anti-PD-1 monoclonal antibody can maximize the patient's own immune system response to tumors by blocking the binding of PD-L1/PD-1, thus achieving the purpose of killing tumor cells. At present, the anti-PD-1 antibody Pembrolizumab (also known as Merck keytruda, keytruda, Merck-Pemb, Merck-keytruda, Merck-PD-1, pembrolizumab) and Novilumab (also known as BMS Opdivo, Opdivo, BMS-Nivolumab, Novilumab) has been approved by the FDA for the treatment of melanoma, Hodgkin's lymphoma patients, non-small cell lung cancer and other tumors. In addition, patent documents, such as WO200139722, WO2006121168, WO2010036959, WO2010089411, WO2011110604, WO2013173223, WO2013181634, US2014335093, U.S. Pat. No. 6,803,192B1, U.S. Pat. No. 8,617,546B2, and WO2015085847, also disclose a variety of anti-PD-1 monoclonal antibodies.

SUMMARY OF THE INVENTION

The present disclosure provides a new anti-PD-1 antibody, antigen-binding fragment thereof and medical use thereof.

In some alternative embodiments, the present disclosure provides an anti-PD-1 antibody or an antigen-binding fragment thereof, which is selected from any one of the following i) to iii):

i) an anti-PD-1 antibody or antigen-binding fragment thereof, the heavy chain variable region of which comprises HCDR1 as shown in SEQ ID NO: 8 or having at most 3, 2 or 1 amino acid mutation thereto, HCDR2 as shown in SEQ ID NO: 9 or having at most 3, 2, or 1 amino acid mutation thereto, and HCDR3 as shown in SEQ ID NO: 10 or having at most 8, 3, 2, or 1 amino acid mutation thereto; the light chain variable region of which comprises LCDR1 as shown in SEQ ID NO: 11 or having at most 4, 3, 2 or 1 amino acid mutation thereto, LCDR2 as shown in SEQ ID NO: 12 or having at most 3, 2 or 1 amino acid mutation thereto, and LCDR3 as shown in SEQ ID NO: 13 or having at most 3, 2 or 1 amino acid mutation thereto;

ii) an anti-PD-1 antibody or antigen-binding fragment thereof, the heavy chain variable region of which comprises HCDR1 as shown in SEQ ID NO: 14 or having at most 3, 2 or 1 amino acid mutation thereto, HCDR2 as shown in SEQ ID NO: 15 or having at most 3, 2, or 1 amino acid mutation thereto, and HCDR3 as shown in SEQ ID NO: 16 or having at most 8, 3, 2, or 1 amino acid mutation thereto; the light chain variable region of which comprises LCDR1 as shown in SEQ ID NO: 17 or having at most 4, 3, 2 or 1 amino acid mutation thereto, LCDR2 as shown in SEQ ID NO: 12 or having at most 3, 2 or 1 amino acid mutation thereto, and LCDR3 as shown in SEQ ID NO: 18 or having at most 3, 2 or 1 amino acid mutation thereto; and iii) an anti-PD-1 antibody or antigen-binding fragment thereof, the heavy chain variable region of which comprises HCDR1 as shown in SEQ ID NO: 21 or having at most 3, 2 or 1 amino acid mutation thereto, HCDR2 as shown in SEQ ID NO: 22 or having at most 3, 2, or 1 amino acid mutation thereto, and HCDR3 as shown in SEQ ID NO: 23 or having at most 3, 2, or 1 amino acid mutation thereto; the light chain variable region of which comprises LCDR1 as shown in SEQ ID NO: 24 or having at most 3, 2 or 1 amino acid mutation thereto, LCDR2 as shown in SEQ ID NO: 25 or having at most 3, 2 or 1 amino acid mutation thereto, and LCDR3 as shown in SEQ ID NO: 26 or having at most 3, 2 or 1 amino acid mutation thereto.

In some embodiments, the aforementioned anti-PD-1 antibody or antigen-binding fragment thereof of the present disclosure binds to human PD-1 with a dissociation equilibrium constant of $10^{-7}$M or less. In some embodiments, it binds to human PD-1 with a dissociation equilibrium constant of equal to or less than $10^{-8}$M, $10^{-9}$M, $10^{-10}$ M or $10^{-11}$ M.

In some alternative embodiments, the present disclosure provides an anti-PD-1 antibody or antigen-binding fragment thereof, the heavy chain variable region of which comprises: HCDR1 as shown in SEQ ID NO: 65, HCDR2 as shown in SEQ ID NO: 66, and HCDR3 as shown in SEQ ID NO: 67; the light chain variable region of which comprises: LCDR1 as shown in SEQ ID NO: 68, LCDR2 as shown in SEQ ID NO: 12, and LCDR3 as shown in SEQ ID NO: 69; the sequences are shown in Table 1 below:

wherein $X_{13}$ is selected from L, $X_{14}$ is selected from N, Q, L, T or D, $X_{15}$ is selected from G, A or V, and $X_{16}$ is selected from N.

In some alternative embodiments, the anti-PD-1 antibody or antigen-binding fragment thereof is selected from any one of the following (a) to (e):

(a) an anti-PD-1 antibody or antigen-binding fragment thereof, which comprises HCDR1, HCDR2 and HCDR3 as shown in SEQ ID NO: 8, SEQ ID NO: 9 and SEQ ID NO: 10, respectively, and LCDR2 and LCDR3 as shown in SEQ ID NO: 12 and SEQ ID NO: 13, respectively, and LCDR1 as shown in SEQ ID NO: 11, 47, 48, 49, 50, 51 or 52;

(b) an anti-PD-1 antibody or antigen-binding fragment thereof, which comprises HCDR1, HCDR2 and HCDR3 as shown in SEQ ID NO: 14, SEQ ID NO: 15 and SEQ ID NO: 16, respectively, and LCDR1, LCDR2 and LCDR3 as shown in SEQ ID NO: 17, SEQ ID NO: 12 and SEQ ID NO: 18, respectively;

(c) an anti-PD-1 antibody or antigen-binding fragment thereof, which comprises HCDR1, HCDR2 and HCDR3 as shown in SEQ ID NO: 21, SEQ ID NO: 22 and SEQ ID NO: 23, respectively, and LCDR1, LCDR2 and LCDR3 as shown in SEQ ID NO: 24, SEQ ID NO: 25 and SEQ ID NO: 26, respectively;

(d) an anti-PD-1 antibody or antigen-binding fragment thereof, which comprises HCDR1, HCDR2 and HCDR3 as shown in SEQ ID NO: 14, SEQ ID NO: 15 and SEQ ID NO: 16, respectively, and LCDR2 and LCDR3 as shown in SEQ ID NO: 12 and SEQ ID NO: 13, respectively, and LCDR1 as shown in SEQ ID NO: 11, 47, 48, 49, 50, 51 or 52; and

TABLE 1

| | Heavy chain | | Light chain |
|---|---|---|---|
| HCDR1 | DYE $X_1$H, $X_1$ is selected from I or M; (SEQ ID NO: 65) | LCDR1 | RSSQSX$_{13}$VHSX$_{14}$X$_{15}$X$_{16}$TYLE, wherein $X_{13}$ is selected from I or L, $X_{14}$ is selected from N, Q, L, T or D, $X_{15}$ is selected from G, A or V, and $X_{16}$ is selected from N or K; (SEQ ID NO: 68) |
| HCDR2 | LX$_2$DPETGGX$_3$VYNQKFKX$_4$, $X_2$ is selected from F or I, $X_3$ is selected from I/T and $X_4$ is selected from G or D; (SEQ ID NO: 66) | LCDR2 | KVSNRFS; (SEQ ID NO: 12) |
| HCDR3 | EX$_5$X$_6$X$_7$X$_8$YX$_9$X$_{10}$X$_{11}$X$_{12}$DWYFDV, $X_5$ is selected from G or R, $X_6$ is selected from F or absent, $X_7$ is S or absent, $X_8$ is Y or absent, $X_9$ is G or absent, $X_{10}$ is S or absent, $X_{11}$ is selected from N or T and $X_{12}$ is selected from R or S; (SEQ ID NO: 67) | LCDR3 | FQGSHVPYX$_{17}$, $X_{17}$ is selected from A or T; (SEQ ID NO: 69) |

In some alternative embodiments, in the aforementioned anti-PD-1 antibody or antigen-binding fragment thereof, the heavy chain variable region comprises HCDR1 as shown in SEQ ID NO: 8, HCDR2 as shown in SEQ ID NO: 9, and HCDR3 as shown in SEQ ID NO: 10; the light chain variable region comprises LCDR2 as shown in SEQ ID NO: 12, LCDR3 as shown in SEQ ID NO: 13, and LCDR1 as shown in the general formula RSSQSX$_{13}$VHSX$_{14}$X$_{15}$X$_{16}$TYLE (SEQ ID NO: 68), (e) the heavy chain variable region comprises HCDR1, HCDR2 and HCDR3 as shown in SEQ ID NO: 8, SEQ ID NO: 9 and SEQ ID NO: 10, respectively, and the light chain variable region comprises LCDR1, LCDR2 and LCDR3 as shown in SEQ ID NO: 17, SEQ ID NO: 12 and SEQ ID NO: 18, respectively.

In some embodiments, the anti-PD-1 antibody or antigen-binding fragment thereof comprises a heavy chain variable region and a light chain variable region, wherein the heavy chain variable region comprises HCDR1, HCDR2 and HCDR3 as shown in SEQ ID NO: 8, SEQ ID NO: 9 and SEQ ID NO: 10, respectively, and the light chain variable region comprises LCDR1, LCDR2 and LCDR3 as shown in SEQ ID NO: 49, SEQ ID NO: 12 and SEQ ID NO: 13, respectively.

In some embodiments, the anti-PD-1 antibody or antigen-binding fragment thereof comprises a heavy chain variable region and a light chain variable region, wherein the heavy chain variable region comprises HCDR1, HCDR2 and HCDR3 as shown in SEQ ID NO: 21, SEQ ID NO: 22 and SEQ ID NO: 23, respectively, and the light chain variable region comprises LCDR1, LCDR2 and LCDR3 as shown in SEQ ID NO: 24, SEQ ID NO: 25 and SEQ ID NO: 26, respectively.

In some alternative embodiments, the present disclosure provides an anti-PD-1 antibody or an antigen-binding fragment thereof, which is selected from any one of the following iv) to vi):
- iv) an anti-PD-1 antibody or antigen-binding fragment thereof, the heavy chain variable region of which comprises HCDR1, HCDR2 and HCDR3 with the same sequences as those of the heavy chain variable region shown in sequence SEQ ID NO: 4, and the light chain variable region comprises LCDR1, LCDR2 and LCDR3 with the same sequences as those of the light chain variable region shown in sequence SEQ ID NO: 5;
- v) an anti-PD-1 antibody or antigen-binding fragment thereof, the heavy chain variable region of which comprises HCDR1, HCDR2 and HCDR3 with the same sequences as those of the heavy chain variable region shown in sequence SEQ ID NO: 6, and the light chain variable region comprises LCDR1, LCDR2 and LCDR3 with the same sequences as those of the light chain variable region shown in sequence SEQ ID NO: 7; and
- vi) an anti-PD-1 antibody or antigen-binding fragment thereof, the heavy chain variable region of which comprises HCDR1, HCDR2 and HCDR3 with the same sequences as those of the heavy chain variable region shown in sequence SEQ ID NO: 19, and the light chain variable region comprises LCDR1, LCDR2 and LCDR3 with the same sequences as those of the light chain variable region shown in sequence SEQ ID NO: 20.

In some embodiments of the aforementioned anti-PD-1 antibody or antigen-binding fragment thereof, the anti-PD-1 antibody or antigen-binding fragment thereof is a murine antibody or antigen-binding fragment thereof, a chimeric antibody or antigen-binding fragment thereof, a fully human antibody or antigen-binding fragment thereof, or a humanized antibody or antigen-binding fragment thereof.

In some embodiments of the aforementioned anti-PD-1 antibody or antigen-binding fragment thereof, the anti-PD-1 antibody or antigen-binding fragment thereof is a humanized antibody or antigen-binding fragment thereof.

In some embodiments, the humanized antibody comprises a framework region derived from a human antibody or a framework region variant thereof.

In some embodiments, the framework region variant has at most 11 amino acid back mutations on each of the light chain framework region and/or the heavy chain framework region of a human antibody.

In some embodiments, the framework region variant comprises mutation(s) selected from any one of the following (f) to (h):

- (f) 2G amino acid back mutation comprised in the light chain variable region and/or one or more amino acid back mutations selected from 27Y, 48I, 67T, 69L, 82F and 93T comprised in the heavy chain variable region;
- (g) 2V amino acid back mutation comprised in the light chain variable region, and/or one or more amino acid back mutations selected from 26D, 27F, 30T, 38K, 43H, 48I, 66K, 67A, 69L, 82F and 93T comprised in the heavy chain variable region; and
- (h) one or more amino acid back mutations selected from 42G, 44V and 71Y comprised in the light chain variable region, and/or 1K and/or 94S amino acid back mutations comprised in the heavy chain variable region.

In some embodiments of the aforementioned anti-PD-1 antibody or antigen-binding fragment thereof, the anti-PD-1 antibody or antigen-binding fragment thereof comprises antibody variable regions selected from the group consisting of:

- (a2) a heavy chain variable region comprising HCDR1, HCDR2 and HCDR3 as shown in SEQ ID NO: 8, SEQ ID NO: 9 and SEQ ID NO: 10, respectively, and one or more amino acid back mutations of 27Y, 48I, 67T, 69L, 82F and 93T comprised in the heavy chain framework region, and
a light chain variable region comprising LCDR2 and LCDR3 as shown in SEQ ID NO: 12 and SEQ ID NO: 13, respectively, and LCDR1 as shown in SEQ ID NO: 11, 47, 48, 49, 50, 51 or 52, and 2G amino acid back mutation comprised in the light chain framework region;
- (b2) a heavy chain variable region comprising HCDR1, HCDR2 and HCDR3 as shown in SEQ ID NO: 14, SEQ ID NO: 15 and SEQ ID NO: 16, respectively, and one or more amino acid back mutations selected from 26D, 27F, 30T, 38K, 43H, 48I, 66K, 67A, 69L, 82F and 93T comprised in the heavy chain variable region; and
a light chain variable region comprising LCDR1, LCDR2 and LCDR3 as shown in SEQ ID NO: 17, SEQ ID NO: 12 and SEQ ID NO: 18, respectively, and 2V amino acid back mutation comprised in the light chain framework region;
- (c2) a heavy chain variable region comprising HCDR1, HCDR2 and HCDR3 as shown in SEQ ID NO: 21, SEQ ID NO: 22 and SEQ ID NO: 23, respectively, and 1K and/or 94S amino acid back mutations comprised in the heavy chain framework region, and
a light chain variable region comprising LCDR1, LCDR2 and LCDR3 as shown in SEQ ID NO: 24, SEQ ID NO: 25 and SEQ ID NO: 26, respectively, and one or more amino acid back mutations selected from 42G, 44V and 71Y comprised in the light chain framework region.

In some embodiments of the aforementioned anti-PD-1 antibody or antigen-binding fragment thereof, the anti-PD-1 antibody or antigen-binding fragment thereof comprises antibody variable regions selected from any one of the following (i) to (o):

- (i) a heavy chain variable region, the sequence of which is as shown in SEQ ID NO: 4 or has at least 90% sequence identity with SEQ ID NO: 4, and/or a light chain variable region, the sequence of which is as shown in SEQ ID NO: 5 or has at least 90% sequence identity with SEQ ID NO: 5;
- (j) a heavy chain variable region, the sequence of which is as shown in SEQ ID NO: 6 or has at least 90% sequence identity with SEQ ID NO: 6, and/or a light chain variable region, the sequence of which is as shown in SEQ ID NO: 7 or has at least 90% sequence identity with SEQ ID NO: 7;

wherein the sequences SEQ ID NO: 70 and SEQ ID NO: 71 are represented by general formula sequences as shown in Table 2:

TABLE 2

| |  |
|---|---|
| EVQLVQSGAEVKKPGSSVKVSCKAS$X_{18}X_{19}$TF$X_{20}$D YE$X_1$HWV$X_{21}$QAPG$X_{22}$GLEW$X_{23}$GL$X_2$DPETGG$X_3$V YNQKFK$X_4X_{24}X_{25}$T$X_{26}$TADKSTSTAYME$X_{27}$SSLRS EDTAVYYC$X_{28}$RE$X_5X_6X_7X_8$Y$X_9X_{10}X_{11}X_{12}$DWYFDV WGQGTTVTVSS, wherein, $X_1$ is selected from I or M, $X_2$ is selected from F or I, $X_3$ is selected from I/T, $X_4$ is selected from G or D, $X_5$ is selected from G or R, $X_6$ is F or absent, $X_7$ is S or absent, $X_8$ is Y or absent, $X_9$ is G or absent, $X_{10}$ is S or absent, $X_{11}$ is selected from N or T, $X_{12}$ is selected from R or S, $X_{18}$ is selected from G or D, $X_{19}$ is selected from G, F or Y, $X_{20}$ is selected from S or T, $X_{21}$ is selected from R or K, $X_{22}$ is selected from Q or H, $X_{23}$ is selected from M or I, $X_{24}$ is selected from R or K, $X_{25}$ is selected from V, A or T, $X_{26}$ is selected from R or K, $X_{27}$ is selected from L or F and $X_{28}$ is selected from A or T (SEQ ID NO: 70) | D$X_{29}$VMTQTPLSLPVTP GEPASISCRSSQS$X_{13}$VH S$X_{14}X_{15}X_{16}$TYLEWYLQ KPGQSPQLLIYKVSNRF SGVPDRFSGSGSGTDFT LKISRVEAEDVGVYYC FQGSHVPY$X_{17}$FGGGTK VEIK, wherein, $X_{13}$ is selected from I or L, $X_{14}$ is selected from N, Q, L, T or D, $X_{15}$ is selected from G, A or V, $X_{16}$ is selected from N or K, $X_{17}$ is selected from A or T and $X_{29}$ is selected from I, V or G (SEQ ID NO: 71) |

(k) a heavy chain variable region, the sequence of which is as shown in SEQ ID NO: 19 or has at least 90% sequence identity with SEQ ID NO: 19, and/or a light chain variable region, the sequence of which is as shown in SEQ ID NO: 20 or has at least 90% sequence identity with SEQ ID NO: 20;

(l) a heavy chain variable region, the sequence of which is as shown in SEQ ID NO: 27, 30, 31 or 32, or has at least 90% sequence identity with SEQ ID NO: 27, 30, 31 or 32, respectively, and/or
a light chain variable region, the sequence of which is as shown in SEQ ID NO: 28, 29, 53, 54, 55, 56, 57, 58, 59, 60, 61, 62, 63 or 64, or has at least 90% sequence identity with SEQ ID NO: 28, 29, 34, 35, 53, 54, 55, 56, 57, 58, 59, 60, 61, 62, 63 or 64, respectively;

(m) a heavy chain variable region, the sequence of which is as shown in SEQ ID NO: 33, 36, 37, 38, 39 or 40, or has at least 90% sequence identity with SEQ ID NO: 33, 36, 37, 38, 39 or 40, respectively, and/or
a light chain variable region, the sequence of which is as shown in SEQ ID NO: 34, 35, 28, 29, 53, 54, 55, 56, 57, 58, 59, 60, 61, 62, 63 or 64, or has at least 90% sequence identity with SEQ ID NO: 34, 35, 28, 29, 53, 54, 55, 56, 57, 58, 59, 60, 61, 62, 63 or 64, respectively;

(n) a heavy chain variable region, the sequence of which is as shown in SEQ ID NO: 41, 45 or 46, or has at least 90% sequence identity with SEQ ID NO: 41, 45 or 46, respectively, and/or
a light chain variable region, the sequence of which is as shown in SEQ ID NO: 42, 43 or 44, or has at least 90% sequence identity with SEQ ID NO: 42, 43 or 44, respectively;

(o) a heavy chain variable region, the sequence of which is as shown in SEQ ID NO: 70 or has at least 90% sequence identity with SEQ ID NO: 70, and/or
a light chain variable region, the sequence of which is as shown in SEQ ID NO: 71 or has at least 90% sequence identity with SEQ ID NO: 71; and (p) a heavy chain variable region, the sequence of which is as shown in SEQ ID NO: 27, 30, 31 or 32, or has at least 90% sequence identity with SEQ ID NO: 27, 30, 31 or 32, respectively, and/or
a light chain variable region, the sequence of which is as shown in SEQ ID NO: 34 or 35, or has at least 90% sequence identity with SEQ ID NO: 34 or 35, respectively;

In some embodiments, the heavy chain variable region of the anti-PD-1 antibody is as shown in SEQ ID NO: 27 or has at least 90% identity with SEQ ID NO: 27, and the light chain variable region sequence of the anti-PD-1 antibody is as shown in SEQ ID NO: 55 or has at least 90% sequence identity with SEQ ID NO: 55.

In some embodiments, the heavy chain variable region of the anti-PD-1 antibody is as shown in SEQ ID NO: 46 or has at least 90% identity with SEQ ID NO: 46, and the light chain variable region sequence of the anti-PD-1 antibody is as shown in SEQ ID NO: 43 or has at least 90% sequence identity with SEQ ID NO: 43.

The aforementioned "at least 90% identity" includes having at least 90%, 91%, 92%, 93%, 94%, 95%, 96%, 97%, 98%, 99% or 100% identity.

In some other embodiments of the aforementioned anti-PD-1 antibody or antigen-binding fragment thereof, the antibody further comprises antibody constant regions; in some other embodiments, the heavy chain constant region of the antibody constant region is selected from human IgG1, IgG2, IgG3 and IgG4 constant regions and conventional variants thereof, the light chain constant region of the antibody constant region is selected from human antibody κ and λ chain constant regions and conventional variants thereof; in some other embodiments, the antibody constant regions comprise an IgG4 heavy chain constant region into which one or more mutations of S228P, F234A and L235A are introduced, for example, comprise an IgG4 heavy chain constant region having the three amino acid mutations of S228P, F234A and L235A; in some other embodiments, the antibody comprises a heavy chain constant region as shown in SEQ ID NO: 72 or SEQ ID NO: 79, and a light chain constant region as shown in SEQ ID NO: 73.

In some embodiments of the aforementioned anti-PD-1 antibody or antigen-binding fragment thereof, the anti-PD-1 antibody comprises a light chain as shown in SEQ ID NO: 78 and a heavy chain as shown in SEQ ID NO: 77 or 82; or
  a light chain as shown in SEQ ID NO: 75 and a heavy chain as shown in SEQ ID NO: 74, 76, 80 or 81.

In some embodiments, the anti-PD-1 antibody comprises:
  a heavy chain as shown in SEQ ID NO: 74 and a light chain as shown in SEQ ID NO: 75; or
  a heavy chain as shown in SEQ ID NO: 77 and a light chain as shown in SEQ ID NO: 78.

In some embodiments, provided is an anti-PD-1 antibody or an antigen-binding fragment thereof, the antibody competitively binding to human PD-1 or binding to the same human PD-1 epitope with any one of the aforementioned anti-PD-1 antibodies or antigen-binding fragments thereof.

In some embodiments of the aforementioned anti-PD-1 antibody or antigen-binding fragment thereof, the antibody is a bispecific antibody or a multispecific antibody.

In some embodiments of the anti-PD-1 antibody or antigen-binding fragment thereof, the antigen-binding fragment is selected from the group consisting of Fab, Fab', F(ab)$_2$, single-chain antibody (scFv), dimerized V region (diabody) and disulfide bond stabilized V region (dsFv).

In some embodiments, disclosed is an isolated monoclonal antibody or antigen-binding fragment thereof, said antibody competitively binding to human PD-1 with the anti-PD-1 antibody or antigen-binding fragment thereof according to any one of the foregoing.

In some embodiments, the present disclosure also provides a pharmaceutical composition, which comprises a therapeutically effective amount of the anti-PD-1 antibody or antigen-binding fragment thereof according to any one of the foregoing, or a therapeutically effective amount of the aforementioned isolated monoclonal antibody or antigen-binding fragment thereof, and one or more pharmaceutically acceptable carriers, diluents, buffers or excipients. In some embodiments, the therapeutically effective amount refers to a unit dose of the composition containing 0.1 to 3000 mg of the aforementioned anti-PD-1 antibody or antigen-binding fragment thereof.

In some embodiments, the present disclosure also provides a nucleic acid molecule that encodes the anti-PD-1 antibody or antigen-binding fragment thereof according to any one of the foregoing, or encodes the aforementioned isolated monoclonal antibody or antigen-binding fragment thereof.

In some embodiments, the present disclosure also provides a host cell comprising the aforementioned nucleic acid molecule.

In some embodiments, the present disclosure also provides a method for immunodetection or determination of PD-1, which comprises a step of using the anti-PD-1 antibody or antigen-binding fragment thereof according to any one of the foregoing, or a step of using the aforementioned isolated monoclonal antibody or antigen-binding fragment thereof.

In some embodiments, the present disclosure also provides a kit comprising the aforementioned anti-PD-1 antibody or antigen-binding fragment thereof or the aforementioned isolated monoclonal antibody or antigen-binding fragment thereof.

In some embodiments, provided is use of the aforementioned anti-PD-1 antibody or antigen-binding fragment thereof in preparing diagnostic agents for PD-1 related diseases.

In some embodiments, the present disclosure also provides a method for treating diseases, which comprises administering to a subject a therapeutically effective amount of the anti-PD-1 antibody or antigen-binding fragment thereof according to any one of the foregoing, or the aforementioned isolated monoclonal antibody or antigen-binding fragment thereof, or the aforementioned pharmaceutical composition, or the aforementioned nucleic acid molecule.

In some embodiments, the disease is tumor.

In some other embodiments, the disease is selected from: head and neck squamous cell carcinoma, head and neck cancer, brain cancer, glioma, glioblastoma multiforme, neuroblastoma, central nervous system cancer, neuroendocrine tumor, pharyngeal cancer, nasopharyngeal cancer, esophageal cancer, thyroid cancer, malignant pleural mesothelioma, lung cancer, breast cancer, liver cancer, hepatoma, hepatocellular carcinoma, hepatobiliary cancer, pancreatic cancer, gastric cancer, gastrointestinal cancer, bowel cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative neoplasm, squamous cell carcinoma, Ewing's sarcoma, systemic light chain amyloidosis and Merkel cell carcinoma; in some of these embodiments, the lymphoma is selected from: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, T-cell/histiocyte rich large B-cell lymphoma and lymphoplasmacytic lymphoma, the lung cancer is selected from: non-small cell lung cancer and small cell lung cancer, the leukemia is selected from: chronic myeloid leukemia, acute myeloid leukemia, lymphocytic leukemia, lymphoblastic leukemia, acute lymphoblastic leukemia, chronic lymphocytic leukemia and myeloid leukemia; in some other embodiments, the disease is selected from: PD-L1 positive melanoma, lung cancer, non-small cell lung cancer, breast cancer, gastric cancer, kidney cancer, bladder cancer, bowel cancer and colon cancer.

In some embodiments, the present disclosure also provides use of the anti-PD-1 antibody or antigen-binding fragment thereof according to any one of the foregoing, or the aforementioned isolated monoclonal antibody or antigen-binding fragment thereof, or the aforementioned pharmaceutical composition, or the aforementioned nucleic acid molecule, in preparing medicaments for the treatment or prevention of diseases.

In some embodiments, the disease is tumor.

In some other embodiments, the disease is selected from: head and neck squamous cell carcinoma, head and neck cancer, brain cancer, glioma, glioblastoma multiforme, neuroblastoma, central nervous system cancer, neuroendocrine tumor, pharyngeal cancer, nasopharyngeal cancer, esophageal cancer, thyroid cancer, malignant pleural mesothelioma, lung cancer, breast cancer, liver cancer, hepatoma, hepatocellular carcinoma, hepatobiliary cancer, pancreatic cancer, gastric cancer, gastrointestinal cancer, bowel cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative neoplasm, squamous cell carcinoma, Ewing's sarcoma, systemic light chain amyloidosis and Merkel cell carcinoma; in some of these embodiments, the lymphoma is selected from: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, T-cell/histiocyte rich large B-cell lymphoma and lymphoplasmacytic lymphoma, the lung cancer is selected from: non-small cell lung cancer and small cell lung cancer, the leukemia is selected from: chronic myeloid leukemia, acute myeloid leukemia, lymphocytic leukemia, lymphoblastic leukemia, acute lymphoblastic leukemia, chronic lymphocytic leukemia and myeloid leukemia; in some other embodiments, the disease is selected from: PD-L1 positive melanoma, lung cancer, non-small cell lung cancer, breast cancer, gastric cancer, kidney cancer, bladder cancer, bowel cancer and colon cancer.

In some embodiments, the present disclosure also provides the anti-PD-1 antibody or antigen-binding fragment thereof according to any one of the foregoing, or the aforementioned isolated monoclonal antibody or antigen-binding fragment thereof, or the aforementioned nucleic acid molecule, or the aforementioned pharmaceutical composition, for use as medicaments.

In some embodiments, the medicament is used for the treatment or prevention of PD-1 related diseases.

In some embodiments, the disease is tumor.

In some other embodiments, the disease is selected from: head and neck squamous cell carcinoma, head and neck cancer, brain cancer, glioma, glioblastoma multiforme, neuroblastoma, central nervous system cancer, neuroendocrine tumor, pharyngeal cancer, nasopharyngeal cancer, esophageal cancer, thyroid cancer, malignant pleural mesothelioma, lung cancer, breast cancer, liver cancer, hepatoma, hepatocellular carcinoma, hepatobiliary cancer, pancreatic cancer, gastric cancer, gastrointestinal cancer, bowel cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative neoplasm, squamous cell carcinoma, Ewing's sarcoma, systemic light chain amyloidosis and Merkel cell carcinoma; in some of these embodiments, the lymphoma is selected from: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, T-cell/histiocyte rich large B-cell lymphoma and lymphoplasmacytic lymphoma, the lung cancer is selected from: non-small cell lung cancer and small cell lung cancer, the leukemia is selected from: chronic myeloid leukemia, acute myeloid leukemia, lymphocytic leukemia, lymphoblastic leukemia, acute lymphoblastic leukemia, chronic lymphocytic leukemia and myeloid leukemia; in some other embodiments, the disease is selected from: PD-L1 positive melanoma, lung cancer, non-small cell lung cancer, breast cancer, gastric cancer, kidney cancer, bladder cancer, bowel cancer and colon cancer.

DETAILED DESCRIPTION OF THE INVENTION

Overview

Figure 1:
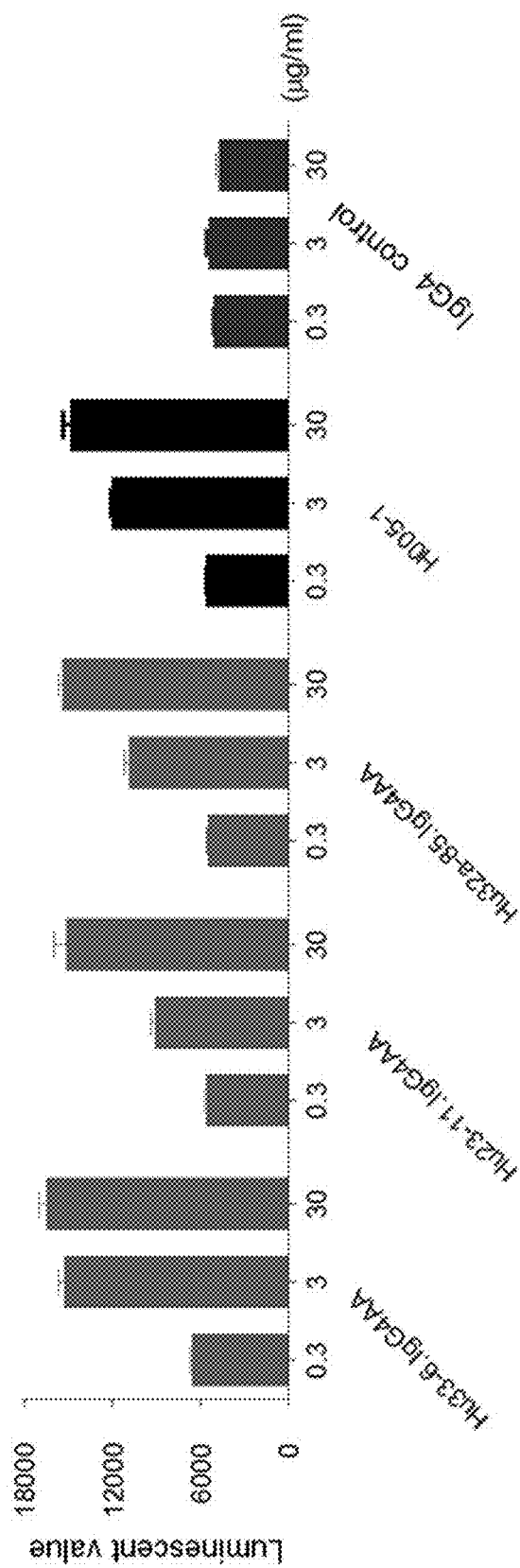
FIG. 1: the test results of anti-PD-1 antibodies blocking the binding of PD-1 to its ligand.

To make the present disclosure be understood easier, certain technical and scientific terms are specifically defined below. Unless clearly defined otherwise herein, all other technical and scientific terms used herein have the meanings commonly understood by those of ordinary skill in the art to which the present disclosure belongs.

The terms "programmed death 1", "programmed cell death 1", "protein PD-1", "PD-1", "PDCD1" and "hPD-1" are used interchangeably and include human PD-1 variants, isotypes, species homologs, and analogs that have at least one epitope in common with PD-1. The complete PD-1 sequence can be found with GenBank accession number U64863.

The term "programmed death ligand-1 (PD-L1)" is one of the two cell surface glycoprotein ligands of PD-1 (the other is PD-L2), which down-regulates T cell activation and cytokine secretion when it binds to PD-1. The term "PD-L1" as used herein includes human PD-L1 (hPD-L1), hPD-L1 variants, isotypes and interspecies homologs, and 5 analogs that have at least one epitope in common with hPD-1. The complete hPD-L1 sequence can be found with GenBank accession number Q9NZQ7.

The term "cytokine" is a general term for proteins released by a population of cells and acting on other cells as intercellular mediators. Examples of such cytokines include lymphokines, monokines, chemokines and traditional polypeptide hormones. Exemplary cytokines include: human IL-2, IFN-γ, IL-6, TNFα, IL-17 and IL-5.

The three-letter codes and one-letter codes of amino acids used in the present disclosure are as described in J. biol. chem, 243, p 3558 (1968).

The "antibody" described in the present disclosure refers to an immunoglobulin generally. A natural intact antibody is a tetrapeptide chain structure composed of two identical heavy chains and two identical light chains linked by interchain disulfide bonds. The amino acid compositions and sequences of the immunoglobulin heavy chain constant regions are different, so their antigenicity is also different. Thereby, immunoglobulins can be divided into five classes, or named as isotypes of immunoglobulins, namely IgM, IgD, IgG, IgA and IgE, and their corresponding heavy chains are μ chain, δ chain, γ chain, α chain and ε chain, respectively. The same class of Ig can be divided into different subclasses according to the difference in the amino acid composition of the hinge region and the number and position of heavy chain disulfide bonds. For example, IgG can be divided into IgG1, IgG2, IgG3 and IgG4. The light chain is divided into κ chain or λ chain by the difference of the constant region. Each of the five classes of Ig can have a κ chain or a λ chain. The antibodies referred to in the present disclosure include antibodies or antigen-binding fragments thereof, including antibodies or antigen-binding fragments thereof that have been modified on the basis of immunoglobulin while retaining the ability to bind antigen; including monospecific antibodies, bispecific antibodies or multispecific antibodies; also including monovalent antibodies, bivalent antibodies or multivalent antibodies. Antigen-binding fragments of antibodies, for example, can be those comprising at least one VH-CH1 and at least one VL-CL structure, in which the VH and VL structures can approach to each other based on the interchain interaction and retain antigen binding ability. In some embodiments, the antigen-binding fragment of the antibody is a monovalent Fab fragment (Fab 1 fragment), bivalent Fab fragment (F(ab)2), trivalent Fab fragment (F(ab)3), multivalent (two or more) Fab fragment, and can also be other monospecific, bispecific or multispecific antigen binding fragments comprising at least one Fab fragment.

"Bispecific antibody" refers to an antibody (including antibody or antigen-binding fragment thereof, such as single-chain antibody) that can specifically bind to two different antigens or two different epitopes of the same antigen. The prior art has disclosed bispecific antibodies with various structures. According to the integrity of the IgG molecule, they can be divided into IgG-like bispecific antibodies and antibody fragment-type bispecific antibodies. According to the number and configuration of the antigen binding regions, they can be divided into bivalent, trivalent, tetravalent or more-valent bispecific antibodies. According to whether the structure is symmetric, they can be divided into symmetric structure bispecific antibodies and asymmetric structure bispecific antibodies. Among them, antibody fragment-based bispecific antibodies, for example Fab fragments lacking Fc fragment, form bispecific antibodies by binding two or more Fab fragments in one molecule. These antibodies have lower immunogenicity and smaller molecular weight and higher tumor tissue permeability. Typical antibody structures of this type are bispecific antibodies such as F(ab)2, scFv-Fab, (scFv)2-Fab, etc.; For IgG-like bispecific antibodies (for example with Fc fragment), this type of antibody has larger molecular weight. The Fc fragment helps the purification of the antibody in later stages and improves its solubility and stability. The Fc moiety may also bind to the receptor FcRn and increase the serum half-life of the antibody. Typical bispecific antibody structure models are such as KiH, CrossMAb, Triomab quadroma, FcΔAdp, ART-Ig, BiMAb, Biclonics, BEAT, DuoBody, Azymetric, XmAb, 2:1 TCBs, 1Fab-IgG TDB, FynomAb, two-in-one/DAF, scFv-Fab-IgG, DART-Fc, LP-DART, CODV-Fab-TL, HLE-BiTE, F(ab)2-CrossMAb, IgG-(scFv)2, Bs4Ab, DVD-Ig, Tetravalent-DART-Fc, (scFv)4-Fc, CODV-Ig, mAb2, F(ab)4-CrossMAb and other bispecific antibodies (see Aran F. Labrijn et al., Nature Reviews Drug Discovery volume 18, pages 585-608 (2019); Chen S1 et al., J Immunol Res. 2019 Feb. 11; 2019:4516041).

The term "monovalent", "bivalent", "trivalent" or "multivalent" refers to the presence of a specified number of antigen binding sites in an antibody or polypeptide complex. For example "monovalent antibody" means that there is one antigen binding site in the antibody, "Monovalent polypeptide complex" means that there is one antigen binding site in the polypeptide complex; "Bivalent antibody" means that there are two antigen binding sites in the antibody, "Bivalent polypeptide complex" means that there are two antigen binding sites in the polypeptide complex; "Trivalent antibody" means that there are three antigen binding sites in the antibody, "Trivalent polypeptide complex" means that there are three antigen binding sites in the polypeptide complex; "Multivalent antibody" means that there are multiple (three or more) antigen binding sites in the antibody, and "Multivalent polypeptide complex" means that there are multiple (two or more) antigen binding sites in the polypeptide complex.

The term "antibody fusion protein" refers to a biologically active fusion protein formed by linking a protein of interest (polypeptide) with an immunoglobulin. The fusion protein has the biological activity both of the linked protein and of the immunoglobulin.

The sequence of about 110 amino acids near the N-terminus of the antibody heavy and light chain varies greatly and is the variable region (Fv region); the remaining amino acid sequence near the C-terminus is relatively stable and is the constant region. The variable region includes 3 hypervariable regions (HVRs) and 4 framework regions (FRs) with relatively conservative sequences. The 3 hypervariable regions which determine the specificity of the antibody are also known as complementarity determining regions (CDRs). Each of the light chain variable region (VL) and heavy chain variable region (VH) consists of 3 CDR regions and 4 FR regions. The order from the amino terminus to the carboxyl terminus is: FR1, CDR1, FR2, CDR2, FR3, CDR3, FR4. The 3 CDR regions of the light chain refer to LCDR1, LCDR2 and LCDR3; and the 3 CDR regions of the heavy chain refer to HCDR1, HCDR2 and HCDR3.

The antibodies of the present disclosure include murine antibodies, chimeric antibodies, humanized antibodies and fully human antibodies, preferably humanized antibodies.

The term "murine antibody" in the present disclosure is a monoclonal antibody against human PD-1 prepared according to the knowledge and skills in the art. During preparation, the test subject is injected with PD-1 antigen, and then hybridomas expressing antibodies with the desired sequence or functional properties are isolated. In a preferred embodiment of the present disclosure, the murine anti-PD-1 antibody or antigen-binding fragment thereof can further comprise the light chain constant region of murine κ, λ chain or variant thereof, or further comprise the heavy chain constant region of murine IgG1, IgG2, IgG3 or variant thereof.

The term "chimeric antibody" is an antibody formed by fusing the variable region of a murine antibody with the constant region of a human antibody, which can alleviate the immune response induced by murine antibody. Establishing a chimeric antibody requires first establishing a hybridoma secreting murine specific monoclonal antibodies, then cloning the variable region gene from the murine hybridoma cells, and then cloning the constant region gene of the human antibody as necessary, linking the murine variable region gene with the human constant region gene to form a chimeric gene, inserting the chimeric gene into an expression vector, and finally expressing the chimeric antibody molecule in a eukaryotic system or a prokaryotic system. In a preferred embodiment of the present disclosure, the antibody light chain of the PD-L1 chimeric antibody further comprises a light chain constant region of a human κ, λ chain or variant thereof. The antibody heavy chain of the PD-1 chimeric antibody further comprises the heavy chain constant region of human IgG1, IgG2, IgG3, IgG4 or variant thereof, preferably comprises the heavy chain constant region of human IgG1, IgG2 or IgG4, or comprises IgG1, IgG2, or IgG4 variants with amino acid mutations (for example L234A and/or L235A mutations, and/or S228P mutations).

The term "humanized antibody", also known as CDR-grafted antibody, refers to an antibody produced by grafting murine CDR sequences into the framework of human antibody variable regions, that is, refers to an antibody produced in different types of human germline antibody framework sequences. It can overcome the heterogeneous reaction induced by the chimeric antibody as it carries a large amount of murine protein components. Such framework sequences can be obtained from public DNA databases or published references that include germline antibody gene sequences. For example, the germline DNA sequences of the human heavy chain and light chain variable region genes can be found in the "VBase" human germline sequence database (available on the Internet www.mrccpe.com.ac.uk/vbase), as well as in Kabat, E. A., et al., 1991, Sequences of Proteins of Immunological Interest, 5th edition. In order to avoid the decrease in activity at the same time caused by the decrease in immunogenicity, the human antibody variable region framework sequence can be subjected to minimal reverse mutations or back mutations to maintain activity. The humanized antibodies of the present disclosure also include humanized antibodies that have been further subjected to affinity maturation of the CDRs by yeast display.

Due to the residues in contact with the antigen, CDR grafting may result in reduced affinity of the produced antibody or antigen-binding fragment thereof to the antigen due to the framework residues in contact with the antigen. Such interactions may be the result of hypermutation of somatic cells. Therefore, it may still be necessary to graft such donor framework amino acids to the framework of the humanized antibody. The amino acid residues involved in antigen binding and from non-human antibodies or antigen-binding fragments thereof can be identified by examining the sequence and structure of the animal monoclonal antibody variable region. Residues in the CDR donor framework that differ from the germline can be considered related. If the closest germline cannot be determined, the sequence can be compared with the consensus sequence of a subclass or of animal antibody sequence with a high percentage of similarity. Rare framework residues are thought to be the result of hypermutation of somatic cells and thus play an important role in binding.

In an embodiment of the present disclosure, the antibody or antigen-binding fragment thereof can further comprise a light chain constant region of human or murine κ, λ chain or variant thereof, or further comprise a heavy chain constant region of human or murine IgG1, IgG2, IgG3, IgG4 or variant thereof; preferably comprise a heavy chain constant region of human IgG1, IgG2 or IgG4, or IgG1, IgG2 or IgG4 variant with amino acid mutations (for example L234A and/or L235A mutation, and/or S228P mutation).

The "conventional variant" of the human antibody heavy chain constant region and the human antibody light chain constant region described in the present disclosure refers to the variant of heavy chain constant region or light chain constant region that has been disclosed in the prior art and does not change the structure and function of the antibody variable region. Exemplary variants include IgG1, IgG2, IgG3 or IgG4 heavy chain constant region variants with site-directed modifications and amino acid substitutions of the heavy chain constant region. Specific substitutions are such as YTE mutations, L234A and/or L235A mutations, S228P mutations, and/or mutations to obtain a knob-into-hole structure (making the antibody heavy chain have a combination of knob-Fc and hole-Fc) known in the art. These mutations have been confirmed to make the antibody have new properties, but do not change the function of the antibody variable region.

"HuMAb", "human antibody", "fully human antibody" and "complete human antibody" can be used interchangeably, and can refer to antibodies derived from humans or antibodies obtained from a genetically modified organism which is "engineered" to produce specific human antibodies in response to antigen stimulation and can be produced by any method known in the art. In some technologies, the elements of human heavy and light chain loci are introduced into cell lines of organisms derived from embryonic stem cell lines, in which the endogenous heavy chain and light chain loci have been target disrupted by what targets the endogenous heavy chain and light chain loci contained in these cell lines. Transgenic organisms can synthesize human antibodies specific to human antigens, and the organisms can be used to produce human antibody-secreting hybridomas. A human antibody can also be an antibody in which the heavy and light chains are encoded by nucleotide sequences derived from one or more human DNA sources. Fully human antibodies can also be constructed by gene or chromosome transfection methods and phage display technology, or constructed from B cells activated in vitro, all of which are known in the art.

The terms "full-length antibody", "intact antibody", "complete antibody" and "whole antibody" are used interchangeably herein and refer to an antibody in a substantially intact form, as distinguished from the antigen-binding fragments defined below. These terms specifically refer to an antibody in which the heavy chain comprises Fc region.

The term "antigen-binding fragment" or "functional fragment" of an antibody refers to one or more fragments of the antibody that retain the ability to specifically bind to an antigen (for example, PD-1). It has been shown that fragments of full-length antibodies can be used to perform the antigen-binding function of antibodies. Examples of the binding fragment included in the term "antigen-binding fragment" of the antibody include (i) Fab fragments, monovalent fragments consist of VL, VH, CL and CH1 domains; (ii) F(ab')$_2$ fragments, including bivalent fragments of two Fab fragments linked by a disulfide bridge in the hinge region, (iii) Fd fragments consist of VH and CH1 domains; (iv) Fv fragments composed of VH and VL domains of one arm of an antibody; (V) single domains or dAb fragments (Ward et al., (1989) Nature 341:544-546), which consist of a VH domain; and (vi) isolated complementarity determining regions (CDR) or (vii) combinations of two or more isolated CDRs, optionally linked by synthetic linkers. In addition, although the two domains VL and VH of the Fv fragment are encoded by separate genes, recombination methods can be used to link them by synthetic linkers so that it can be produced as a single protein chain in which the VL and VH regions pair to form a monovalent molecule (referred to as single-chain Fv (scFv); see, for example, Bird et al. (1988) Science 242:423-426; and Huston et al. (1988) Proc. Natl. Acad. Sci USA 85: 5879-5883). Such single chain antibodies are also intended to be included in the term "antigen-binding fragment" of antibody. Such antibody fragments are obtained by using conventional techniques known to those skilled in the art, and the functions of the fragments are screened in the same manner as for those of intact antibodies. The antigen binding moiety can be produced by recombinant DNA technology or by enzymatic or chemical cleavage of the intact immunoglobulin. The antibodies may be antibodies of different isotypes, for example, IgG (for example, IgG1, IgG2, IgG3 or IgG4 subtypes), IgA1, IgA2, IgD, IgE or IgM antibodies.

The antigen-binding fragments of the present disclosure include Fab, F(ab')2, Fab', single-chain antibody (scFv), dimerized V region (diabody), disulfide bond stabilized V region (dsFv), CDR-containing peptide and the like.

Fab is an antibody fragment that has a molecular weight of about 50,000 and has antigen-binding activity, and it is obtained by treating IgG antibody molecules with the protease papain (cleaves the amino acid residue at position 224 of the H chain), in which about half of the N-terminal side of the H chain and the entire L chain are joined together by disulfide bond(s).

The Fab of the present disclosure can be produced by using papain to treat the monoclonal antibody of the present disclosure which specifically recognizes human PD-1 and binds to the amino acid sequence of the extracellular region or three-dimensional structure thereof. In addition, the Fab can be produced by inserting the DNA encoding the Fab of the antibody into a prokaryotic expression vector or a eukaryotic expression vector and introducing the vector into a prokaryotic organism or eukaryotic organism to express the Fab.

F(ab')2 is an antibody fragment that has a molecular weight of about 100,000 and has antigen-binding activity and comprises two Fab regions linked at the hinge position, and it is obtained by digesting the lower part of the two disulfide bonds in the hinge region of IgG with the enzyme pepsin.

The F(ab')2 of the present disclosure can be produced by using pepsin to treat the monoclonal antibody of the present disclosure which specifically recognizes human PD-1 and binds to the amino acid sequence of the extracellular region or three-dimensional structure thereof. In addition, the F(ab')2 can be produced by linking Fab' described below with thioether bond or disulfide bond.

Fab' is an antibody fragment that has a molecular weight of about 50,000 and has antigen-binding activity obtained by cleaving the disulfide bond in the hinge region of the F(ab')2. The Fab' of the present disclosure can be produced by using reducing agents for example dithiothreitol to treat the F(ab')2 of the present disclosure which specifically recognizes PD-1 and binds to the amino acid sequence of the extracellular region or three-dimensional structure thereof.

In addition, the Fab' can be produced by inserting the DNA encoding the Fab' fragment of the antibody into a prokaryotic expression vector or a eukaryotic expression vector and then introducing the vector into a prokaryotic organism or eukaryotic organism to express the Fab'.

The term "single-chain antibody", "single-chain Fv" or "scFv" refers to molecules comprising an antibody heavy chain variable domain (or region; VH) and an antibody light chain variable domain (or region; VL) linked by a linker. Such scFv molecules can have the general structure: $NH_2$-VL-linker-VH-COOH or $NH_2$-VH-linker-VL-COOH. Suitable linkers in prior art consist of repeated GGGGS amino acid sequences or variants thereof, for example a variant with 1 to 4 repeated sequences (Holliger et al. (1993), Proc. Natl. Acad. Sci. USA 90: 6444-6448). Other linkers that can be used in the present disclosure are described in Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293: 41-56 and Roovers et al. (2001), Cancer Immunol.

The scFv of the present disclosure can be produced by the following steps: obtaining the cDNA encoding VH and VL of the monoclonal antibody of the present disclosure which specifically recognizes human PD-1 and binds to the amino acid sequence of the extracellular region or three-dimensional structure thereof, constructing the DNA encoding the scFv, inserting the DNA into a prokaryotic expression vector or a eukaryotic expression vector, and then introducing the expression vector into a prokaryotic organism or eukaryotic organism to express the scFv.

Diabody is a antibody fragment in which scFv is dimerized, and is a antibody fragment with bivalent antigen-binding activity. In the bivalent antigen binding activity, the two antigens can be the same or different.

The diabody of the present disclosure can be produced by the following steps: obtaining the cDNA encoding VH and VL of the monoclonal antibody of the present disclosure which specifically recognizes human PD-1 and binds to the amino acid sequence of the extracellular region or three-dimensional structure thereof, constructing the DNA encoding the scFv so that the peptide linker has 8 or less amino acid sequence residues in length, inserting the DNA into a prokaryotic expression vector or a eukaryotic expression vector, and then introducing the expression vector into a prokaryote organism or eukaryotic organism to express the diabody.

dsFv is obtained by linking polypeptides in which one amino acid residue in each of VH and VL is replaced by a cysteine residue via a disulfide bond between the cysteine residues. The amino acid residues substituted with cysteine residues can be selected according to a known method (Protein Engineering, 7, 697 (1994)) based on the prediction of the antibody three-dimensional structure.

The dsFv of the present disclosure can be produced by the following steps: obtaining the cDNA encoding VH and VL of the monoclonal antibody of the present disclosure which specifically recognizes human PD-1 and binds to the amino acid sequence of the extracellular region or three-dimensional structure thereof, constructing the DNA encoding the dsFv, inserting the DNA into a prokaryotic expression vector or a eukaryotic expression vector, and then introducing the expression vector into a prokaryotic organism or eukaryotic organism to express the dsFv.

The CDR-containing peptide is constructed by one or more regions including the CDR(s) of VH or VL. Peptides containing multiple CDR can be linked directly or via a suitable peptide linker.

The CDR-containing peptide of the present disclosure can be produced by the following steps: constructing the DNA(s) encoding the CDR(s) of VH and VL of the monoclonal antibody of the present disclosure which specifically recognizes human PD-1 and binds to the amino acid sequence of the extracellular region or three-dimensional structure thereof, inserting the DNA(s) into a prokaryotic expression vector or a eukaryotic expression vector, and then introducing the expression vector into a prokaryotic organism or eukaryotic organism to express the peptide. The CDR-containing peptide can also be produced by chemical synthesis methods for example the Fmoc method or the tBoc method.

The term "amino acid difference" or "amino acid mutation" refers to the presence of amino acid change(s) or mutation(s) in the protein or polypeptide variant compared with the original protein or polypeptide, including having 1, 2, 3 or more amino acid insertion, deletion or substitution on the basis of the original protein or polypeptide.

The term "antibody framework" or "FR region" refers to a moiety of the variable domain VL or VH, which serves as a scaffold for the antigen binding loop (CDR) of the variable domain. Essentially, it is a variable domain without CDR.

The term "complementarity determining region", "CDR" or "hypervariable region" refers to one of the six hypervariable regions in the variable domain of an antibody that mainly contribute to antigen binding. Generally, there are three CDRs (HCDR1, HCDR2 and HCDR3) in each heavy chain variable region, and three CDRs (LCDR1, LCDR2 and LCDR3) in each light chain variable region. Any one of well-known schemes can be used to determine the amino acid sequence boundaries of the CDRs, including the "Kabat" numbering criteria (see Kabat et al. (1991), "Sequences of Proteins of Immunological Interest", 5th edition, Public Health Service, National Institutes of Health, Bethesda, MD), "Chothia" numbering criteria (see Al-Lazikani et al., (1997) JMB 273:927-948) and ImmunoGenTics (IMGT) numbering criteria (Lefranc M. P., Immunologist, 7, 132-136 (1999); Lefranc, M. P., et al., Dev. Comp. Immunol., 27, 55-77 (2003)), etc. For example, for the classical format, following the Kabat Criteria, the numbering of CDR amino acid residues in the heavy chain variable domain (VH) is 31-35 (HCDR1), 50-65 (HCDR2) and 95-102 (HCDR3); the numbering of CDR amino acid residues in the light chain variable domain (VL) is 24-34 (LCDR1), 50-56 (LCDR2) and 89-97 (LCDR3). Following the Chothia criteria, the numbering of CDR amino acid residues in VH is 26-32 (HCDR1), 52-56 (HCDR2) and 95-102 (HCDR3); and the numbering of amino acid residues in VL is 26-32

(LCDR1), 50-52 (LCDR2) and 91-96 (LCDR3). According to the combination of the CDR definitions of both Kabat and Chothia, the CDRs consist of amino acid residues 26-35 (HCDR1), 50-65 (HCDR2) and 95-102 (HCDR3) in human VH and amino acid residues 24-34 (LCDR1), 50-56 (LCDR2) and 89-97 (LCDR3) in human VL. Following IMGT criteria, the numbering of CDR amino acid residues in VH is roughly 26-35 (CDR1), 51-57 (CDR2) and 93-102 (CDR3), and the numbering of CDR amino acid residues in VL is roughly 27-32 (CDR1), 50-52 (CDR2) and 89-97 (CDR3). Following IMGT criteria, the CDR regions of an antibody can be determined using the program IMGT/DomainGap Align.

The term "epitope" or "antigenic determinant" refers to a site on an antigen to which an immunoglobulin or antibody specifically binds (for example, a specific site on PD-L1 molecules). Epitopes usually include at least 3, 4, 5, 6, 7, 8, 9, 10, 11, 12, 13, 14 or 15 consecutive or non-consecutive amino acids in a unique spatial conformation. See, for example, Epitope Mapping Protocols in Methods in Molecular Biology, Vol. 66, G. E. Morris, Ed. (1996).

The terms "specifically binds", "selectively binds", "binds selectively" and "binds specifically" refer to the binding of an antibody to an epitope on a predetermined antigen. Generally, antibodies bind with an affinity (KD) of about less than $10^{-8}$ M, for example about less than $10^{-9}$M, $10^{-10}$ M, $10^{-11}$M or less.

The term "KD" or "Kd" refers to the dissociation equilibrium constant of a specific antibody-antigen interaction. Generally, the antibodies of the present disclosure bind to PD-1 with a dissociation equilibrium constant (KD) of less than about $10^{-7}$ M, for example, less than about $10^{-8}$ M or $10^{-9}$ M, for example, as measured in a BIACORE instrument using surface plasma resonance (SPR) technology.

When the term "competition" is used in the context of antigen binding proteins that compete for the same epitope (for example neutralizing antigen binding proteins or neutralizing antibodies), it refers to the competition between the antigen binding proteins, and can be determined by the following assay: in the assay, the antigen-binding protein to be tested (for example an antibody or immunologically functional fragment thereof) prevents or inhibits (for example reduces) the specific binding of a reference antigen-binding protein (for example a ligand or a reference antibody) to a common antigen (for example PD-1 or fragment thereof). Numerous types of competitive binding assays can be used to determine whether one antigen-binding protein competes with another, these assays are for example: solid phase direct or indirect radioimmunoassay (RIA), solid phase direct or indirect enzyme immunoassay (EIA), sandwich competition assay (see for example Stahli et al., 1983, Methods in Enzymology 9:242-253); solid phase direct biotin-avidin EIA (see for example Kirkland et al., 1986, J. Immunol. 137:3614-3619), solid phase direct labeling assay, solid phase direct labeling sandwich assay (see for example Harlow and Lane, 1988, Antibodies, A Laboratory Manual, Cold Spring Harbor Press); solid phase direct labeling RIA with I-125 labels (see for example Morel et al., 1988, Molec. Immunol. 25: 7-15); solid-phase direct biotin-avidin EIA (see for example Cheung et al., 1990, Virology 176: 546-552); and direct labeling RIA (Moldenhauer et al., 1990, Scand. J. Immunol. 32:77-82). Generally, the assay involves using purified antigen bound to a solid surface or cell carrying either an unlabeled antigen binding protein to be tested or a labeled reference antigen binding protein. Competitive inhibition is measured by measuring the amount of label bound to the solid surface or cell in the presence of the antigen binding protein being tested. Usually the antigen binding protein being tested is present in excess. The antigen binding proteins identified by competition assays (competitive antigen binding proteins) include: antigen binding proteins that bind to the same epitope as the reference antigen binding protein; and antigen binding proteins that binds to adjacent epitopes that are sufficiently close to the binding epitope of the reference antigen binding protein, the two epitopes sterically hinder each other from binding. Additional details on the methods used to determine competitive binding are provided in the examples herein. Usually when the competitive antigen binding protein is present in excess, it will inhibit (for example reduce) the specific binding of the reference antigen binding protein to the common antigen by at least 40-45%, 45-50%, 50-55%, 55-60%, 60-65%, 65-70%, 70%-75% or 75% or more. In some cases, the binding is inhibited by at least 80-85%, 85-90%, 90-95%, 95-97%, or 97% or more.

The term "nucleic acid molecule" used herein refers to DNA molecules and RNA molecules. The nucleic acid molecule can be single-stranded or double-stranded, and is preferably double-stranded DNA or single-stranded mRNA or modified mRNA. When a nucleic acid is placed in a functional relationship with another nucleic acid sequence, the nucleic acid is "operatively linked". For example, if a promoter or enhancer affects the transcription of a coding sequence, then the promoter or enhancer is operatively linked to the coding sequence.

The term "vector" refers to a nucleic acid molecule capable of transporting another nucleic acid to which it has been linked. In one embodiment, the vector is a "plasmid", which refers to a circular double-stranded DNA loop into which additional DNA segments can be linked. In another embodiment, the vector is a viral vector in which additional DNA segments can be linked into the viral genome. The vectors disclosed herein can replicate autonomously in the host cell into which they have been introduced (for example, bacterial vector with bacterial origin of replication and episomal mammalian vector) or can be integrated into the genome of the host cell after being introduced into the host cell, so as to replicate together with the host genome (for example, non-episomal mammalian vector).

The methods for producing and purifying antibodies and antigen-binding fragments are well known in the prior art, such as Antibodies: A Laboratory Manual, Cold Spring Harbor, Chapters 5-8 and 15. For example, mice can be immunized with human PD-1 or fragments thereof, and the obtained antibodies can be renatured, purified, and amino acid sequencing can be performed by conventional methods. Antigen-binding fragments can also be prepared by conventional methods. One or more human FR regions are added to the non-human CDR regions of the antibodies or antigen-binding fragments of the invention by using genetic engineering methods. The human FR germline sequences can be obtained from the ImmunoGeneTics (IMGT) website http://imgt.cines.fr by comparing the IMGT human antibody variable region germline gene database and MOE software, or be obtained from The Immunoglobulin FactsBook, 2001ISBN012441351.

The term "host cell" refers to a cell into which an expression vector has been introduced. Host cells can include bacteria, microorganisms, plant or animal cells. Bacteria that can be easily transformed include members of the enterobacteriaceae, for example *Escherichia coli* or *Salmonella* strains; Bacillaceae for example *Bacillus subtilis*; Pneumococcus; *Streptococcus* and *Haemophilus influenzae*. Suitable microorganisms include *Saccharomyces* cerevisiae and Pichia pastoris. Suitable animal host cell lines include CHO (Chinese Hamster Ovary Cell Line) and NS0 cells.

The engineered antibodies or antigen-binding fragments of the present disclosure can be prepared and purified by conventional methods. For example, the cDNA sequences encoding the heavy and light chains can be cloned and recombined into a GS expression vector. The recombinant immunoglobulin expression vector can be stably transfected into CHO cells. As a more recommended prior art, mammalian expression systems can lead to glycosylation of antibodies, especially in the highly conserved N-terminal sites of the Fc region. Stable clones are obtained by expressing antibodies that specifically bind to human PD-1. Positive clones are expanded in the serum-free medium of the bioreactor to produce antibodies. The culture medium into which the antibodies are secreted can be purified by conventional techniques. For example, using A or G Sepharose FF column with adjusted buffer for purification. Non-specifically binding components are washed away. Then the binding antibodies are eluted by the pH gradient method, and the antibody fragments are detected by SDS-PAGE and collected. The antibodies can be filtered and concentrated by conventional methods. Soluble mixtures and polymers can also be removed by conventional methods, for example molecular sieves and ion exchange. The resulting product needs to be frozen immediately, such as −70° C., or lyophilized.

"Administering", "giving" and "treating", when applied to animals, humans, experimental subjects, cells, tissues, organs or biological fluids, refer to the contact of the exogenous medicament, therapeutic agent, diagnostic agent or composition with the animals, humans, subjects, cells, tissues, organs or biological fluids. "Administering", "giving" and "treating" can refer to for example treatment, pharmacokinetics, diagnosis, research and experimental methods. The treatment of cells includes contact of reagents with cells, and contact of reagents with fluids, in which the fluids are in contact with the cells. "Administering", "giving" and "treating" also refer to treating for example cells by reagents, diagnosis, binding compositions or by another cell in vitro and ex vivo. "Treating" when applied to human, veterinary or research subjects, refers to therapeutic treatment, preventing or preventive measures, research and diagnostic applications.

"Treatment" refers to administering an internal or external therapeutic agent, for example a composition comprising any one of the binding compounds of the present disclosure, to a patient who has one or more symptoms of a disease on which the therapeutic agent is known to have therapeutic effect. Generally, the therapeutic agent is administered in an amount effective to alleviate one or more symptoms of the disease in the treated patient or population to induce the regression of such symptoms or inhibit the development of such symptoms to any clinically measured extent. The amount of therapeutic agent that is effective to alleviate any specific disease symptom (also referred to as a "therapeutically effective amount") can vary according to a variety of factors, for example the patient's disease state, age and body weight, and the ability of the drug to produce the desired therapeutic effect in the patient. Whether the disease symptoms have been alleviated can be evaluated through any clinical testing methods commonly used by doctors or other health care professionals to evaluate the severity or progression of the symptoms. Although the embodiments of the present disclosure (for example treatment methods or products) may be ineffective in alleviating each target disease symptom, but as determined according to any statistical test methods known in the art such as Student t-test, chi-square test, Mann and Whitney's U test, Kruskal-Wallis test (H test), Jonckheere-Terpstra test and Wilcoxon test, they should reduce the target disease symptom in a statistically significant number of patients.

"Conservative modification" or "conservative replacement or substitution" refers to replacing the amino acids in a protein with other amino acids having similar characteristics (for example charge, side chain size, hydrophobicity/hydrophilicity, main chain conformation and rigidity, etc.) so that changes can be frequently made without changing the biological activity of the protein. Those skilled in the art know that, generally speaking, a single amino acid replacement in a non-essential region of a polypeptide does not substantially change the biological activity (see for example Watson et al. (1987) Molecular Biology of the Gene, The Benjamin/Cummings Pub. Co., Page 224, (4th edition)). In addition, the replacement of amino acids with similar structure or function is unlikely to disrupt the biological activity. Exemplary conservative substitutions are indicated in the table below "Exemplary amino acid conservative substitutions".

TABLE 3

Exemplary amino acid conservative substitutions

| Original residue | Conservative substitution |
| --- | --- |
| Ala(A) | Gly; Ser |
| Arg(R) | Lys; His |
| Asn(N) | Gln; His; Asp |
| Asp(D) | Glu; Asn |
| Cys(C) | Ser; Ala; Val |
| Gln(Q) | Asn; Glu |
| Glu(E) | Asp; Gln |
| Gly(G) | Ala |
| His(H) | Asn; Gln |
| Ile(I) | Leu; Val |
| Leu(L) | Ile; Val |
| Lys(K) | Arg; His |
| Met(M) | Leu; Ile; Tyr |
| Phe(F) | Tyr; Met; Leu |
| Pro(P) | Ala |
| Ser(S) | Thr |
| Thr(T) | Ser |
| Trp(W) | Tyr; Phe |
| Tyr(Y) | Trp; Phe |
| Val(V) | Ile; Leu |

"Effective amount" or "effective dose" refers to the amount of a drug, compound or pharmaceutical composition necessary to obtain any one or more beneficial or desired therapeutic results. For preventive use, the beneficial or desired results include elimination or reduction of risk, reduction of severity or delay of the disease onset, including the biochemistry, histology and behavioral symptoms of the disease, complications thereof and intermediate pathological phenotypes that occur during the developmental process of the disease. For therapeutic applications, the beneficial or desired results include clinical results, for example reducing the incidence of various target antigen-related disorders of the present disclosure or improving one or more symptoms of the disorder, reducing the dose of other agents required to treat the disorder, enhancing the therapeutic effect of another agent, and/or delaying the progression of target antigen-related disorder of the present disclosure of the patient.

"Exogenous" refers to substances produced outside organisms, cells or human bodies according to circumstances. "Endogenous" refers to substances produced inside cells, organisms or human bodies according to circumstances.

"Homology" refers to the sequence similarity between two polynucleotide sequences or between two polypeptides. When the positions in the two sequences compared are occupied by the same base or amino acid monomer subunit, for example if each position of two DNA molecules is occupied by adenine, then the molecules are homologous at that position. The homology percentage between two sequences is a function of the number of matching or homologous positions shared by the two sequences divided by the number of positions compared×100. For example, in the optimal sequence alignment, if there are 6 matches or homology in the 10 positions in the two sequences, then the two sequences are 60% homologous; if there are 95 matches or homology in the 100 positions in the two sequences, then the two sequences are 95% homologous. Generally, when two sequences are aligned, comparison is made to give the maximum percentage homology. For example, the comparison can be performed by the BLAST algorithm, in which the parameters of the algorithm are selected to give the maximum match between each sequence over the entire length of each reference sequence. The following references relate to the BLAST algorithm that is often used for sequence analysis: BLAST ALGORITHMS: Altschul, S. F. et al., (1990) J. Mol. Biol. 215:403-410; Gish, W. et al., (1993) Nature Genet. 3:266-272; Madden, T. L. et al., (1996) Meth. Enzymol. 266:131-141; Altschul, S. F. et al., (1997) Nucleic Acids Res. 25:3389-3402; Zhang, J. et al., (1997) Genome Res. 7:649-656. Other conventional BLAST algorithms such as provided by NCBI BLAST are also well known to those skilled in the art.

The expressions "cell", "cell line" and "cell culture" as used herein can be used interchangeably, and all such names include progeny. Therefore, the words "transformant" and "transformed cell" include primary test cells and cultures derived therefrom, regardless of the passage numbers. It should also be understood that due to deliberate or unintentional mutations, all offspring cannot be exactly the same in terms of DNA content. Mutant progeny with the same function or biological activity as screened in the original transformed cells is included. It will be clearly understood from the context when a different name is referred to.

"Polymerase chain reaction" or "PCR" as used herein refers to a procedure or technique in which a trace amount of a specific portion of nucleic acid, RNA and/or DNA is amplified as described in for example U.S. Pat. No. 4,683, 195. Generally speaking, it is necessary to obtain sequence information from the end or outside of the target region so that oligonucleotide primers can be designed; these primers are the same or similar in terms of sequence to the corresponding strands of the template to be amplified. The 5' terminal nucleotides of the two primers can be identical to the ends of the material to be amplified. PCR can be used to amplify specific RNA sequences, specific DNA sequences from total genomic DNA, and cDNA, phage or plasmid sequences transcribed from total cellular RNA, etc. See generally Mullis et al. (1987) Cold Spring Harbor, Symp. Quant. Biol. 51:263; Erlich ed., (1989) PCR TECHNOLOGY (Stockton Press, N.Y.). The PCR used herein is regarded as an example, but not the only example, of a nucleic acid polymerase reaction method for amplifying a nucleic acid test sample, and the method includes using known nucleic acids as primers and nucleic acid polymerases to amplify or produce a specific portion of the nucleic acid.

"Isolated" refers to a purified state, and in this case means that the designated molecule is substantially free of other biomolecules, for example nucleic acids, proteins, lipids, carbohydrates or other materials, for example cell debris and growth medium. Generally, the term "isolated" is not intended to mean the complete absence of these materials or the absence of water, buffers or salts, unless they are present in an amount that significantly interferes with the experimental or therapeutic use of the compound as described herein.

"Optional" or "optionally" means that the event or environment described later can, but not necessarily occur, and the description includes occasions where the event or environment occurs or does not occur. For example, "optionally comprising 1 to 3 antibody heavy chain variable regions" means that the antibody heavy chain variable regions of specific sequences may but does not have to be present.

"Pharmaceutical composition" means a mixture comprising one or more of the compounds described herein, or a physiologically/pharmaceutically acceptable salt or a prodrug thereof, and other chemical components, for example physiological/pharmaceutically acceptable carriers and excipients. The purpose of the pharmaceutical composition is to promote the administration to the organism, which facilitates the absorption of the active ingredient and thereby exerts biological activity.

The term "pharmaceutically acceptable carrier" refers to any inactive substance suitable for use in a formulation for the delivery of antibodies or antigen-binding fragments. The carrier can be an anti-adhesive agent, binder, coating, disintegrant, filler or diluent, preservative (such as antioxidant, antibacterial or antifungal agent), sweetener, absorption delaying agent, wetting agent, emulsifier, buffer, etc. Examples of suitable pharmaceutically acceptable carriers include water, ethanol, polyols (for example glycerol, propanediol, polyethylene glycol, etc.) dextrose, vegetable oils (for example olive oil), saline, buffer, buffered saline, and isotonic agents for example sugars, polyols, sorbitol and sodium chloride.

In addition, the present disclosure includes agents for treating diseases related to target antigen (for example PD-1) positive cells, the agents comprising the anti-PD-1 antibody or antigen-binding fragment thereof of the present disclosure as an active ingredient.

The disease related to PD-1 in the present disclosure is not limited, as long as it is a disease related to PD-1. For example, the therapeutic response induced by the molecule of the present disclosure can be achieved by binding to human PD-1, and then inhibiting the binding of PD-1 and its ligands PD-L1 and PD-L2, or killing tumor cells overexpressing PD-1. Therefore, when in preparations and formulations suitable for therapeutic applications, the molecules of the present disclosure are very useful for people who have tumor or cancer, preferably melanoma, colon cancer, breast cancer, lung cancer, gastric cancer, bowel cancer, kidney cancer, non-small cell lung cancer, bladder cancer, etc.

In addition, the present disclosure relates to methods for immunodetection or determination of target antigens (for example PD-1), reagents for immunodetection or determination of target antigens (for example PD-1), methods for immunodetection or determination of cells expressing target antigens (for example PD-1) and diagnostic agents for diagnosing diseases related to target antigen (for example PD-1) positive cells, which includes the antibody or antibody fragment of the present disclosure, which specifically recognizes target antigen (for example human PD-1) and binds with the amino acid sequence of the extracellular region or three-dimensional structure thereof, being used as an active ingredient.

In the present disclosure, the method used for detecting or measuring the amount of the target antigen (for example PD-1) may be any known method. For example, it includes immunodetection or measurement methods.

The immunodetection or measurement methods are methods of detecting or measuring the amount of antibody or antigen using labeled antigens or antibodies. Examples of immunodetection or measurement methods include radioimmunoassay (MA), enzyme immunoassay (EIA or ELISA), fluorescence immunoassay (FIA), luminescence immunoassay, western blotting, physicochemical methods, etc.

The aforementioned diseases related to PD-1 positive cells can be diagnosed by detecting or measuring PD-1 expressing cells using the antibodies or antibody fragments of the present disclosure.

In order to detect cells expressing the polypeptide, known immunodetection methods can be used, preferably using immunoprecipitation, fluorescent cell staining, immunohistochemical staining, etc. In addition, fluorescent antibody staining method using the FMAT8100HTS system (Applied Biosystem) can be used.

In the present disclosure, there is no particular limitation on the in vivo sample used for detection or measurement of the target antigen (for example PD-1), as long as it has the possibility of containing cells expressing the target antigen (for example PD-1), for example histocytes, blood, plasma, serum, pancreatic juice, urine, feces, tissue fluid or culture fluid.

According to the required diagnostic method, the diagnostic agent comprising the monoclonal antibody or antibody fragment thereof of the present disclosure can also comprise reagents for performing antigen-antibody reaction or reagents for detecting the reaction. The reagents used to perform the antigen-antibody reaction include buffers, salts, etc. The reagents used for detection include reagents commonly used in immunodetection or measurement methods, for example labeled second antibodies that recognize the monoclonal antibody, antibody fragment thereof or conjugate thereof, and a substrate corresponding to the label, etc.

Preparation of Antigens

1. Construction of Antigens:

A human PD-1-IgG1Fc fusion protein is designed and synthesized, with 150 amino acids of the extracellular region of human PD-1 at the N-terminus and the Fc fragment of human IgG1 (hIgG1Fc) at the C-terminus. A recombinant PD-1-Fc protein with high-purity can be obtained after purifying with Protein A affinity column and is used to detect the binding of anti-PD-1 antibody to antigen.

```
Human PD-1-IgG1Fc (SEQ ID NO: 1):
MEFGLSWLFLVAILKGVQCPGWFLDSPDRPWNPPTFSPALLVVTEGDNAT

FTCSFSNTSESFVLNWYRMSPSNQTDKLAAFPEDRSQPGQDCRFRVTQLP

NGRDFHMSVVRARRNDSGTYLCGAISLAPKAQIKESLRAELRVTERRAEV

PTARPSPSPRPAGQFQTLVEPKSSDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENlVYKTTP

PVLDSDGSFFLYSKLTVDKSRWQQGNVFSCSVMHEALHNHYTQKSLSLSP

GK.
```

Note: The underlined part is the signal peptide, the normal part is the extracellular region of human PD-1, and the italicized part is hIgG1Fc (signal peptide+extracellular region+hIgG1Fc).

```
Human PD-1-his (SEQ ID NO: 2):
MEFGLSWLFLVAILKGVQCPGWFLDSPDRPWNPPTFSPALLVVT

EGDNATFTCSFSNTSESFVLNWYRMSPSNQTDKLAAFPEDRSQPGQDCR

FRVTQLPNGRDFHMSVVRARRNDSGTYLCGAISLAPKAQIKESLRAELR

VTERRAEVPTARPSPSPRPAGQFQTLVGSSDYKDDDDKHHHHHH.

PD-1 antigen encoded by nucleic acids transfected
into cells (SEQ ID NO: 3):
MQIPQAPWPVVWAVLQLGWRPGWFLDSPDRPWNPPTFSPALLV

VTEGDNATFTCSFSNTSESFVLNWYRMSPSNQTDKLAAFPEDRSQPGQD

CRFRVTQLPNGRDFHMSVVRARRNDSGTYLCGAISLAPKAQIKESLRAE

LRVTERRAEVPTAHPSPSPRPAGQFQTLVVGVVGGLLGSLVLLVWVLAV

ICSRAARGTIGARRTGQPLKEDPSAVPVFSVDYGELDFQWREKTPEPPV

PCVPEQTEYATIVFPSGMGTSSPARRGSADGPRSAQPLRPEDGHCSWP

L.
```

Preparation of Antibodies

Anti-human PD-1 antibodies can be produced by immunizing mice, and can also be obtained from anti-human PD-1 phage mouse immunization library.

The method of preparing anti-human PD-1 antibody by immunizing mice is as follows:

1. Immunization: laboratory SJL white mice, female, 6-8 weeks old and Balb/c white mice, female, 6-8 weeks old. Housing environment: SPF level. After the mice were purchased, they were housed in a laboratory environment for 1 week under adjustment of 12/12 hours light/dark cycle, at temperature 20-25° C.; humidity 40-60%. The mice adapted to the environment were immunized according to different protocols, with 6-10 mice in each group. The immune antigen could be the purified recombinant protein PD-1-IgG1Fc (see SEQ ID NO: 1), PD-1-his (see SEQ ID NO: 2), or Jurkat/CHO-PD-1 cells transfected with PD-1 as the antigen (see SEQ ID NO: 3). A single antigen combined with different immune adjuvants or different types of immunogens could be used for cross-immunization. The immunization site could be the abdominal cavity or under the skin on the back, or alternately immunized at the two sites. The immune adjuvant TiterMax® Gold Adjuvant (hereinafter referred to as Titermax, purchased from Sigma, Cat. No. T2684) and Imject Alum Adjuvant (hereinafter referred to as Alum, purchased from Pierce, Cat. No. 77161) were used for cross-immunization. The ratio of antigen to adjuvant (Titermax) was 1:1, the ratio of antigen to adjuvant (Alum) was 3:1, 25-50 μg/animal (first immunization), 50 μg/animal (booster immunization), or 1×10$^7$ Jurkat/CHO-PD-1 cells/animal. On day 0, 25-50 μg/animal emulsified antigen was intraperitoneally injected, once a week or once every two weeks after the first immunization, Titermax and Alum were alternately used, 5-8 times in total.

2. Cell fusion: mice with high antibody titers in the serum were selected for spleen cell fusion. The eyes of mice were bled 72 h after sprint immunization. The mice were sacrificed by pulling the neck and put in 75% ethanol for disinfection. Splenic lymphocytes were fused to myeloma cells Sp2/0 cells (Chinese Academy of Sciences) to obtain hybridoma cells by applying the optimized PEG-mediated fusion procedure. The fused hybridoma cells were re-suspended in HAT complete medium (RPMI-1640 medium containing 20% FBS, 1×HAT and 1×OPI), and aliquoted into 96-well cell culture plates (1×10$^5$/150 µl/well), incubated at 37° C., 5% $CO_2$, and seeded into totally about 10-30 plates. On day 5 after fusion, HAT complete medium was added at 50 µl/well, and incubated at 37° C., 5% $CO_2$. From day 7 to day 8 after fusion, according to the cell growth density, the medium was completely changed at 200 µl/well, and incubated at 37° C., 5% $CO_2$.

3. Hybridoma cell screening: 7-9 days after fusion, according to the cell growth density, the ELISA method was carried out to detect the binding of antibody to PD-1, and the cells in positive wells were further detected with ELISA for detection of the blockade of PD-1/PDL1 binding. The medium in the positive wells were changed and the cells were expanded to 24-well plates in time according to the cell density. The cell lines transferred to 24-well plates were retested and then preserved and subcloned for the first time. Those positive in the first subcloning screening were preserved, and the second or third subcloning were performed until obtaining single-cell clones. Hybridoma cells with the effect of blocking the binding of PD-1 and PDL1 were obtained by multiple fusions.

The method of obtaining anti-human PD-1 antibodies through the anti-human PD-1 phage mouse immune library is as follows:

1. Construction of an anti-human PD-1 phage mouse immune library: the spleens of mice with high antibody titer in the serum were selected, and the tissue total RNA was extracted by using Trizol (Invitrogen Cat No. 15596-018). The cDNA were obtained by using PrimeScript™ II 1st Strand cDNA Synthesis Kit (Takara Cat No. 6210A) for reverse transcription. Primers to construct the library were designed and synthesized according to the IMGT database. Single-chain antibody fragments were obtained through three rounds of PCR reactions. The single-chain antibody fragments and the modified library construction vector pCantab5E (Amersham Biosciences/GE Cat No. 27-9400-01) were digested with Sfi1 (NEB Cat No. #R0123L), and purified and recovered with E. Z. N. A.® Gel Extraction Kit (Omega Cat No. D2500-02) after electrophoresis. Then T4 DNA ligase (NEB Cat No. #M0202L) was used for ligation at 16° C. for 16-18 h, and the above kit was used for purification and recovery, and finally elution was performed with deionized water. 1 µg of ligation product was taken and mixed with 1 vial of competent TG1 (Lucigen Cat No. 60502-2) for electro-transformation, and the electro-transformation was performed with the electroporator (Bio Rad Micropulser), with parameters set to 2.5 kV, 200Ω and 25 uF. The transformation was repeated for 10 times. The product was spread on the plates and cultured up-side-down at 37° C. for 16-18 h. All the colonies were then detached and mixed together, added with glycerin at a final concentration of 15%, and stored at −80° C. for use.

2. Screening of the anti-human PD-1 phage mouse immune library: the packaged anti-human PD-1 phage immune library (1×10$^{12}$-1×10$^{13}$) and 100 µl streptomycin microbeads (Milenvi Biotec, Auburn, CA) were added to 1 ml phosphate buffered saline containing 2% skimmed milk (MPBS) and incubated at room temperature for 1 h, placed on a magnetic stand, and the supernatant was collected. 10 µg/ml biotinylated human PD-1-ECD-his protein (purchased from Sino Biological) was added to the supernatant and incubated for 1 h at room temperature. Then 100 µl of streptavidin-coated magnetic beads (pre-incubated with 1 ml MPBS) was added and incubated for 1 h at room temperature. And it was loaded on the magnetic stand system for sorting, and the supernatant was aspirated. 1 ml PBST (phosphate buffer containing 0.1% Tween-20) was added and turned over several times. Fresh washing solution was added after complete aspiration, repeated 11 times to remove unbound antibody fragments, and 0.5 ml elution solution (50 µl 10 mg/ml trypsin stock solution added into 450 µl PBS) was added. It was shaken for 15 min at room temperature, placed on a magnetic stand, and the supernatant was aspirated into a new EP tube. TG1 was seeded into 2YT medium and expanded until the cultured bacterium density OD600=0.4. 1.75 ml of TG1 (OD600=0.4) was added to each tube, and 250 µl of eluted phage (phage) was added, incubated in a 37° C. water bath for 30 min, and spread on plates with gradient dilution for testing the titer. The remaining TG1 solution was centrifuged, spread on plates and incubated overnight at 37° C.

The phage mouse immune library was screened 2-3 rounds by using the biotinylated human PD-1-ECD-his antigen, with MACS screening (streptomycin magnetic beads, Invitrogen), and monoclonal antibodies capable of binding to PD-1 and capable of blocking the binding of PD-1 to PD-L1 were finally obtained and verified by sequencing. The variable region sequences of the antibodies were obtained.

Purification of Recombinant Antigen Proteins/Antibodies

1. Separation and purification of hybridoma supernatant/Protein G affinity chromatography:

For the purification of mouse hybridoma supernatant, Protein G for affinity chromatography was the first choice. The cultured hybridoma was centrifuged to collect the supernatant, and 10-15% volume of 1 M Tris-HCl (pH 8.0-8.5) was added according to the volume of the supernatant to adjust the pH of the supernatant. For the Protein G column, 6 M guanidine hydrochloride was used to wash 3-5 times the column volume, and then pure water was used to wash 3-5 times the column volume; a buffer system such as 1×PBS (pH 7.4) as an equilibration buffer was used to equilibrate the column for 3-5 times the column volume; The cell supernatant was loaded and bound by using a low flow rate, which was controlled so that the retention time was about 1 min or longer; 1×PBS (pH 7.4) was used to wash the chromatographic column 3-5 times the column volume until the UV absorption dropped to baseline: 0.1M acetic acid/sodium acetate (pH 3.0) buffer was used for sample elution, the elution peaks were collected according to UV detection, and 1 M Tris-HCl (pH 8.0) was used to quickly adjust the pH of the eluted product to 5-6 for temporary storage. For the eluted product, solution replacement could be performed by methods well known to those skilled in the art, such as using ultrafiltration tubes for ultrafiltration and concentration and replacing the solution to the required buffer system, or using molecular exclusion such as G-25 to desalt and replace to the required buffer system, or using high-resolution molecular exclusion columns such as Superdex 200 to remove the components aggregated in the eluted product to improve sample purity.

2. Protein A affinity chromatography purification of proteins or antibodies:

First, the supernatant of the cell culture expressing the antigen protein or antibody was centrifuged at a high speed to collect the supernatant. For the Protein A affinity column, 6 M guanidine hydrochloride was used to wash 3-5 times the column volume, and then pure water was used to wash 3-5 times the column volume. A buffer system such as 1×PBS (pH 7.4) was used as an equilibration buffer to equilibrate the chromatography column for 3-5 times the column volume. The cell supernatant was loaded and bound by using a low flow rate, which was controlled so that the retention time was about 1 min or longer. After the binding was completed, 1×PBS (pH 7.4) was used to wash the chromatographic column 3-5 times the column volume until the UV absorption dropped to baseline. 0.1M acetic acid/sodium acetate (pH 3.0-3.5) buffer was used for sample elution, the elution peaks were collected according to UV detection, and 1 M Tris-HCl (pH 8.0) was used to quickly adjust the pH of the eluted product to 5-6 for temporary storage. For the eluted product, solution replacement could be performed by methods well known to those skilled in the art, such as using ultrafiltration tubes for ultrafiltration and concentration and replacing the solution to the required buffer system, or using molecular exclusion such as G-25 to desalt and replace to the required buffer system, or using high-resolution molecular exclusion columns such as Superdex 200 to remove the components aggregated in the eluted product to improve sample purity.

EXAMPLES

The present disclosure is further described below in combination with the examples, but these examples do not limit the scope of the present disclosure. The experimental methods for which the conditions are not specifically indicated in the examples of the present disclosure usually follow conventional conditions, such as Antibodies: A Laboratory Manual and Molecular Cloning: A Laboratory Manual, Cold Spring Harbor; or according to the conditions recommended by the raw material or product manufacturer. The reagents for which the sources are not specifically indicated are the conventional reagents available from the market.

Example 1. Obtaining Anti-Human PD-1 Murine Antibodies

The anti-human PD-1 murine antibodies obtained by the aforementioned method were subjected to antigen binding experiments and screened to obtain multiple strains of antibodies with good activity: wherein M23, M32 and M33 were included. The single cell clones were expanded and cultured, the RNA was extracted, and degenerate primers of mouse-Ig were used to perform reverse transcription amplification (RT-PCR) to obtain the variable region sequence of the antibody. The murine antibody variable region sequence was linked with the human antibody constant region sequence. The chimeric antibody of the murine monoclonal antibody was cloned and expressed recombinantly, and in vitro activity experiments were performed to confirm that the obtained monoclonal antibody variable region sequence was correct.

The variable region sequences of murine antibodies M23, M32 and M33 are determined as follows:

```
The heavy chain variable region of murine antibody
M23 (SEQ ID NO: 4):
QVQLQQSGAELVRPGASVTLSCKASGYTFTDYEMHWVKQTPIHGLEWIG
LIDPETGGTVYNQKFKDKTILTADKSSSTAYMEFRSLTSEDSAVYHCTR
ERFSYYGSTSDWYFDVWGTGTTVTVSS.

The light chain variable region of murine antibody
M23 (SEQ ID NO: 5):
DGLMTQTPLSLPVSLGDHASISCRSSQSLVHSNGNTYLEWYLQKPGQSP
KLLIYKVSNRFSGVPDRFSGSGSGTDFTLKISRVEAEDLGIYYCFQGSH
VPYTFGGGTKLEIK.

The heavy chain variable region of murine antibody
M32 (SEQ ID NO: 6):
QVQLQQSGAELVRPGASVTLSCKASDFTFTDYEIHWVKQTPVHGLEWIG
LFDPETGGIVYNQKFKGKAILTADKSSNTAYMEFRSLTSEDSAVYYCTR
EGYNRDWYFDVWGTGTTVTVSS.

The light chain variable region of murine antibody
M32 (SEQ ID NO: 7):
DVLMTQTPLSLPVSLGDQASISCRSSQSIVHSNGNTYLEWYLQKPGQSP
KLLIYKVSNRFSGVPDRFSGSGSGTDFTLKISRVEAEDLGIYYCFQGSH
VPYAFGGGTKLEIK.

The heavy chain variable region of murine antibody
M33 (SEQ ID NO: 19):
KVMLVESGGGLVKPGGSLKLSCAASGFTFSSYAMSWVRQTPEKRLEWVA
TISGGGVDTYYQDNVQGRFTISRDNAKNTLYLQMSSLRSEDTALYYCAS
PYGHGYFDVWGTGTTVTVSS.

The light chain variable region of murine antibody
M33 (SEQ ID NO: 20):
DIQMTQTTSSLSASLGDRVTISCRASQDINNFLNWYQQKPDGTVKLLIY
YTSSLHSGVPSRFSGSGSGTDYSLTISNLEQEDIATYFCQQGNTLPWTF
GGGTKLEIK.
```

Note: in the heavy chain variable region and light chain variable region sequences of the above antibodies, underlined are the CDR sequences determined by the Kabat numbering system, in the order as follows: FR1-CDR1-FR2-CDR2-FR3-CDR3-FR4.

TABLE 4

Murine antibody M23, M32 and M33 heavy chain and light chain CDR region sequences

| Name of antibody | Heavy chain | | Light chain | |
|---|---|---|---|---|
| M23 | HCDR1 | DYEMH (SEQ ID NO: 8) | LCDR1 | RSSQSLVHSNGNTYLE (SEQ ID NO: 11) |
| | HCDR2 | LIDPETGGTVYNQKFKD (SEQ ID NO: 9) | LCDR2 | KVSNRFS (SEQ ID NO: 12) |
| | HCDR3 | ERFSYYGSTSDWYFDV (SEQ ID NO: 10) | LCDR3 | FQGSHVPYT (SEQ ID NO: 13) |
| M32 | HCDR1 | DYEIH (SEQ ID NO: 14) | LCDR1 | RSSQSIVHSNGNTYLE (SEQ ID NO: 17) |
| | HCDR2 | LFDPETGGIVYNQKFKG (SEQ ID NO: 15) | LCDR2 | KVSNRFS (SEQ ID NO: 12) |
| | HCDR3 | EGYNRDWYFDV (SEQ ID NO: 16) | LCDR3 | FQGSHVPYA (SEQ ID NO: 18) |

TABLE 4-continued

Murine antibody M23, M32 and M33 heavy chain and light chain CDR region sequences

| Name of antibody | Heavy chain | | Light chain | |
|---|---|---|---|---|
| M33 | HCDR1 | SYAMS (SEQ ID NO: 21) | LCDR1 | RASQDINNFLN (SEQ ID NO: 24) |
| | HCDR2 | TISGGGVDTYYQDNVQG (SEQ ID NO: 22) | LCDR2 | YTSSLHS (SEQ ID NO: 25) |
| | HCDR3 | PYGHGYFDV (SEQ ID NO: 23) | LCDR3 | QQGNTLPWT (SEQ ID NO: 26) |

Note: the antibody CDR sequences in the table are determined according to the Kabat numbering system.

Example 2. Humanization of Anti-Human PD-1 Monoclonal Antibodies

By aligning against the IMGT human antibody heavy and light chain variable region germline gene database and MOE software analysis, the human germline heavy and light chain variable region germline genes with high identity with M23, M32 and M33 light and heavy chain sequences were selected as templates. The CDR of these 3 murine antibodies were grafted into the corresponding human antibody templates to construct their corresponding humanized antibodies, respectively.

1. Humanization of Murine Antibody M23
1.1 Selection of Humanization Framework of Murine Antibody M23

The humanization light chain templates of the murine antibody M23 are IGKV2-40*01 and IGKJ4*01, and the humanization heavy chain templates are IGHV1-69*02 and IGHJ6*01. The sequences of the variable regions after humanization are as follows (underlined are the CDR sequences):

Hu23VH-CDR grafted:
(SEQ ID NO: 27)
EVQLVQSGAEVKKPGSSVKVSCKASGGTFSDYEMHWVRQAPGQGLEWMG
LIDPETGGTVYNQKFKDRVTITADKSTSTAYMELSSLRSEDTAVYYCAR
ERFSYYGSTSDWYFDVWGQGTTVTVSS.

Hu23VL-CDR grafted:
(SEQ ID NO: 28)
DIVMTQTPLSLPVTPGEPASISCRSSQSLVHSNGNTYLEWYLQKPGQSP
QLLIYKVSNRFSGVPDRFSGSGSGTDFTLKISRVEAEDVGVYYCFQGSH
VPYTFGGGTKVEIK.

1.2 Humanization Template Selection and Back Mutation Design of Murine Antibody M23

TABLE 5

Back mutations of murine antibody M23 humanized antibodies

| VL | | VH | |
|---|---|---|---|
| Hu23VL1 | Grafted | Hu23VH1 | Grafted |
| Hu23VL2 | I2G | Hu23VH2 | G27Y I69L |
| | | Hu23VH3 | G27Y M48I V67T I69L L82F |
| | | Hu23VH4 | G27Y M48I V67T I69L L82F A93T |

Note: grafted means that the murine antibody CDRs are implanted into the human germline FR region sequences. The amino acid residues are determined and annotated by the Kabat numbering system, for example I2G means that the I at position 2 of Kabat numbering is mutated back to G according to the Kabat numbering system.

The light/heavy chain variable region sequences of the humanized antibodies of M23 are as follows:

>Hu23VL1 (same as Hu23VL-CDR grafted):
(SEQ ID NO: 28)
DIVMTQTPLSLPVTPGEPASISCRSSQSLVHSNGNTYLEWYLQKPGQSP
QLLIYKVSNRFSGVPDRFSGSGSGTDFTLKISRVEAEDVGVYYCFQGSH
VPYTFGGGTKVEIK.

>Hu23VL2
(SEQ ID NO: 29)
DGVMTQTPLSLPVTPGEPASISCRSSQSLVHSNGNTYLEWYLQKPGQSP
QLLIYKVSNRFSGVPDRFSGSGSGTDFTLKISRVEAEDVGVYYCFQGSH
VPYTFGGGTKVEIK.

>Hu23VH1 (same as Hu23VH-CDR grafted):
(SEQ ID NO: 27)
EVQLVQSGAEVKKPGSSVKVSCKASGGTFSDYEMHWVRQAPGQGLEWMG
LIDPETGGTVYNQKFKDRVTITADKSTSTAYMELSSLRSEDTAVYYCAR
ERFSYYGSTSDWYFDVWGQGTTVTVSS.

>Hu23VH2
(SEQ ID NO: 30)
EVQLVQSGAEVKKPGSSVKVSCKASGYTFSDYEMHWVRQAPGQGLEWMG
LIDPETGGTVYNQKFKDRVTLTADKSTSTAYMELSSLRSEDTAVYYCAR
ERFSYYGSTSDWYFDVWGQGTTVTVSS.

>Hu23VH3
(SEQ ID NO: 31)
EVQLVQSGAEVKKPGSSVKVSCKASGYTFSDYEMHWVRQAPGQGLEWIG
LIDPETGGTVYNQKFKDRTTLTADKSTSTAYMEFSSLRSEDTAVYYCAR
ERFSYYGSTSDWYFDVWGQGTTVTVSS.

>Hu23VH4
(SEQ ID NO: 32)
EVQLVQSGAEVKKPGSSVKVSCKASGYTFSDYEMHWVRQAPGQGLEWIG
LIDPETGGTVYNQKFKDRTTLTADKSTSTAYMEFSSLRSEDTAVYYCTR
ERFSYYGSTSDWYFDVWGQGTTVTVSS.

1.3 Humanized Sequence Combination of Murine Antibody M23

The antibodies and variable region combinations thereof obtained by humanization of the murine antibody M23 are shown in the table below.

TABLE 6

Combinations of humanized Hu23 antibody variable regions

| | VL | |
|---|---|---|
| VH | Hu23VL1 | Hu23VL2 |
| Hu23VH1 | Hu23-1 | Hu23-5 |
| Hu23VH2 | Hu23-2 | Hu23-6 |

TABLE 6-continued

Combinations of humanized Hu23 antibody variable regions

| VH | VL | |
|---|---|---|
| | Hu23VL1 | Hu23VL2 |
| Hu23VH3 | Hu23-3 | Hu23-7 |
| Hu23VH4 | Hu23-4 | Hu23-8 |

Note:
"Hu23-1" refers to an antibody wherein the light chain variable region is Hu23VL1 and heavy chain variable region is Hu23VH1, and so on.

Combinations of the antibody light/heavy chain variable regions (for example Hu23-1) referred to in the above table can be linked with the antibody light/heavy chain constant regions to form full-length antibodies, respectively; unless otherwise specified in the present disclosure, when forming a full-length antibody, the light chain variable region is linked to the Kappa chain constant region shown in SEQ ID NO: 73 to form the antibody light chain, and the heavy chain variable region is linked to the IgG4-AA heavy chain constant region shown in SEQ ID NO: 72 or to the IgG4-P heavy chain constant region shown in ID NO: 79 to form the antibody heavy chain, and the name in the table referring to the combination of the antibody light/heavy chain variable regions (for example Hu23-1) plus the suffix ".IgG4AA" means the full-length antibody formed by ligation with the IgG4-AA heavy chain constant region, plus the suffix ".IgG4P" means the full-length antibody formed by ligation with the IgG4-P heavy chain constant region, for example, "Hu23-1.IgG4AA" means the full-length antibody formed by linking the heavy chain, formed by linking Hu23VH1 heavy chain variable region and IgG4-AA heavy chain constant region as shown in SEQ ID NO: 72, and the light chain, formed by linking the Hu23VL1 light chain variable region and the Kappa chain constant region as shown in SEQ ID NO: 73. "Hu23-1.IgG4P" means the full-length antibody formed by linking the heavy chain, formed by linking Hu23VH1 heavy chain variable region and IgG4-P heavy chain constant region as shown in SEQ ID NO: 79, and the light chain, formed by linking the Hu23VL1 light chain variable region and the Kappa chain constant region as shown in SEQ ID NO: 73.

2. Humanization of Murine Antibody M32

2.1 Selection of Humanization Framework of Murine Antibody M32

The humanization light chain templates of the murine antibody M32 are IGKV2-40*01 and IGKJ4*01, and the humanization heavy chain templates are IGHV1-69*02 and IGHJ6*01. The sequences of the humanized variable regions are as follows (underlined are the CDR sequences):

Hu32VH-CDR grafted: IGHV1-69*02 and IGHJ6*01
(SEQ ID NO: 33)
EVQLVQSGAEVKKPGSSVKVSCKASGGTFSDYEIHWVRQAPGQGLEWMG
LFDPETGGIVYNQKFKGRVTITADKSTSTAYMELSSLRSEDTAVYYCAR
EGYNRDWYFDVWGQGTTVTVSS.

Hu32VL-CDR grafted:
(SEQ ID NO: 34)
DIVMTQTPLSLPVTPGEPASISCRSSQSIVHSNGNTYLEWYLQKPGQSP
QLLIYKVSNRFSGVPDRFSGSGSGTDFTLKISRVEAEDVGVYYCFQGSH
VPYAFGGGTKVEIK.

2.2 Humanization Template Selection and Back Mutation Design of Murine Antibody M32

TABLE 7

Back mutations of murine antibody M32 humanized antibodies

| VL | | VH | |
|---|---|---|---|
| Hu32VL1 | Grafted | Hu32 VH1 | Grafted |
| Hu32VL2 | I2V | Hu32 VH2 | G27F, I69L, A93T |
| | | Hu32 VH3 | G26D, G27F, I69L, A93T |
| | | Hu32 VH4 | G27F, M48I, V67A, I69L, L82F, A93T |
| | | Hu32 VH5 | G26D, G27F, S30T, M48I, V67A, I69L, L82F, A93T |
| | | Hu32 VH6 | G26D, G27F, S30T, R38K, Q43H, M48I, R66K, V67A, I69L, L82F, A93T |

Note: grafted means that the murine antibody CDRs are implanted into the human germline FR region sequences. The amino acid residues are determined and annotated by the Kabat numbering system, for example I2V means that the I at position 2 of Kabat numbering is mutated back to V according to the Kabat numbering system.

The light and heavy chain variable region sequences of the humanized antibodies of murine antibody M32 are as follows:

>Hu32VL1 (same as Hu32VL-CDR grafted):
(SEQ ID NO: 34)
DIVMTQTPLSLPVTPGEPASISCRSSQSIVHSNGNTYLEWYLQKPGQ
SPQLLIYKVSNRFSGVPDRFSGSGSGTDFTLKISRVEAEDVGVYYCF
QGSHVPYAFGGGTKVEIK.

>Hu32VL2
(SEQ ID NO: 35)
DVVMTQTPLSLPVTPGEPASISCRSSQSIVHSNGNTYLEWYLQKPGQ
SPQLLIYKVSNRFSGVPDRFSGSGSGTDFTLKISRVEAEDVGVYYCF
QGSHVPYAFGGGTKVEIK.

>Hu32VH1 (same as Hu23VH-CDR grafted):
(SEQ ID NO: 33)
EVQLVQSGAEVKKPGSSVKVSCKASGGTFSDYEIHWVRQAPGQGLEW
MGLFDPETGGIVYNQKFKGRVTITADKSTSTAYMELSSLRSEDTAVY
YCAREGYNRDWYFDVWGQGTTVTVSS.

>Hu32VH2
(SEQ ID NO: 36)
EVQLVQSGAEVKKPGSSVKVSCKASGFTFSDYEIHWVRQAPGQGLEW
MGLFDPETGGIVYNQKFKGRVTLTADKSTSTAYMELSSLRSEDTAVY
YCTREGYNRDWYFDVWGQGTTVTVSS.

>Hu32VH3
(SEQ ID NO: 37)
EVQLVQSGAEVKKPGSSVKVSCKASDFTFSDYEIHWVRQAPGQGLEW
MGLFDPETGGIVYNQKFKGRVTLTADKSTSTAYMELSSLRSEDTAVY
YCTREGYNRDWYFDVWGQGTTVTVSS.

>Hu32VH4
(SEQ ID NO: 38)
EVQLVQSGAEVKKPGSSVKVSCKASGFTFSDYEIHWVRQAPGQGLEW
IGLFDPETGGIVYNQKFKGRATLTADKSTSTAYMEFSSLRSEDTAVY
YCTREGYNRDWYFDVWGQGTTVTVSS.

>Hu32VH5
(SEQ ID NO: 39)
EVQLVQSGAEVKKPGSSVKVSCKASDFTFTDYEIHWVRQAPGQGLEW
IGLFDPETGGIVYNQKFKGRATLTADKSTSTAYMEFSSLRSEDTAVY
YCTREGYNRDWYFDVWGQGTTVTVSS.

>Hu32VH6
(SEQ ID NO: 40)
EVQLVQSGAEVKKPGSSVKVSCKASDFTFTDYEIHWVKQAPGHGLEW
IGLFDPETGGIVYNQKFKGKATLTADKSTSTAYMEFSSLRSEDTAVY
YCTREGYNRDWYFDVWGQGTTVTVSS.

2.3 Humanized Sequence Combination of Murine Antibody M32

The antibodies and variable region combinations thereof obtained by humanization of the murine antibody M32.

TABLE 8

Combinations of the light/heavy chain variable regions of the humanized antibody Hu32

|  | VL | |
| --- | --- | --- |
| VH | Hu32VL1 | Hu32VL2 |
| Hu32VH1 | Hu32-1 | Hu32-7 |
| Hu32VH2 | Hu32-2 | Hu32-8 |
| Hu32VH3 | Hu32-3 | Hu32-9 |
| Hu32VH4 | Hu32-4 | Hu32-10 |
| Hu32VH5 | Hu32-5 | Hu32-11 |
| Hu32VH6 | Hu32-6 | Hu32-12 |

Note: in the table for example, "Hu32-1" refers to an antibody with the combination of antibody light chain variable region of Hu32VL1 and heavy chain variable region of Hu32VH1, and so on.

Combinations of the antibody light/heavy chain variable regions (for example Hu32-1) referred to in the above table can be linked with the antibody light/heavy chain constant regions to form full-length antibodies, respectively; unless otherwise specified in the present disclosure, when forming a full-length antibody, the light chain variable region is linked to the Kappa chain constant region shown in SEQ ID NO: 73 to form the antibody light chain, and the heavy chain variable region is linked to the IgG4-AA heavy chain constant region shown in SEQ ID NO: 72 or to the IgG4-P heavy chain constant region shown in ID NO: 79 to form the antibody heavy chain, and the name in the table referring to the combination of the antibody light/heavy chain variable regions (for example Hu32-1) plus the suffix ".IgG4AA" means the full-length antibody formed by ligation with the IgG4-AA heavy chain constant region, plus the suffix ".IgG4P" means the full-length antibody formed by ligation with the IgG4-P heavy chain constant region, for example, "Hu32-1.IgG4AA" means the full-length antibody formed by linking the heavy chain, formed by linking Hu32VH1 heavy chain variable region and IgG4-AA heavy chain constant region as shown in SEQ ID NO: 72, and the light chain, formed by linking the Hu32VL1 light chain variable region and the Kappa chain constant region as shown in SEQ ID NO: 73. "Hu32-1.IgG4P" means the full-length antibody formed by linking the heavy chain, formed by linking Hu32VH1 heavy chain variable region and IgG4-P heavy chain constant region as shown in SEQ ID NO: 79, and the light chain, formed by linking the Hu32VL1 light chain variable region and the Kappa chain constant region as shown in SEQ ID NO: 73.

3. Humanization of Murine Antibody M33

3.1 Selection of Humanization Framework of Murine Antibody M33

The humanization light chain templates of the murine antibody M33 are IGKV1-39*01 and IGKJ4*01, and the humanization heavy chain templates are IGHV3-7 and IGHJ6*01. The sequences of the humanized variable regions are as follows (underlined are the CDR sequences):

Hu33VH-CDR grafted (SEQ ID NO: 41):
EVQLVESGGGLVQPGGSLRLSCAASGFTFSSYAMSWVRQAPGKGLEWVA
TISGGGVDTYYQDNVQGRFTISRDNAKNSLYLQMNSLRAEDTAVYYCAR
PYGHGYFDVWGQGTTVTVSS.

Hu33VL-CDR grafted (SEQ ID NO: 42):
DIQMTQSPSSLSASVGDRVTITCRASQDINNFLNWYQQKPGKAPKLLIY
YTSSLHSGVPSRFSGSGSGTDFTLTISSLQPEDFATYYCQQGNTLPWTF
GGGTKVEIK.

3.2 Humanization Template Selection and Back Mutation Design of Murine Antibody M33

TABLE 9

Back mutations of murine antibody M33 humanized antibodies

| VL | | VH | |
| --- | --- | --- | --- |
| Hu33VL1 | Grafted | Hu33VH1 | Grafted |
| Hu33VL2 | F71Y | Hu33VH2 | R94S |
| Hu33VL3 | K42G P44V F71Y | Hu33VH3 | E1K R94S |

Note: grafted means that the murine antibody CDRs are implanted into the human germline FR region sequences. The amino acid residues are determined and annotated by the Kabat numbering system, for example F71Y means that F at position 71 of Kabat numbering is mutated back to Y according to the Kabat numbering system.

The light chain variable region and heavy chain variable region sequences of the humanized antibodies of murine antibody M33 are as follows:

>Hu33VL (same as Hu33VL-CDR grafted):
(SEQ ID NO: 42)
DIQMTQSPSSLSASVGDRVTITCRASQDINNFLNWYQQKPGKAPKLLIY
YTSSLHSGVPSRFSGSGSGTDFTLTISSLQPEDFATYYCQQGNTLPWTF
GGGTKVEIK.

>Hu33VL2
(SEQ ID NO: 43)
DIQMTQSPSSLSASVGDRVTITCRASQDINNFLNWYQQKPGKAPKLLIY
YTSSLHSGVPSRFSGSGSGTDYTLTISSLQPEDFATYYCQQGNTLPWTF
GGGTKVEIK.

>Hu33VL3
(SEQ ID NO: 44)
DIQMTQSPSSLSASVGDRVTITCRASQDINNFLNWYQQKPGGAVKLLIY
YTSSLHSGVPSRFSGSGSGTDYTLTISSLQPEDFATYYCQQGNTLPWTF
GGGTKVEIK.

>Hu33VH1 (same as Hu33VH-CDR grafted):
(SEQ ID NO: 41)
EVQLVESGGGLVQPGGSLRLSCAASGFTFSSYAMSWVRQAPGKGLEWVA
TISGGGVDTYYQDNVQGRFTISRDNAKNSLYLQMNSLRAEDTAVYYCAR
PYGHGYFDVWGQGTTVTVSS.

>Hu33VH2
(SEQ ID NO: 45)
EVQLVESGGGLVQPGGSLRLSCAASGFTFSSYAMSWVRQAPGKGLEWVA
TISGGGVDTYYQDNVQGRFTISRDNAKNSLYLQMNSLRAEDTAVYYCAS
PYGHGYFDVWGQGTTVTVSS.

>Hu33VH3
(SEQ ID NO: 46)
KVQLVESGGGLVQPGGSLRLSCAASGFTFSSYAMSWVRQAPGKGLEWVA
TISGGGVDTYYQDNVQGRFTISRDNAKNSLYLQMNSLRAEDTAVYYCAS
PYGHGYFDVWGQGTTVTVSS.

3.3 Humanized Sequence Combination of Murine Antibody M33

TABLE 10

Combinations of the light and heavy chain variable regions of the humanized antibody

| VH | VL | | |
|---|---|---|---|
| | Hu33VL1 | Hu33VL2 | Hu33VL3 |
| Hu33VH1 | Hu33-1 | Hu33-4 | Hu33-7 |
| Hu33VH2 | Hu33-2 | Hu33-5 | Hu33-8 |
| Hu33VH3 | Hu33-3 | Hu33-6 | Hu33-9 |

Note: in the table for example, "Hu33-6" refers to an antibody with the combination of the antibody light chain variable region of Hu33VL2 and the heavy chain variable region of Hu33VH3, and so on.

Combinations of the antibody light/heavy chain variable regions (for example Hu33-6) referred to in the above table can be linked with the antibody light/heavy chain constant regions to form full-length antibodies, respectively; unless otherwise specified in the present disclosure, when forming a full-length antibody, the light chain variable region is linked to the Kappa chain constant region shown in SEQ ID NO: 73 to form the antibody light chain, and the heavy chain variable region is linked to the IgG4-AA heavy chain constant region shown in SEQ ID NO: 72 or the IgG4-P heavy chain constant region shown in ID NO: 79 to form the antibody heavy chain, and the name in the table referring to the combination of the antibody light/heavy chain variable regions (for example Hu33-6) plus the suffix ".IgG4AA" means the full-length antibody formed by ligation with the IgG4-AA heavy chain constant region, plus the suffix ".IgG4P" means the full-length antibody formed by ligation with the IgG4-P heavy chain constant region, for example, "Hu32-6.IgG4AA" means the full-length antibody formed by linking the heavy chain, formed by linking Hu33VH3 heavy chain variable region and IgG4-AA heavy chain constant region as shown in SEQ ID NO: 72, and the light chain, formed by linking the Hu33VL2 light chain variable region and the Kappa chain constant region as shown in SEQ ID NO: 73. "Hu33-6.IgG4P" means the full-length antibody formed by linking the heavy chain, formed by linking Hu33VH3 heavy chain variable region and IgG4-P heavy chain constant region as shown in SEQ ID NO: 79, and the light chain, formed by linking the Hu33VL2 light chain variable region and the Kappa chain constant region as shown in SEQ ID NO: 73.

4. Mutants of Humanized Antibodies

4.1 Mutant Antibodies of Hu23 Humanized Antibody

Through computer simulation, amino acids at specific sites of the light chain LCDR1 (SEQ ID NO: 11) of the Hu23 humanized antibody were subjected to site-directed mutations, and the specific mutations are shown in Table 11:

TABLE 11

Mutant sequences of Hu23 light chain LCDR1:

| Name | Sequence (SEQ ID NO) |
|---|---|
| Hu23LCDR1(N28Q) | RSSQSLVHSQGNTYLE (SEQ ID NO: 47) |
| Hu23LCDR1(N28L) | RSSQSLVHSLGNTYLE (SEQ ID NO: 48) |
| Hu23LCDR1(N28T) | RSSQSLVHSTGNTYLE (SEQ ID NO: 49) |
| Hu23LCDR1(N28D) | RSSQSLVHSDGNTYLE (SEQ ID NO: 50) |
| Hu23LCDR1(G29A) | RSSQSLVHSNANTYLE (SEQ ID NO: 51) |
| Hu23LCDR1(G29V) | RSSQSLVHSNVNTYLE (SEQ ID NO: 52) |

Note: Hu23LCDR1 (N28Q) means the LCDR1 mutation sequence in which N at position 28 according to the Kabat numbering criteria of the Hu23 humanized antibody light chain variable region Hu23VL1 or Hu23VL2 is mutated to Q, Hu23LCDR1 (G29A) means the LCDR1 mutation sequence in which G at position 29 according to the Kabat numbering criteria of the Hu23 humanized antibody light chain variable region Hu23VL1 or Hu23VL2 is mutated to A (the CDRs are determined by the Kabat numbering system).

The sequences of the Hu23 humanized antibody light chain variable region after LCDR1 mutation are as follows:

```
>Hu23VL1(N28Q) sequence is:
                                                    (SEQ ID NO: 53)
DIVMTQTPLSLPVTPGEPASISCRSSQSLVHSQGNTYLEWYLQKPGQSPQLLIYKVS
NRFSGVPDRFSGSGSGTDFTLKISRVEAEDVGVYYCFQGSHVPYTFGGGTKVEIK >Hu23VL1(N28L) sequence is:
                                                    (SEQ ID NO: 54)
DIVMTQTPLSLPVTPGEPASISCRSSQSLVHSLGNTYLEWYLQKPGQSPQLLIYKVSN
RFSGVPDRFSGSGSGTDFTLKISRVEAEDVGVYYCFQGSHVPYTFGGGTKVEIK >Hu23VL1(N28T) sequence is:
                                                    (SEQ ID NO: 55)
DIVMTQTPLSLPVTPGEPASISCRSSQSLVHSTGNTYLEWYLQKPGQSPQLLIYKVSN
RFSGVPDRFSGSGSGTDFTLKISRVEAEDVGVYYCFQGSHVPYTFGGGTKVEIK >Hu23VL1(N28D) sequence is:
                                                    (SEQ ID NO: 56)
DIVMTQTPLSLPVTPGEPASISCRSSQSLVHSDGNTYLEWYLQKPGQSPQLLIYKVS
NRFSGVPDRFSGSGSGTDFTLKISRVEAEDVGVYYCFQGSHVPYTFGGGTKVEIK
```

-continued

```
>Hu23VL1(G29A) sequence is:
                                                    (SEQ ID NO: 57)
DIVMTQTPLSLPVTPGEPASISCRSSQSLVHSNANTYLEWYLQKPGQSPQLLIYKVS
NRFSGVPDRFSGSGSGTDFTLKISRVEAEDVGVYYCFQGSHVPYTFGGGTKVEIK >Hu23VL1(G29V) sequence is:
                                                    (SEQ ID NO: 58)
DIVMTQTPLSLPVTPGEPASISCRSSQSLVHSNVNTYLEWYLQKPGQSPQLLIYKVS
NRFSGVPDRFSGSGSGTDFTLKISRVEAEDVGVYYCFQGSHVPYTFGGGTKVEIK >Hu23VL2(N28Q) sequence is:
                                                    (SEQ ID NO: 59)
DGVMTQTPLSLPVTPGEPASISCRSSQSLVHSQGNTYLEWYLQKPGQSPQLLIYKVS
NRFSGVPDRFSGSGSGTDFTLKISRVEAEDVGVYYCFQGSHVPYTFGGGTKVEIK >Hu23VL2(N28L) sequence is:
                                                    (SEQ ID NO: 60)
DGVMTQTPLSLPVTPGEPASISCRSSQSLVHSLGNTYLEWYLQKPGQSPQLLIYKVS
NRFSGVPDRFSGSGSGTDFTLKISRVEAEDVGVYYCFQGSHVPYTFGGGTKVEIK >Hu23VL2(N28T) sequence is:
                                                    (SEQ ID NO: 61)
DGVMTQTPLSLPVTPGEPASISCRSSQSLVHSTGNTYLEWYLQKPGQSPQLLIYKVS
NRFSGVPDRFSGSGSGTDFTLKISRVEAEDVGVYYCFQGSHVPYTFGGGTKVEIK >Hu23VL2(N28D) sequence is:
                                                    (SEQ ID NO: 62)
DGVMTQTPLSLPVTPGEPASISCRSSQSLVHSDGNTYLEWYLQKPGQSPQLLIYKVS
NRFSGVPDRFSGSGSGTDFTLKISRVEAEDVGVYYCFQGSHVPYTFGGGTKVEIK >Hu23VL2(G29A) sequence is:
                                                    (SEQ ID NO: 63)
DGVMTQTPLSLPVTPGEPASISCRSSQSLVHSNANTYLEWYLQKPGQSPQLLIYKVS
NRFSGVPDRFSGSGSGTDFTLKISRVEAEDVGVYYCFQGSHVPYTFGGGTKVEIK >Hu23VL2(G29V) sequence is:
                                                    (SEQ ID NO: 64)
DGVMTQTPLSLPVTPGEPASISCRSSQSLVHSNVNTYLEWYLQKPGQSPQLLIYKVS
NRFSGVPDRFSGSGSGTDFTLKISRVEAEDVGVYYCFQGSHVPYTFGGGTKVEIK
```

TABLE 12

Combinations of the light and heavy chain variable regions of the Hu23 humanized antibody

| VL | VH | | | |
|---|---|---|---|---|
| | Hu23VH1 | Hu23VH2 | Hu23VH3 | Hu23VH4 |
| Hu23VL1(N28Q) | Hu23-9 | Hu23-21 | Hu23-33 | Hu23-45 |
| Hu23VL1(N28L) | Hu23-10 | Hu23-22 | Hu23-34 | Hu23-46 |
| Hu23VL1(N28T) | Hu23-11 | Hu23-23 | Hu23-35 | Hu23-47 |
| Hu23VL1(N28D) | Hu23-12 | Hu23-24 | Hu23-36 | Hu23-48 |
| Hu23VL1(G29A) | Hu23-13 | Hu23-25 | Hu23-37 | Hu23-49 |
| Hu23VL1(G29V) | Hu23-14 | Hu23-26 | Hu23-38 | Hu23-50 |
| Hu23VL2(N28Q) | Hu23-15 | Hu23-27 | Hu23-39 | Hu23-51 |
| Hu23VL2(N28L) | Hu23-16 | Hu23-28 | Hu23-40 | Hu23-52 |
| Hu23VL2(N28T) | Hu23-17 | Hu23-29 | Hu23-41 | Hu23-53 |
| Hu23VL2(N28D) | Hu23-18 | Hu23-30 | Hu23-42 | Hu23-54 |
| Hu23VL2(G29A) | Hu23-19 | Hu23-31 | Hu23-43 | Hu23-55 |
| Hu23VL2(G29V) | Hu23-20 | Hu23-32 | Hu23-44 | Hu23-56 |

Note: in the table for example, "Hu23-11" refers to an antibody with the combination of the antibody light chain variable region of Hu23VL1(N28T) and heavy chain variable region of Hu23VH1, and so on.

Combinations of the antibody light/heavy chain variable regions (for example Hu23-11) referred to in the above table can be linked with the antibody light/heavy chain constant regions to form full-length antibodies, respectively; unless otherwise specified in the present disclosure, when forming a full-length antibody, the light chain variable region is linked to the Kappa chain constant region shown in SEQ ID NO: 73 to form the antibody light chain, and the heavy chain variable region is linked to the IgG4-AA heavy chain constant region shown in SEQ ID NO: 72 or the IgG4-P heavy chain constant region shown in ID NO: 79 to form the antibody heavy chain, and the name in the table referring to the combination of the antibody light/heavy chain variable regions (for example Hu23-11) plus the suffix ".IgG4AA" means the full-length antibody formed by ligation with the IgG4-AA heavy chain constant region, plus the suffix ".IgG4P" means the full-length antibody formed by ligation with the IgG4-P heavy chain constant region, for example, "Hu23-11.IgG4AA" means the full-length antibody formed by linking the heavy chain, formed by linking Hu23VH1 heavy chain variable region and IgG4-AA heavy chain constant region as shown in SEQ ID NO: 72, and the light chain, formed by linking the Hu23VL1(N28T) light chain variable region and the Kappa chain constant region as shown in SEQ ID NO: 73. "Hu23-11.IgG4P" means the full-length antibody formed by linking the heavy chain, formed by linking Hu23VH1 heavy chain variable region and IgG4-P heavy chain constant region as shown in SEQ ID NO: 79, and the light chain, formed by linking the Hu23VL1 (N28T) light chain variable region and the Kappa chain constant region as shown in SEQ ID NO: 73.

The experimental results showed that after site mutations, the humanized antibodies Hu23LCDR1 (N28Q), Hu23LCDR1 (N28L), Hu23LCDR1 (N28T), Hu23LCDR1 (N28D), Hu23LCDR1 (G29A) and Hu23LCDR1 (G29V) all maintained the ability of binding to PD-1 (Table 16).

4.2 Mutant Antibodies of Hu32 Humanized Antibody

The series of humanized antibodies Hu23 derived from M23 and the series of humanized antibodies Hu32 derived from M32 had high sequence identity by sequence analysis. The Hu23 light chain variable region and the Hu32 heavy chain variable region were combined into new light and heavy chain variable region combinations. The experimental results showed that the humanized antibodies comprising the new light and heavy chain variable region combinations maintain the ability of binding to the PD-1 antigen (Table 16).

TABLE 13

General formulas of Hu32 and Hu23 antibody variable region consensus sequences

| | Heavy chain | | Light chain |
|---|---|---|---|
| HCDR1 | DYEX$_1$H, wherein X$_1$ is selected from I or M; (SEQ ID NO: 65) | LCDR1 | RSSQSX$_{13}$VHSX$_{14}$X$_{15}$X$_{16}$TYLE, wherein, X$_{13}$ is selected from I or L, X$_{14}$ is selected from N, Q, L, T or D, X$_{15}$ is selected from G, A or V, and X$_{16}$ is selected from N or K; (SEQ ID NO: 68) |
| HCDR2 | LX$_2$DPETGGX$_3$VYNQKFKX$_4$, wherein X$_2$ is selected from F or I, X$_3$ is selected from I/T and wherein X$_4$ is selected from G or D; (SEQ ID NO: 66) | LCDR2 | KVSNRFS; (SEQ ID NO: 12) |
| HCDR3 | EX$_5$X$_6$X$_7$X$_8$YX$_9$X$_{10}$X$_{11}$X$_{12}$DWYFDV, wherein X$_5$ is selected from G or R, X$_6$ is F or absent, X$_7$ is S or absent, X$_8$ is Y or absent, X$_9$ is G or absent, X$_{10}$ is S or absent, X$_{11}$ is selected from N or T and X$_{12}$ is selected from R or S; (SEQ ID NO: 67) | LCDR3 | FQGSHVPYX$_{17}$, wherein X$_{17}$ is selected from A or T; (SEQ ID NO: 69) |
| VH | EVQLVQSGAEVKKPGSSVKVSCKASX$_{18}$X$_{19}$TFX$_{20}$DYEX$_1$HWVX$_{21}$QAPGX$_{22}$GLEWX$_{23}$GLX$_2$DPETGGX$_3$VYNQKFKX$_4$X$_{24}$X$_{25}$TX$_{26}$TADKSTSTAYMEX$_{27}$SSLRSEDTAVYYCX$_{28}$REX$_5$X$_6$X$_7$X$_8$YX$_9$X$_{10}$X$_{11}$X$_{12}$DWYFDVWGQGTTVTVSS, wherein, X$_1$ is selected from I or M, X$_2$ is selected from F or I, X$_3$ is selected from I/T, X$_4$ is selected from G or D, X$_5$ is selected from G or R, X$_6$ is F or absent, X$_7$ is S or absent, X$_8$ is Y or absent, X$_9$ is G or absent, X$_{10}$ is S or absent, X$_{11}$ is selected from N or T, X$_{12}$ is selected from R or S, X$_{18}$ is selected from G or D, X$_{19}$ is selected from G, F or Y, X$_{20}$ is selected from S or T, X$_{21}$ is selected from R or K, X$_{22}$ is selected from Q or H, X$_{23}$ is selected from M or I, X$_{24}$ is selected from R or K, X$_{25}$ is selected from V, A or T, X$_{26}$ is selected from R or K, X$_{27}$ is selected from L or F and X$_{28}$ is selected from A or T (SEQ ID NO: 70) | VL | DX$_{29}$VMTQTPLSLPVTPGEPASISCRSSQSX$_{13}$VHSX$_{14}$X$_{15}$X$_{16}$TYLEWYLQKPGQSPQLLIYKVSNRFSGVPDRFSGSGSGTDFTLKISRVEAEDVGVYYCFQGSHVPYX$_{17}$FGGGTKVEIK, wherein, X$_{13}$ is selected from I or L, X$_{14}$ is selected from N, Q, L, T or D, X$_{15}$ is selected from G, A or V, X$_{16}$ is selected from N or K, X$_{17}$ is selected from A or T and X$_{29}$ is selected from I, V or G. (SEQ ID NO: 71) |

TABLE 14

Combinations of Hu32 heavy chain variable regions and Hu23 light chain variable regions

| | VH | | | | | |
|---|---|---|---|---|---|---|
| VL | Hu32VH 1 | Hu32VH 2 | Hu32VH 3 | Hu32VH 4 | Hu32VH 5 | Hu32VH 6 |
| Hu23VL1 (N28Q) | Hu32a-13 | Hu32a-27 | Hu32a-41 | Hu32a-55 | Hu32a-69 | Hu32a-83 |
| Hu23VL1 (N28L) | Hu32a-14 | Hu32a-28 | Hu32a-42 | Hu32a-56 | Hu32a-70 | Hu32a-84 |

TABLE 14-continued

Combinations of Hu32 heavy chain variable regions and Hu23 light chain variable regions

| VL | Hu32VH1 | Hu32VH2 | Hu32VH3 | Hu32VH4 | Hu32VH5 | Hu32VH6 |
|---|---|---|---|---|---|---|
| Hu23VL1 (N28T) | Hu32a-15 | Hu32a-29 | Hu32a-43 | Hu32a-57 | Hu32a-71 | Hu32a-85 |
| Hu23VL1 (N28D) | Hu32a-16 | Hu32a-30 | Hu32a-44 | Hu32a-58 | Hu32a-72 | Hu32a-86 |
| Hu23VL1 (G29A) | Hu32a-17 | Hu32a-31 | Hu32a-45 | Hu32a-59 | Hu32a-73 | Hu32a-87 |
| Hu23VL1 (G29V) | Hu32a-18 | Hu32a-32 | Hu32a-46 | Hu32a-60 | Hu32a-74 | Hu32a-88 |
| Hu23VL2 (N28Q) | Hu32a-19 | Hu32a-33 | Hu32a-47 | Hu32a-61 | Hu32a-75 | Hu32a-89 |
| Hu23VL2 (N28L) | Hu32a-20 | Hu32a-34 | Hu32a-48 | Hu32a-62 | Hu32a-76 | Hu32a-90 |
| Hu23VL2 (N28T) | Hu32a-21 | Hu32a-35 | Hu32a-49 | Hu32a-63 | Hu32a-77 | Hu32a-91 |
| Hu23VL2 (N28D) | Hu32a-22 | Hu32a-36 | Hu32a-50 | Hu32a-64 | Hu32a-78 | Hu32a-92 |
| Hu23VL2 (G29A) | Hu32a-23 | Hu32a-37 | Hu32a-51 | Hu32a-65 | Hu32a-79 | Hu32a-93 |
| Hu23VL2 (G29V) | Hu32a-24 | Hu32a-38 | Hu32a-52 | Hu32a-66 | Hu32a-80 | Hu32a-94 |
| Hu23VL1 | Hu32a-25 | Hu32a-39 | Hu32a-53 | Hu32a-67 | Hu32a-81 | Hu32a-95 |
| Hu23VL2 | Hu32a-26 | Hu32a-40 | Hu32a-54 | Hu32a-68 | Hu32a-82 | Hu32a-96 |

Note:
in the table for example, "Hu32a-85" refers to an antibody with antibody light chain variable region of Hu23VL1(N28T) and heavy chain variable region of Hu32VH6, and so on.

Combinations of the antibody light/heavy chain variable regions (for example Hu32a-85) referred to in the above table can be linked with the antibody light/heavy chain constant regions to form full-length antibodies, respectively; unless otherwise specified in the present disclosure, when forming a full-length antibody, the light chain variable region is linked to the Kappa chain constant region shown in SEQ ID NO: 73 to form the antibody light chain, and the heavy chain variable region is linked to the IgG4-AA heavy chain constant region shown in SEQ ID NO: 72 or the IgG4-P heavy chain constant region shown in ID NO: 79 to form the antibody heavy chain, and the name in the table referring to the combination of the antibody light/heavy chain variable regions (for example Hu32a-85) plus the suffix ".IgG4AA" means the full-length antibody formed by ligation with the IgG4-AA heavy chain constant region, plus the suffix ".IgG4P" means the full-length antibody formed by ligation with the IgG4-P heavy chain constant region, for example, "Hu32a-85.IgG4AA" means the full-length antibody formed by linking the heavy chain, formed by linking Hu32VH6 heavy chain variable region and IgG4-AA heavy chain constant region as shown in SEQ ID NO: 72, and the light chain, formed by linking the Hu23VL1(N28T) light chain variable region and the Kappa chain constant region as shown in SEQ ID NO: 73. "Hu32a-85.IgG4P" means the full-length antibody formed by linking the heavy chain, formed by linking Hu32VH6 heavy chain variable region and IgG4-P heavy chain constant region as shown in SEQ ID NO: 79, and the light chain, formed by linking the Hu23VL1 (N28T) light chain variable region and the Kappa chain constant region as shown in SEQ ID NO: 73.

TABLE 15

Combinations of Hu23 heavy chain variable regions and Hu32 light chain variable regions

| VL | Hu23VH1 | Hu23VH2 | Hu23VH3 |
|---|---|---|---|
| Hu32VL1 | Hu23a-57 | Hu23a-59 | Hu23a-61 |
| Hu32VL2 | Hu23a-58 | Hu23a-60 | Hu23a-62 |

Note: in the table for example, "Hu23a-57" refers to an antibody with the combination of the antibody light chain variable region of Hu32VL1 and the heavy chain variable region of Hu23VH1, and so on.

Combinations of the antibody light/heavy chain variable regions (for example Hu23a-57) referred to in the above table can be linked with the antibody light/heavy chain constant regions to form full-length antibodies, respectively; unless otherwise specified in the present disclosure, when forming a full-length antibody, the light chain variable region is linked to the Kappa chain constant region shown in SEQ ID NO: 73 to form the antibody light chain, and the heavy chain variable region is linked to the IgG4-AA heavy chain constant region shown in SEQ ID NO: 72 or the IgG4-P heavy chain constant region shown in ID NO: 79 to form the antibody heavy chain, and the name in the table referring to the combination of the antibody light/heavy chain variable regions (for example Hu32a-85) plus the suffix ".IgG4AA" means the full-length antibody formed by ligation with the IgG4-AA heavy chain constant region, plus the suffix ".IgG4P" means the full-length antibody formed by ligation with the IgG4-P heavy chain constant region, for example, "Hu23a-57.IgG4AA" means the full-length antibody formed by linking the heavy chain, formed by linking Hu23VH1 heavy chain variable region and IgG4-AA heavy chain constant region as shown in SEQ ID NO: 72, and the light chain, formed by linking the Hu32VL1 light chain variable region and the Kappa chain constant region as shown in SEQ ID NO: 73. "Hu23a-57.IgG4P" means the full-length antibody formed by linking the heavy chain, formed by linking Hu23VH1 heavy chain variable region and IgG4-P heavy chain constant region as shown in SEQ ID NO: 79, and the light chain, formed by linking the Hu32VL1 light chain variable region and the Kappa chain constant region as shown in SEQ ID NO: 73.

5. Screening of Humanized Antibodies

The affinity detection of different humanized antibodies was carried out by Biacore (see Test Example 3 for the method) and the results are shown in Table 16. The results showed that different humanized antibodies maintain the ability of binding to PD-1, and some humanized antibodies have affinity even substantially close to those of murine antibodies thereof.

TABLE 16

Affinity of Hu23 humanized antibody to human PD-1

| Antibody | ka (1/Ms) | kd (1/s) | KD (M) |
| --- | --- | --- | --- |
| M23 | 4.57E+04 | 1.32E−04 | 2.89E−09 |
| Hu23-1.IgG4AA | 3.43E+04 | 1.10E−04 | 3.20E−09 |
| Hu23-5.IgG4AA | 2.99E+04 | 1.14E−04 | 3.82E−09 |
| Hu23-2.IgG4AA | 2.74E+04 | 1.61E−04 | 5.86E−09 |
| Hu23-6.IgG4AA | 2.79E+04 | 1.55E−04 | 5.57E−09 |
| Hu23-3.IgG4AA | 2.93E+04 | 1.60E−04 | 5.46E−09 |
| Hu23-7.IgG4AA | 2.77E+04 | 1.66E−04 | 5.97E−09 |
| Hu23-4.IgG4AA | 4.24E+04 | 1.44E−04 | 3.39E−09 |
| Hu23-8.IgG4AA | 4.11E+04 | 1.47E−04 | 3.56E−09 |
| Hu23-9.IgG4AA | 6.16E+04 | 1.32E−04 | 2.15E−09 |
| Hu23-10.IgG4AA | 5.51E+04 | 1.53E−04 | 2.77E−09 |
| Hu23-11.IgG4AA | 4.22E+04 | 1.14E−04 | 2.71E−09 |
| Hu23-12.IgG4AA | 5.45E+04 | 1.10E−04 | 2.02E−09 |
| Hu23-13.IgG4AA | 4.24E+04 | 1.22E−04 | 2.88E−09 |
| Hu23-14.IgG4AA | 7.23E+04 | 1.61E−04 | 2.22E−09 |
| M32 | 7.83E+04 | 4.15E−04 | 5.3E−09 |
| Hu32a-15.IgG4AA | 4.89E+04 | 2.52E−03 | 5.14E−08 |
| Hu32a-29.IgG4AA | 7.89E+04 | 6.20E−04 | 7.86E−09 |
| Hu32a-43.IgG4AA | 8.39E+04 | 6.85E−04 | 8.16E−09 |
| Hu32a-57.IgG4AA | 7.94E+04 | 6.24E−04 | 7.85E−09 |
| Hu32a-71.IgG4AA | 8.60E+04 | 3.96E−04 | 4.61E−09 |
| Hu32a-85.IgG4AA | 9.90E+04 | 3.15E−04 | 3.18E−09 |
| M33 | 3.08E+05 | 2.27E−04 | 7.37E−10 |
| Hu33-1.IgG4AA | 6.61E+04 | 1.28E−03 | 1.93E−08 |
| Hu33-4.IgG4AA | 8.11E+04 | 2.55E−03 | 3.14E−08 |
| Hu33-7.IgG4AA | 7.69E+04 | 2.60E−03 | 3.38E−08 |
| Hu33-2.IgG4AA | 1.35E+05 | 1.43E−04 | 1.06E−09 |

TABLE 16-continued

Affinity of Hu23 humanized antibody to human PD-1

| Antibody | ka (1/Ms) | kd (1/s) | KD (M) |
| --- | --- | --- | --- |
| Hu33-5.IgG4AA | 1.46E+05 | 1.35E−04 | 9.26E−10 |
| Hu33-8.IgG4AA | 1.53E+05 | 1.62E−04 | 1.06E−09 |
| Hu33-3.IgG4AA | 1.25E+05 | 1.36E−04 | 1.09E−09 |
| Hu33-6.IgG4AA | 1.30E+05 | 1.40E−04 | 1.08E−09 |
| Hu33-9.IgG4AA | 1.40E+05 | 1.53E−04 | 1.09E−09 |

Example 3. Construction and Expression of PD-1 Humanized Antibodies

Each humanized antibody VH/VK gene fragment was constructed with the designed primers via PCR, and then was used to construct full-length antibody expressing vector VH-CH1-Fc-pHr/VK-CL-pHr by homologous recombination with the expression vector pHr (with signal peptide and constant region gene (CH1-Fc/CL) fragment). IgG4-P represents S228P (corresponding to position 108 of SEQ ID NO: 72 or SEQ ID NO: 79) mutation, and IgG4-AA represents F234A (corresponding to position 114 of sequence SEQ ID NO: 72 or SEQ ID NO: 79), L235A (corresponding to position 115 of SEQ ID NO: 72 or SEQ ID NO: 79) and S228P (corresponding to position 108 of SEQ ID NO: 72 or SEQ ID NO: 79) mutations. IgG4-AA and IgG4-P antibody formats can be obtained by simple point mutations in the IgG4 antibody format.

```
The sequence of IgG4-AA heavy chain constant
region is as follows (SEQ ID NO: 72):
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEAAGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.

The sequence of the antibody light chain (Kappa
chain) constant region is as follows (SEQ ID
NO: 73):
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC.
```

The constructed IgG4AA form full-length antibody sequences are exemplified as follows:

Hu23-11.IgG4AA antibody heavy chain (SEQ ID NO: 74):
EVQLVQSGAEVKKPGSSVKVSCKASGGTFSDYEMHWVRQAPGQGLEWMGLIDPE
TGGTVYNQKFKDRVTITADKSTSTAYMELSSLRSEDTAVYYCARERFSYYGSTSDW
YFDVWGQGTTVTVSSASTKGPSVFPLAPCSRSTSESTAALGCLVKDYFPEPVTVSW
NSGALTSGVHTFPAVLQSSGLYSLSSVVTVPSSSLGTKTYTCNVDHKPSNTKVDKRV
ESKYGPPCPPCPAPEAAGGPSVFLFPPKPKDTLMISRTPEVTCVVVDVSQEDPEVQF
NWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALHNHYTQKS
LSLSLGK.

Hu23-11.IgG4AA light chain (SEQ ID NO: 75):
DIVMTQTPLSLPVTPGEPASISCRSSQSLVHSTGNTYLEWYLQKPGQSPQLLIYKVSN
RFSGVPDRFSGSGSGTDFTLKISRVEAEDVGVYYCFQGSHVPYTEGGGTKVEIKRTV
AAPSVFIFPPSDEQLKSGTASVVCLLNNEYPREAKVQWKVDNALQSGNSQESVTEQ
DSKDSTYSLSSTLTLSKADYEKHKVYACEVTHQGLSSPVTKSFNRGEC.

Hu32a-85.IgG4AA heavy chain (SEQ ID NO: 76):
EVQLVQSGAEVKKPGSSVKVSCKASDFTFTDYEIHWVKQAPGHGLEWIGLFDPET
GGIVYNQKFKGKATLTADKSTSTAYMEFSSLRSEDTAVYYCTREGYNRDWYFDVW
GQGTTVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKYGP
PCPPCPAPEAAGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSLGK.

Hu32a-85.IgG4AA light chain (same as Hu23-11.IgG4AA light chain, SEQ ID NO: 75):
DIVMTQTPLSLPVTPGEPASISCRSSQSLVHSTGNTYLEWYLQKPGQSPQLLIYKVSN
RFSGVPDRFSGSGSGTDFTLKISRVEAEDVGVYYCFQGSHVPYTFGGGTKVEIKRTV
AAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC.

Hu33-6.IgG4AA heavy chain (SEQ ID NO: 77):
KVQLVESGGGLVQPGGSLRLSCAASGFTFSSYAMSWVRQAPGKGLEWVATISGGG
VDTYYQDNVQGRFTISRDNAKNSLYLQMNSLRAEDTAVYYCASPYGHGYFDVWG
QGTTVTVSSASTKGPSVFPLAPCSRSTSESTAALGCLVKDYFPEPVTVSWNSGALTS
GVHTFPAVLQSSGLYSLSSVVTVPSSSLGTKTYTCNVDHKPSNTKVDKRVESKYGPP
CPPCPAPEAAGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLSLSLGK.

Hu33-6.IgG4AA light chain (SEQ ID NO: 78):
DIQMTQSPSSLSASVGDRVTITCRASQDINNFLNWYQQKPGKAPKLLIYYTSSLHSG
VPSRFSGSGSGTDYTLTISSLQPEDFATYYCQQGNTLPWTFGGGTKVEIKRTVAAPS -continued

VFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC.

The sequence of IgG4-P heavy chain constant region is as follows
(SEQ ID NO: 79):
ASTKGPSVFPLAPCSRSTSESTAALGCLVKDYFPEPVTVSWNSGALTSGVHTFPAVL

QSSGLYSLSSVVTVPSSSLGTKTYTCNVDHKPSNTKVDKRVESKYGPPCPPCPAPEF

LGGPSVFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK.

The sequences of the constructed IgG4-P form full-length antibodies are exemplified as follows:

Hu23-11.IgG4P antibody heavy chain (SEQ ID NO: 80):
EVQLVQSGAEVKKPGSSVKVSCKASGGTFSDYEMIHWVRQAPGQGLEWMGLIDPE

TGGTVYNQKFKDRVTITADKSTSTAYMELSSLRSEDTAVYYCARERFSYYGSTSDW

YFDVWGQGTTVTVSSASTKGPSVFPLAPCSRSTSESTAALGCLVKDYFPEPVTVSW

NSGALTSGVHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHYTQKSLSL

SLGK.

Hu23-11.IgG4P light chain (same as Hu23-11.IgG4AA light chain,
SEQ ID NO: 75):
DIVMTQTPLSLPVTPGEPASISCRSSQSLVHSTGNTYLEWYLQKPGQSPQLLIYKVSN

RFSGVPDRFSGSGSGTDFTLKISRVEAEDVGVYYCFQGSHVPYTFGGGTKVEIKRTV

AAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC.

Hu32a-85.IgG4P heavy chain (SEQ ID NO: 81):
EVQLVQSGAEVKKPGSSVKVSCKASDFTFTDYEIHWVKQAPGHGLEWIGLFDPET

GGIVYNQKFKGKATLTADKSTSTAYMEFSSLRSEDTAVYYCTREGYNRDWYFDVW

GQGTTVTVSSASTKGPSVFPLAPCSRSTSESTAALGCLVKDYFPEPVTVSWNSGALT

SGVHTFPAVLQSSGLYSLSSVVTVPSSSLGTKTYTCNVDHKPSNTKVDKRVESKYGP

PCPPCPAPEFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGK.

Hu32a-85.IgG4P light chain (same as Hu23-11.IgG4AA light chain,
SEQ ID NO: 75):
DIVMTQTPLSLPVTPGEPASISCRSSQSLVHSTGNTYLEWYLQKPGQSPQLLIYKVSN

RFSGVPDRFSGSGSGTDFTLKISRVEAEDVGVYYCFQGSHVPYTFGGGTKVEIKRTV

AAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC.

-continued

Hu33-6.IgG4P heavy chain (SEQ ID NO: 82):
KVQLVESGGGLVQPGGSLRLSCAASGFTFSSYAMSWVRQAPGKGLEWVATISGGG

VDTYYQDNVQGRFTISRDNAKNSLYLQMNSLRAEDTAVYYCASPYGHGYFDVWG

QGTTVTVSSASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDKRVESKYGPP

CPPCPAPEFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQPENNYKT

TPPVLDSDGSFFLYSRLTVDKSRWQEGNVFScSVMHEALHNHYTQKSLSLSLGK.

Hu33-6.IgG4P light chain (same as Hu33-6.IgG4AA light chain,
SEQ ID NO: 78):
DIQMTQSPSSLSASVGDRVTITCRASQDINNFLNWYQQKPGKAPKLLIYYTSSLHSG

VPSRFSGSGSGTDYTLTISSLQPEDFATYYCQQGNTLPWTFGGGTKVEIKRTVAAPS

VFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC.

TEST EXAMPLES

Test Example 1. ELISA Experiment of Anti-PD-1 Antibodies Binding to PD-1 Ligand and Binding Blockade In Vitro PD-L1 on the surface of tumor cells binds to PD-1 on the surface of T cells, thereby inhibiting T cell proliferation. PD-1 antibodies can block the PD-L1/PD-1 signaling pathway by binding to PD-1, thereby stimulating T cell proliferation. The PD-1/PD-L1 binding blockade experiment was used to detect the blocking activity of anti-PD-1 antibodies on the signaling pathway.

In this experiment, after coating of PD-1-His protein (Cat. #10377H08H, Sino Biological) on 96-well plates, the anti-PD-1 antibodies to be tested (including antibodies: Hu23-11.IgG4AA, Hu32a-85.IgG4AA and Hu33-6.IgG4AA, positive control antibody: H005-1 (see H005-1 antibody in WO2015085847)) were separately added and the reaction was incubated; later, HRP-labeled goat anti-human IgG (H+L) antibody (Cat. #109-035-003, Jackson ImmunoResearch) was added and incubated. After washing the plates, the binding amounts of HRP-labeled goat anti-human IgG (H+L) were detected, and the $EC_{50}$ values of the binding of anti-PD-1 antibodies to the ligand PD-1 were calculated.

In this experiment, after coating of PD-1 protein fused with Fc in extracellular region (PD-1-Fc, see SEQ ID NO: 1 for the sequence) on 96-well plates, the anti-PD-1 antibodies to be tested (including antibodies: Hu23-11.IgG4AA, Hu32a-85.IgG4AA and Hu33-6.IgG4AA, positive control antibody: H005-1 (see H005-1 antibody in WO2015085847)) were separately added and incubated; later, biotin-labeled PD-L1/PD-L2 was added and incubated. After washing the plates, the binding amounts of biotin-labeled PD-L1/PD-L2 were detected, and the $IC_{50}$ values of anti-PD-1 antibodies to block the binding of the ligand to PD-L1/PD-L2 were calculated.

CB buffer pH 9.6 (1.59 g $Na_2CO_3$ and 2.93 g $NaHCO_3$ dissolved in 1 L distilled water) was used to dilute PD-1-Fc to 1 µg/ml, which was added to the 96-well plates at a volume of 100 µl/well and allowed to stand at 4° C. for 16 h-20 h. PBS buffer was aspirated from the 96-well plates, and the plates were washed with PBST (pH 7.4 PBS containing 0.05% tween20) buffer once. 120 µl/well PBST/1% milk was added and incubated at room temperature for 1 h for blocking. The blocking solution was removed and the plates were washed with PBST buffer once. 90 µl anti-PD-1 antibody to be tested diluted to appropriate concentration with the sample diluent (pH 7.4 PBS containing 5% BSA, 0.05% Tween20) was added and pre-incubated at 4° C. for 1 h. 10× concentration of biotin-labeled PD-L1/PD-L2 (Beijing Sino Biological Co., Ltd.) (10 µg/ml) was added at a volume of 10 µl/well, shaken and mixed well on a shaker, and then incubated at 37° C. for 1 h. The reaction system was removed and the plates were washed with PBST 6 times. 100 µl/well Streptavidin-Peroxidase Polymer 1:400 diluted with PBST buffer was added and incubated with shaking at room temperature for 50 min. The plates were washed with PBST 6 times. 100 µl/well TMB was added and incubated at room temperature for 5-10 min. 100 µl/well 1 M $H_2SO_4$ was added to stop the reaction. The absorbance values at 450 nm were read by using a microplate reader and the $IC_{50}$ values of the anti-PD-1 antibodies to block the binding of the ligand to PD-L1/PD-L2 were calculated. The data is shown in Table 17 below in detail.

TABLE 17

ELISA of anti-PD-1 antibodies of the present disclosure to bind to PD-1 and to block the binding of the ligand to PD-L1/PD-L2

| | Antigen binding | | PD-1 and PD-L1/PD-L2 binding blockade | |
|---|---|---|---|---|
| Antibody | hu PD-1-his OD value MAX | hu PD-1-his EC50 (ng/ml) | Hu PD-1-Fc/ PD-L1 IC50 (ng/ml) | Hu PD-1-Fc/ PD-L2 IC50(ng/ml) |
| Hu23-11.IgG4AA | 1.46 | 237.3 | 92.35 | 245.1 |
| Hu32a-85.IgG4AA | 1.265 | 135.9 | 78.63 | 205.9 |
| Hu33-6.IgG4AA | 1.706 | 205.6 | 103.5 | 207.2 |
| H005-1 | 1.21 | 113.1 | 109.6 | 225.3 |

The exemplary anti-PD-1 antibodies Hu23-11.IgG4AA, Hu32a-85.IgG4AA and Hu33-6.IgG4AA of the present disclosure can all effectively block the binding of PD-1 to PD-L1/PD-L2, and their blocking activity is similar to that of the positive control antibody.

Test Example 2. Ligand Blockade Test of Exemplary Antibodies

The blocking effect of antibodies on the binding of PD-1 and PD-L1 was studied. The experiment process is briefly described as follows:

CHOK1/PD-L1 cells (Promega) were digested, added to 96-well plates at 100 μL/well and placed in a 37° C., 5% $CO_2$ incubator for incubation for 24 h. The control and samples were diluted to desired concentrations by using PBS. Jurkat/PD-1 cells (Jurkat cells stably transfected with PD-1) were counted and seeded at a certain proportion (90 μL/well) to cell culture plates with CHOK1/PD-L1 cells, and 10 μL/well diluted antibody (antibody: Hu23-11.IgG4AA, Hu32a-85.IgG4AA and Hu33-6.IgG4AA, positive control antibody: H005-1, negative control: IgG4 protein, antibody gradient dilution concentration: 0.3 mg/ml, 3 mg/ml, 30 mg/ml) was added and placed in a 37° C., 5% $CO_2$ incubator for incubation for 5 h. The cell culture plates were taken out and placed at room temperature for 5 min. Then 50 μl Bio-Glo™ Reagent was added to each well and incubated at room temperature for 5 min before reading the plate. The experimental results are shown in FIG. 1.

The results showed that the exemplary anti-PD-1 antibodies Hu23-11.IgG4AA, Hu32a-85.IgG4AA and Hu33-6.IgG4AA in the present disclosure can effectively block the binding of PD-1 and PD-L1.

Test Example 3. BIAcore Antibody Affinity Experiment of Exemplary Antibodies IgG was affinity captured by using a Protein A biosensor chip (Cat. #29127556, GE). Human PD-1 antigen (Cat. #10377H08H, Sino Biological) and Cyno PD-1 antigen (purchased from Sino Biological) flowed across the surface of the chip, and the binding and dissociation curves were obtained by real time detection of PD-1 antibody and antigen PD-1 reaction signals by a Biacore T200 instrument. After the dissociation of each experimental cycle was completed, the biosensor chip was washed and regenerated with 10 mM Glycine-HCl pH 1.5 buffer. The experimental buffer system was 1×HBS-EP buffer solution (Cat #BR-1001-88, GE). After the experiment, GE Biacore T200 Evaluation version 3.0 software was used to fit the data with a (1:1) Langmuir model, and the affinity value was obtained. The results are shown in Table 18.

TABLE 18

Affinity of anti-PD-1 antibodies to human PD1 and simian PD-1

| Antibody | Antigen | ka (1/Ms) | kd (1/s) | KD (M) |
|---|---|---|---|---|
| Hu23-11.IgG4AA | hPD-1-His | 6.06E+04 | 1.13E−04 | 1.86E−09 |
|  | Cyno PD-1 | 4.79E+04 | 1.26E−04 | 2.62E−09 |
| Hu32a-85.IgG4AA | hPD-1-His | 8.56E+04 | 2.78E−04 | 3.25E−09 |
|  | Cyno PD-1 | 1.16E+05 | 4.75E−04 | 4.11E−09 |
| Hu33-6.IgG4AA | hPD-1-His | 1.24E+05 | 1.14E−04 | 9.18E−10 |
|  | Cyno PD-1 | 2.51E+05 | 2.41E−04 | 9.60E−10 |

The results showed that the exemplary anti-PD-1 antibodies Hu23-11.IgG4AA, Hu32a-85.IgG4AA and Hu33-6.IgG4AA of the present disclosure can all bind to human PD-1 and simian PD-1.

Test Example 4. The Effect of Antibodies on IFNγ Secretion by Cells in PBMC-T Lymphocyte Activation Experiment In order to study the effect of anti-PD-1 antibodies on the function of human primary T lymphocytes, human peripheral blood mononuclear cells (PBMC) were collected and purified, stimulated with tuberculin (TB) for 5 days, and the secretion level of cytokine IFNγ was detected. The experiment process is briefly described as follows:

PBMCs were obtained from fresh blood using Ficoll-Hypaque (17-5442-02, GE) for density gradient centrifugation (Stem Cell Technologies), cultured in RPMI 1640 (SH30809.01, GE) medium supplemented with 10% (v/v) FBS (10099-141, Gibco) at 37° C. and 5% $CO_2$.

The freshly isolated and purified PBMCs were adjusted to a density of $2\times10^6$ cells/ml with RPMI 1640 medium. 40 μl tuberculin (97-8800, Synbiotics) was added to 20 mL cell suspension and cultured in a 37° C., 5% $CO_2$ incubator for 5 days. On day 5, the aforementioned cultured cells were collected by centrifugation, resuspended in fresh RPMI 1640 medium, adjusted to a density of $1.1\times10^6$ cells/ml, and seeded into 96-well cell culture plates at 90 μl per well. At the same time added were antibody samples (including the antibodies of the present disclosure: Hu23-11.IgG4AA, Hu32a-85.IgG4AA and Hu33-6.IgG4AA, positive control antibody H005-1, and negative control IgG4 protein, antibody gradient dilution concentration 0.3 mg/ml, 3 mg/ml and 30 mg/ml) gradient diluted with PBS (B320, Shanghai BasalMedia Technologies Co., Ltd.), 10 μl/well. The cell culture plates were placed in a 37° C., 5% $CO_2$ incubator for incubation for 3 days. The cell culture plates were taken out and the cell culture supernatant was collected by centrifugation (4000 rpm, 10 min). IFN-γ levels were detected by using ELISA method (human IFN-γ detection kit (EHC102g.96, Neobioscience)). Instructions of the reagents were referred to for specific operations.

Figure 2:
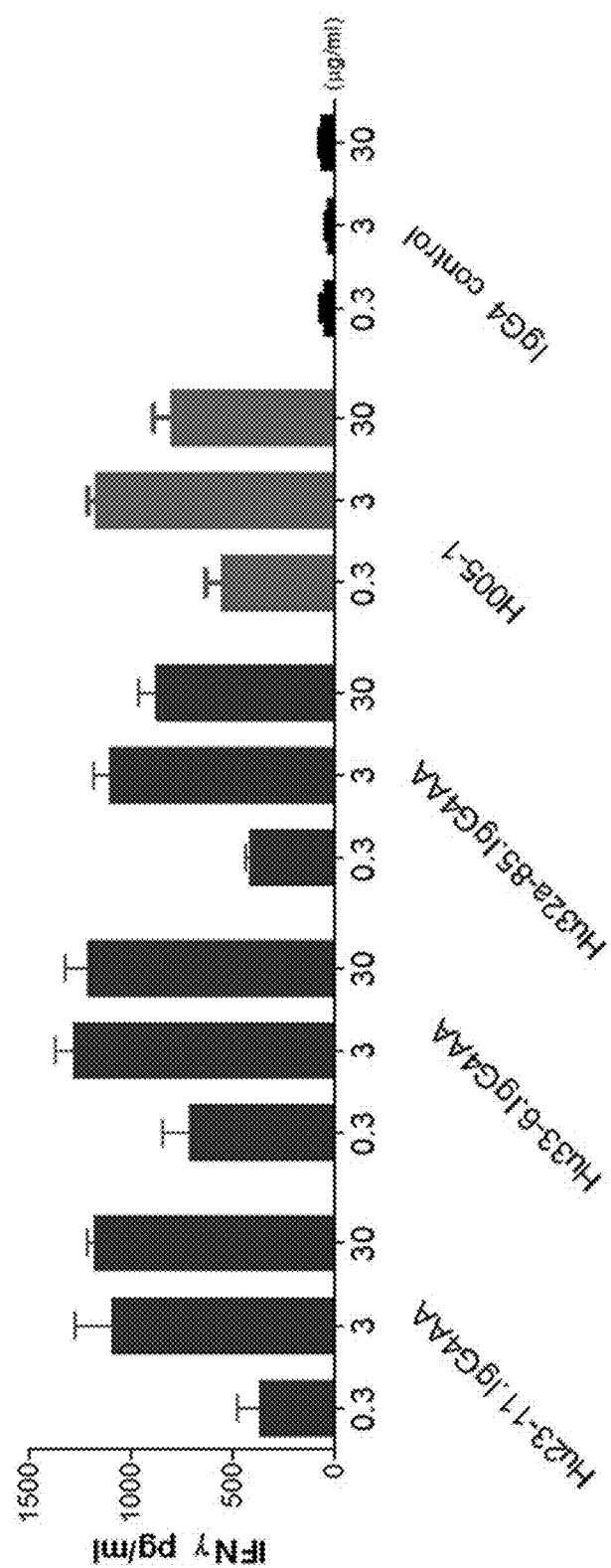
FIG. 2: the effect of anti-PD-1 antibodies on the secretion of IFNγ from PBMC cells.

The test results are shown in FIG. 2. The results showed that the anti-PD-1 antibodies Hu23-11.IgG4AA, Hu32a-85.IgG4AA and Hu33-6.IgG4AA of the present disclosure can all effectively activate IFN-γ secretion.

Test Example 5. The Effect of Anti-PD-1 Antibodies on Colon Cancer Model MC38 in Transgenic PD-1 Mice MC38 cells were inoculated at $5\times10^5$ cells/mouse/100 μl into 90 hPD-1 TG mice (Biocytogen) subcutaneously at the right ribs. After 10 days, animals with too large or too small tumors were excluded. Based on the average tumor volume of about 120 mm$^3$, the mice were randomly divided into: the blank control Vehicle (PBS), the positive control H005-1 3 mpk, Hu32a-85.IgG4AA 1 mpk, Hu32a-85.IgG4AA 3 mpk, Hu23-11.IgG4AA 1 mpk, Hu23-11.IgG4AA 3 mpk and Hu33-6.IgG4AA 3 mpk, a total of 7 groups, each with 8 animals. Antibody of each group was injected intraperitoneally three times a week starting from Day 0. After the first week of administration, the tumors were found to be significantly inhibited. In the second and third weeks, the frequency of administration was adjusted to once a week for a total of 5 administrations. The tumor volume and animal weight were monitored twice a week and the data was recorded. When the tumor volume exceeded 2000 mm$^3$ or most tumors appeared ulcerated or the body weight was reduced by 20%, the tumor-bearing animals were euthanized as the experimental endpoint.

Tumor volume $(TV)=\frac{1}{2}\times L_{long}\times L_{short}^2$

Tumor growth rate $(T/C\%)=(T-T0)/(C-C0)\times100\%$

Tumor growth inhibition rate $(TGI\%)=1-T/C\%$

Wherein T and T0 represent the tumor volumes at the end of the test and the start of the test in the antibody administration group, respectively, and C and C0 represent the tumor volumes at the end of the test and the start of the test in the blank control group, respectively.

Figure 3:
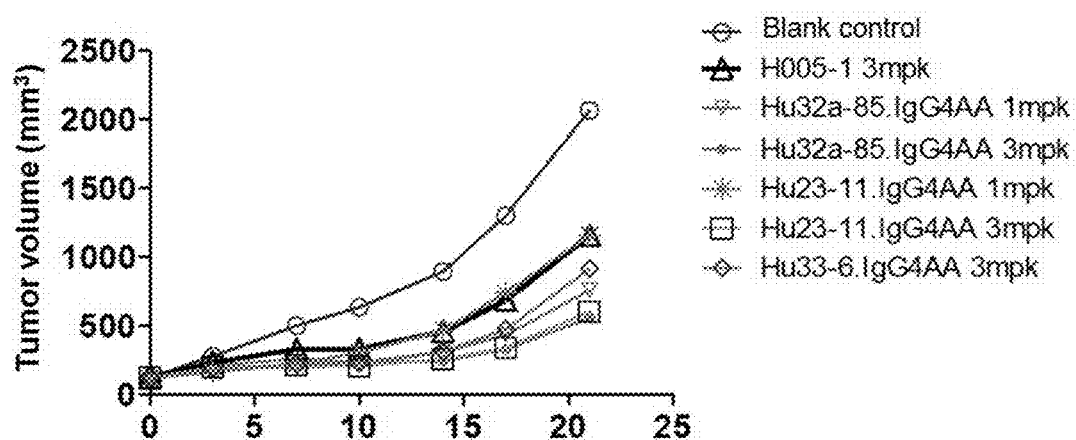
FIG. 3: the efficiency of anti-PD-1 antibodies on xenograft tumor of colon cancer MC38 in mice.

The test results are shown in Table 19 and FIG. 3. The test results showed that compared with the blank control, the antibodies of the present disclosure can all significantly inhibit the growth of mouse colon cancer MC38 xenograft tumors. Among them, Hu32a-85.IgG4AA-3 mpk group had the highest tumor inhibition rate, and the tumor inhibition rate was 77.64% at the last measurement. When the dosing frequency was three times a week for 3 administrations, in the measurement on the seventh day, the results showed that the tumor inhibition rates of the antibodies of the present disclosure were all significantly better than that of the positive control antibody H005-1; after that, the dosing frequency was reduced to once a week, after two administrations (Day 21), the difference in the efficacy of the antibodies of the present disclosure gradually increased, and showed a dose-dependent manner, among which Hu32a-85.IgG4AA was significantly better than the same dose of H005-1 ($p<0.05$). In addition, the tumor-bearing mice can tolerate all the anti-PD-1 antibodies well, with body weight rising steadily during the whole administration process, and no obvious drug-induced body weight loss and other symptoms occurred.

TABLE 19

The effect of anti-PD-1 antibodies on the tumor growth inhibition rate of mouse colon cancer MC38 (mm$^3$)

| Days after first administration | H005-1 | Hu32a-85. IgG4AA | | Hu23-11. IgG4AA | | Hu33-6. IgG4AA |
|---|---|---|---|---|---|---|
| | 3 mpk | 1 mpk | 3 mpk | 1 mpk | 3 mpk | 3 mpk |
| 21 | 46.82% | 67.12% | 77.64% | 45.12% | 75.32% | 59.31% |

Test Example 6. The Effect of Anti-PD-1 Antibodies on Colon Cancer Model MC38 in Transgenic PD-1 Mouse The transgenic PD-1 mice were purchased from ISIS INNOVATION LIMITED, University Offices, Wellington Square, Oxford OX1 2JD, England, and bred in Cephrim Biosciences, Inc. to obtain the fifth generation of mice. MC38 cells were inoculated at $5 \times 10^5$ cells/100 μl/animal into hPD-1 transgenic mice (half females and half males) subcutaneously at posterior right ribs. When the average tumor volume of mice reached between 80-100 mm$^3$, animals with too large or too small body weight or tumors were excluded. According to the tumor volume, the tumor-bearing mice were randomly divided into 5 groups (each with 8 animals): the negative control hIgG control 30 mpk, H005-1 10 mpk, H005-1 30 mpk, Hu33-6.IgG4AA 10 mpk and Hu33-6.IgG4AA 30 mpk. The grouping and administration date was set to Day 0. After grouping, each drug was administered intraperitoneally for a period of 22 days, once every two days, for a total of 11 times. The tumor volume was measured 2 times a week, the body weight was measured, and the data was recorded. The animal body weight and tumor volume of each group were all presented as mean±standard deviation (Mean±SEM), and Graphpad Prism 5 and Excel software were used for graphing, and student t test was used for statistical analysis.

Tumor volume $(TV)=0.5236 \times L_{long} \times L_{short}^2$

Tumor growth rate $T/C \% = (T-T0)/(C-C0) \times 100\%$

Tumor growth inhibition rate % $TGI=1-T/C\%$

Wherein T and T0 represent the tumor volumes at the end of the test and the start of the test in the antibody administration group, respectively, and C and C0 represent the tumor volumes at the end of the test and the start of the test in the blank control group, respectively.

Figure 4:
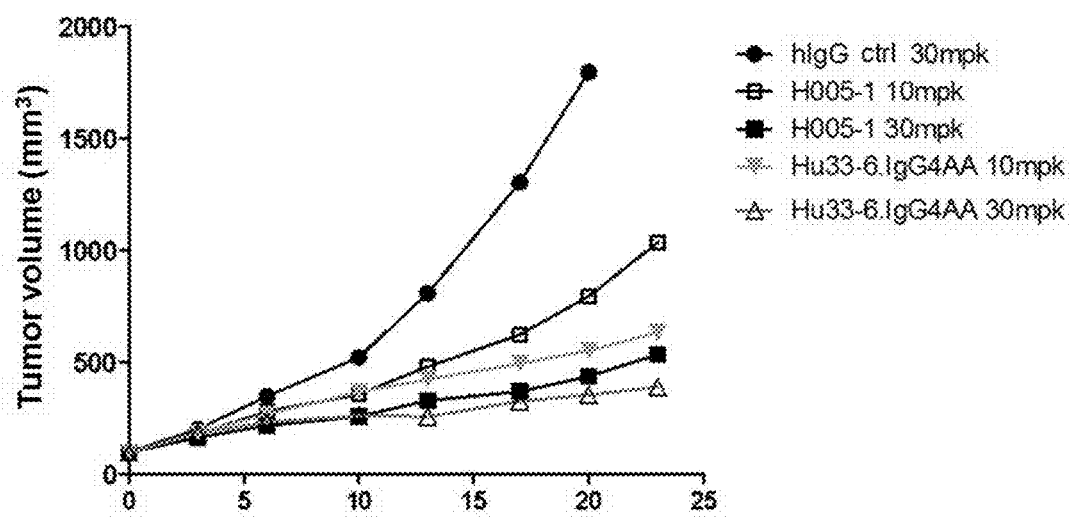
FIG. 4: the effect of anti-PD-1 antibodies on the tumor volume of colon cancer MC38 in mice.

The test results are shown in Table 20 and FIG. 4. The test results showed that compared with the control group, the antibodies of the present disclosure can significantly inhibit the growth of xenograft tumors of mouse colon cancer MC38. Among them, Hu33-6.IgG4AA-30 mpk group has the highest tumor inhibition rate, and the tumor inhibition rate is 80.4% at Day 20. In the low-dose group (10 mpk), the efficacy of Hu33-6.IgG4AA-10 mpk is better than that of the positive control H005-1-10 mpk.

TABLE 20

The effect of anti-PD-1 antibodies on tumor volume of mouse colon cancer MC38

| Days after first administration | hIgG control group | H005-1 10 mpk group | H005-1 30 mpk group | Hu33-6.IgG4AA 10 mpk group | Hu33-6.IgG4AA 30 mpk group |
|---|---|---|---|---|---|
| 0 | 96.2 | 96.1 | 95.3 | 94.7 | 94.5 |
| 20 | 1797.2 | 794.0 | 434.9 | 550.1 | 352.8 |
| 23 | | 1034.2 | 534.1 | 632.4 | 387.6 |

Note: the unit of the average tumor volume of each group in the table is: mm$^3$.

Test Example 7. Pharmacokinetic Test of Anti-PD-1 Antibodies in Cynomolgus Monkeys Cynomolgus monkeys used in the experiment were 6 males, 2-5 years old, 2-5 kg, purchased from Guangdong Frontier Biotechnology Co., Ltd., license number: SOCK (Guangdong) 2015-0037, animal certificate number: 44613900000219.

Housing environment: the room temperature was controlled at 18° C.-26° C., the relative humidity was 40%-70%, and the lighting was alternately light and dark of 12 h. Mice were allowed free access to food and water, except in the case that fasting was required.

The animals were weighed before administration, and the body weight was between 2.81 to 3.52 kg. Administration was performed by using an injection pump for subcutaneous intravenous infusion at the forelimbs or hindlimbs. The dose of each group was all 1 mg/kg (1 mpk), administered by a single intravenous injection at a rate of 0.1 mL/kg/min for an administration period of about 30 min. Before administration and 5 min, 0.25 h, 0.5 h (immediately after the administration was completed), 1 h, 2 h, 4 h, 8 h, 1 d, 2 d, 3 d, 4 d, 5 d, 7 d, 10 d, 13 d, 14 d, 21 d and 28 d after the start of intravenous infusion, whole blood of the animal was collected at the hind limb veins and the serum was separated. Among them, about 2 mL whole blood was collected before administration and 14 d, 21 d and 28 d after the start of intravenous infusion, and about 1 mL whole blood was collected at the rest of blood sampling time points. The blood drug concentration in the serum was detected by ELISA and PK analysis was performed. The results are shown in Table 21.

TABLE 21

Pharmacokinetics of humanized anti-PD1 antibodies in cynomolgus monkeys

|  | Hu23-11.IgG4AA | Hu33-6.IgG4AA |
|---|---|---|
| t1/2 (day) | 5.5 ± 0.7 | 4.6 ± 1.3 |
| Cmax (μg/mL) | 23.75 ± 2.29 | 21.47 ± 2.13 |
| AUC (h*μg/ml) | 2775 ± 241 | 2319 ± 518 |
| CL (ml/day/kg) | 8.7 ± 0.7 | 10.7 ± 2.3 |
| Vz (mL/kg) | 69 ± 3.6 | 67.9 ± 3.4 |

The results showed that Hu23-11.IgG4AA and Hu33-6.IgG4AA have good pharmacokinetic activities.

Although for a clear understanding, the aforementioned invention has been described in detail with the aid of figures and examples, the descriptions and examples should not be interpreted as limiting the scope of the present disclosure. The disclosures of all patents and scientific documents cited in this article are fully and clearly incorporated by reference.

What is claimed is:

1. An anti-PD-1 antibody or antigen-binding fragment thereof, which comprises a heavy chain variable region and a light chain variable region, wherein the combination of the heavy chain variable region and the light chain variable region is selected from any one of the following (a) to (d):
   (a) the heavy chain variable region comprising HCDR1, HCDR2 and HCDR3 as shown in SEQ ID NO: 8, SEQ ID NO: 9 and SEQ ID NO: 10, respectively, and the light chain variable region comprising LCDR2 and LCDR3 as shown in SEQ ID NO: 12 and SEQ ID NO: 13, respectively, and LCDR1 as shown in SEQ ID NO: 11, 47, 48, 49, 50, 51 or 52;
   (b) the heavy chain variable region comprising HCDR1, HCDR2 and HCDR3 as shown in SEQ ID NO: 14, SEQ ID NO: 15 and SEQ ID NO: 16, respectively, and the light chain variable region comprising LCDR1, LCDR2 and LCDR3 as shown in SEQ ID NO: 17, SEQ ID NO: 12 and SEQ ID NO: 18, respectively;
   (c) the heavy chain variable region comprising HCDR1, HCDR2 and HCDR3 as shown in SEQ ID NO: 21, SEQ ID NO: 22 and SEQ ID NO: 23, respectively, and the light chain variable region comprising LCDR1, LCDR2 and LCDR3 as shown in SEQ ID NO: 24, SEQ ID NO: 25 and SEQ ID NO: 26, respectively;
   (d) the heavy chain variable region comprising HCDR1, HCDR2 and HCDR3 as shown in SEQ ID NO: 14, SEQ ID NO: 15 and SEQ ID NO: 16, respectively, and the light chain variable region comprising LCDR2 and LCDR3 as shown in SEQ ID NO: 12 and SEQ ID NO: 13, respectively, and LCDR1 as shown in SEQ ID NO: 49.

2. The anti-PD-1 antibody or antigen-binding fragment thereof according to claim 1, wherein the anti-PD-1 antibody or antigen-binding fragment thereof is a murine antibody or antigen-binding fragment thereof, a chimeric antibody or antigen-binding fragment thereof, or a humanized antibody or antigen-binding fragment thereof.

3. The anti-PD-1 antibody or antigen-binding fragment thereof according to claim 2, wherein the anti-PD-1 antibody is a humanized antibody, said humanized antibody comprises a framework region from a human antibody or a framework region variant thereof, wherein:

the framework region variant has at most 11 amino acid back mutations in each of the light chain framework region and/or the heavy chain framework region of the human antibody, wherein the framework region variant comprises mutation(s) selected from any one of the following (i) to (iii):

(i) 2G amino acid back mutation comprised in the light chain variable region, and/or one or more amino acid back mutations selected from the group consisting of 27Y, 48I, 67T, 69L, 82F and 93T comprised in the heavy chain variable region;

(ii) 2V amino acid back mutation comprised in the light chain variable region, and/or one or more amino acid back mutations selected from the group consisting of 26D, 27F 30T, 38K, 43H, 48I, 66K, 67A, 69L, 82F and 93T comprised in the heavy chain variable region; and (iii) one or more amino acid back mutations selected from the group consisting of 42G, 44V and 71Y comprised in the light chain variable region, and/or 1K and/or 94S amino acid back mutations comprised in the heavy chain variable region; wherein the amino acid positions are numbered and determined according to the Kabat Criteria.

4. The anti-PD-1 antibody or antigen-binding fragment thereof according to claim 2, the combination of the heavy chain variable region and the light chain variable region of the antibody is selected from any one of the following (a) to (f):

(a) a heavy chain variable region, the sequence of which is as shown in SEQ ID NO: 4 or has at least 90% sequence identity with SEQ ID NO: 4, and/or
a light chain variable region, the sequence of which is as shown in SEQ ID NO: 5 or has at least 90% sequence identity with SEQ ID NO: 5;

(b) a heavy chain variable region, the sequence of which is as shown in SEQ ID NO: 6 or has at least 90% sequence identity with SEQ ID NO: 6, and/or
a light chain variable region, the sequence of which is as shown in SEQ ID NO: 7 or has at least 90% sequence identity with SEQ ID NO: 7;

(c) a heavy chain variable region, the sequence of which is as shown in SEQ ID NO: 19 or has at least 90% sequence identity with SEQ ID NO: 19, and/or
a light chain variable region, the sequence of which is as shown in SEQ ID NO: 20 or has at least 90% sequence identity with SEQ ID NO: 20;

(d) a heavy chain variable region, the sequence of which is as shown in SEQ ID NO: 27, 30, 31 or 32, or has at least 90% sequence identity with SEQ ID NO: 27, 30, 31 or 32, and/or
a light chain variable region, the sequence of which is as shown in SEQ ID NO: 28, 29, 34, 35, 53, 54, 55, 56, 57, 58, 59, 60, 61, 62, 63 or 64, or has at least 90% sequence identity with SEQ ID NO: 28, 29, 53, 54, 55, 56, 57, 58, 59, 60, 61, 62, 63 or 64;

(e) a heavy chain variable region, the sequence of which is as shown in SEQ ID NO: 33, 36, 37, 38, 39 or 40, or has at least 90% sequence identity with SEQ ID NO: 33, 36, 37, 38, 39 or 40, and/or
a light chain variable region, the sequence of which is as shown in SEQ ID NO: 34, 35, or 55, or has at least 90% sequence identity with SEQ ID NO: 34, 35, or 55; and (f) a heavy chain variable region, the sequence of which is as shown in SEQ ID NO: 41, 45 or 46, or has at least 90% sequence identity with SEQ ID NO: 41, 45 or 46, and/or
a light chain variable region, the sequence of which is as shown in SEQ ID NO: 42, 43 or 44, or has at least 90% sequence identity with SEQ ID NO: 42, 43 or 44.

5. The anti-PD-1 antibody or antigen-binding fragment thereof according to claim 2, which comprises a heavy chain variable region, the sequence of which is as shown in SEQ ID NO: 27, and a light chain variable region, the sequence of which is as shown in SEQ ID NO: 55.

6. The anti-PD-1 antibody or antigen-binding fragment thereof according to claim 1, wherein the antibody further comprises an antibody constant region.

7. The anti-PD-1 antibody or antigen-binding fragment thereof according to claim 6, wherein the antibody comprises the heavy chain constant region as shown in SEQ ID NO: 72 or 79, and the light chain constant region as shown in SEQ ID NO: 73.

8. The anti-PD-1 antibody or antigen-binding fragment thereof according to claim 1, wherein the anti-PD-1 antibody comprises: a light chain as shown in SEQ ID NO: 78 and a heavy chain as shown in SEQ ID NO: 77 or 82; or the anti-PD-1 antibody comprises a light chain as shown in SEQ ID NO: 75 and a heavy chain as shown in SEQ ID NO: 74, 76, 80 or 81.

9. The anti-PD-1 antibody or antigen-binding fragment thereof according to claim 1, wherein the antigen-binding fragment is selected from the group consisting of Fab, Fab', F(ab')2, single-chain antibody (scFv), dimerized V region (diabody) and disulfide bond stabilized V region (dsFv).

10. The anti-PD-1 antibody or antigen-binding fragment thereof according to claim 1, wherein the antibody is a bispecific antibody, a multispecific antibody or an antibody fusion protein.

11. The anti-PD-1 antibody or antigen-binding fragment thereof according to claim 1, which comprises a heavy chain variable region and a light chain variable region, wherein:
the heavy chain variable region comprising HCDR1, HCDR2 and HCDR3 as shown in SEQ ID NO: 8, SEQ ID NO: 9 and SEQ ID NO: 10, respectively, and
the light chain variable region comprising LCDR1, LCDR2 and LCDR3 as shown in SEQ ID NO: 49, SEQ ID NO: 12 and SEQ ID NO: 13, respectively.

12. The anti-PD-1 antibody or antigen-binding fragment thereof according to claim 1, wherein the anti-PD-1 antibody comprises a light chain as shown in SEQ ID NO: 75 and a heavy chain as shown in SEQ ID NO: 74.

13. A pharmaceutical composition comprising:
a therapeutically effective amount of the anti-PD-1 antibody or antigen-binding fragment thereof according to claim 1 and one or more pharmaceutically acceptable carriers, diluents, buffers or excipients.

14. A nucleic acid molecule encoding the anti-PD-1 antibody or antigen-binding fragment thereof according to claim 1.

15. A host cell comprising the nucleic acid molecule according to claim 14.

16. A method for the immunodetection or determination of PD-1, comprising a step of contacting a sample with the anti-PD-1 antibody or antigen-binding fragment thereof according to claim 1.

17. A kit comprising the anti-PD-1 antibody or antigen-binding fragment thereof according to claim 1.

18. A method for treating diseases associated with PD-1, comprising administering to a subject a therapeutically effective amount of the anti-PD-1 antibody or antigen-binding fragment thereof according to claim 1.

19. The method of claim 18, wherein the disease is selected from the group consisting of: head and neck squamous cell carcinoma, head and neck cancer, brain cancer, glioma, glioblastoma multiforme, neuroblastoma, central nervous system cancer, neuroendocrine tumor, pharyngeal cancer, nasopharyngeal cancer, esophageal cancer, thyroid cancer, malignant pleural mesothelioma, lung cancer, breast cancer, liver cancer, hepatoma, hepatocellular carcinoma, hepatobiliary cancer, pancreatic cancer, gastric cancer, gastrointestinal cancer, bowel cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, myeloproliferative neoplasm, squamous cell carcinoma, Ewing's sarcoma, systemic light chain amyloidosis and Merkel cell carcinoma.

* * * * *